(12) United States Patent
Park et al.

(10) Patent No.: US 9,671,396 B2
(45) Date of Patent: Jun. 6, 2017

(54) SOLID SUBSTRATE COMPRISING ARRAY OF DENDRONS AND METHODS FOR USING THE SAME

(76) Inventors: Joon Won Park, Pohang (KR); Bong Jin Hong, Pohang (KR)

( * ) Notice: Subject to any disclaimer, the term of this patent is extended or adjusted under 35 U.S.C. 154(b) by 756 days.

(21) Appl. No.: 12/102,802

(22) Filed: Apr. 14, 2008

(65) Prior Publication Data

US 2008/0274915 A1    Nov. 6, 2008

Related U.S. Application Data

(63) Continuation-in-part of application No. 10/917,601, filed on Aug. 12, 2004, now Pat. No. 9,201,067, which is a continuation-in-part of application No. 10/363,948, filed as application No. PCT/KR01/01501 on Sep. 1, 2001, now abandoned.

(60) Provisional application No. 60/567,844, filed on May 3, 2004, provisional application No. 60/571,052, filed on May 14, 2004.

(51) Int. Cl.
*G01N 33/00* (2006.01)
*G01N 33/543* (2006.01)
*C09D 201/00* (2006.01)
*C12Q 1/68* (2006.01)

(52) U.S. Cl.
CPC ... *G01N 33/54353* (2013.01); *C09D 201/005* (2013.01); *C12Q 1/6834* (2013.01)

(58) Field of Classification Search
CPC .......... G01N 33/54353; C09D 201/005; C12Q 1/6834
See application file for complete search history.

(56) References Cited

U.S. PATENT DOCUMENTS

| | | | | |
|---|---|---|---|---|
| 4,507,466 A | * | 3/1985 | Tomalia et al. | 528/332 |
| 5,861,319 A | * | 1/1999 | Lin et al. | 436/527 |
| 6,500,650 B1 | * | 12/2002 | Stanton et al. | 435/91.1 |
| 6,884,628 B2 | * | 4/2005 | Hubbell et al. | 436/518 |

FOREIGN PATENT DOCUMENTS

| | | | |
|---|---|---|---|
| WO | WO 99/57323 | * | 11/1999 |
| WO | WO 02/020469 | * | 3/2002 |

OTHER PUBLICATIONS

Balagurusamy et al. (Rational design of the first spherical supramolecular dendrimers self-organized in a novel thermotropic cubic liquid-crystalline phase and the determination of their shape by X-ray analysis, 1997, J. Am. Chem. Soc., vol. 119, pp. 1539-1555).*
Hong et al. (Nanoscale-controlled spacing provides DNA microarrays with the SNP discrimination efficiency in solution phase, 2005, Langmuir, vol. 21, pp. 4257-4261).*

* cited by examiner

*Primary Examiner* — Sudhakar Katakam
(74) *Attorney, Agent, or Firm* — Don D. Cha; Hamilton DeSanctis & Cha, LLP.

(57) ABSTRACT

The present invention provides solid supports comprising a surface bound array of dendrons and methods for using the same.

14 Claims, 13 Drawing Sheets

F1 (Fmoc-(3) acid)
F3 (Fmoc-(9) acid)

SOLID SUBSTRATE COMPRISING ARRAY OF DENDRONS AND METHODS FOR USING THE SAME

CROSS-REFERENCE TO RELATED APPLICATIONS

This application is a continuation-in-part of U.S. patent application Ser. No. 10/917,601, filed Aug. 12, 2004, which is a continuation-in-part of U.S. patent application Ser. No. 10/363,948, filed Mar. 5, 2003, which is a national phase application of PCT Patent Application No. PCT/KR01/01501, filed Sep. 5, 2001. U.S. patent application Ser. No. 10/917,601 also claims the priority benefits of U.S. Provisional Patent Application Nos. 60/567,844, filed May 3, 2004, and 60/571,052, filed May 14, 2004, all of which are incorporated herein by reference in their entirety.

FIELD OF THE INVENTION

The present invention relates to solid supports comprising a surface bound array of dendrons and methods for using the same.

BACKGROUND OF THE INVENTION

Solid substrates having surface bound molecules have been used extensively in recent years in a variety of applications including, but not limited to, diagnostic assays, solid substrate syntheses, purifications, etc. The molecules in these solid substrates are often bound to the solid substrate surface through a linker. These solid substrates typically allow high-throughput, ease of use, and/or ease of purification. While some particular combinations of solid substrates and surface bound molecules show a high specificity and/or selectivity, there is no general method or system for achieving a high specificity and/or selectivity with a wide variety of surface bound molecules and/or solid substrates. These shortcomings are often due in part to the nature of the solid substrate surface, linkers, and/or the surface bound molecules themselves. Often the surface bound molecules and/or the way these molecules are arranged in the solid substrate surface is primarily responsible for these shortcomings. Thus, each different application often requires finding proper combination(s) of solid substrates, linkers, and/or surface bound molecules.

Accordingly, there is a need for general methods and systems for achieving a high specificity and/or selectivity for a wide variety of surface bound molecules and/or solid substrates.

SUMMARY OF THE INVENTION

Some aspects of the invention provide apparatuses, devices, systems and methods for achieving a high specificity and/or selectivity for any application that utilizes solid substrates comprising a surface bound molecule. Generally, the invention utilizes a solid support comprising a plurality of dendrons. In some embodiments, dendrons are conically shaped such that the base portion is attached to the solid support and the apex comprises a functional group. The functional group can optionally include a linker. The linker and/or the functional group portion of the dendron is in general does not have helix or helix-like configuration. Furthermore, in other embodiments, a probe can be attached to the functional group, for example, by nucleophilic addition. Typically, the functional group is a nucleophile that can be used to attach various probes.

Some particular aspects of the invention provide an array of dendrons, said array comprising a planar, non-porous solid support having at least a first surface; and a plurality of dendrons attached to said first surface of said solid support, wherein each of said dendron comprises:
  a central atom;
  a functional group that is attached to said central atom through a linker and is adapted for attaching a probe; and
  a base portion attached to said central atom and having a plurality of termini that are attached to said first surface of said solid support,
wherein when said functional group is attached to a probe, the discrimination efficiency of the probe is at least 80%.

Within these aspects of the invention, in some embodiments, when the functional group is attached to an oligonucleotide probe of 15 nucleotides, the single nucleotide polymorphism (SNP) discrimination efficiency is about 1:0.05.

In other embodiments, when said functional group is attached to an oligonucleotide probe of 15 nucleotides, the amount of non-specific binding is reduced by at least about 60% compared to the oligonucleotide probe attached to a non-dendron.

Still in other embodiments, the functional group is capable of forming a bond with the probe by a nucleophilic substitution reaction.

Yet in other embodiments, each of the dendron is of the formula:

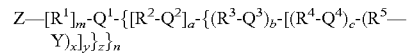

$$Z\text{—}[R^1]_m\text{-}Q^1\text{-}\{[R^2\text{-}Q^2]_a\text{-}\{(R^3\text{-}Q^3)_b\text{-}[(R^4\text{-}Q^4)_c\text{-}(R^5\text{—}Y)_x]_y\}_z\}_n \qquad \mathrm{I}$$

wherein
  each of m, a, b, and c is independently 0 or 1;
  x is 1 when c is 0 or when c is 1, x is an integer from 1 to the oxidation state of $Q^4$-1;
  y is 1 when b is 0 or when b is 1, y is an integer from 1 to the oxidation state of $Q^3$-1;
  z is 1 when a is 0 or when a is 1, z is an integer from 1 to the oxidation state of $Q^2$-1;
  n is an integer from 1 to the oxidation state of $Q^1$-1;
  $Q^1$ is a central atom having the oxidation state of at least 3;
  each of $Q^2$, $Q^3$ and $Q^4$ is independently a branch atom having the oxidation state of at least 3;
  each of $R^1$, $R^2$, $R^3$, $R^4$, and $R^5$ is independently a linker;
  Z is the functional group that is optionally protected; and
  each of Y is independently a functional group on the terminus of said base portion,
    wherein a plurality of Y are attached to said first surface of said solid support, provided the product of n, x, y, and z is at least 3.

In some instances within these embodiments, Z is a nucleophile. In other instances, Z is an electrophile. Still in other instances, Z comprises a heteroatom selected from the group consisting of N, O, S, P, and a combination thereof. Yet in other instances, the planar non-porous solid support is glass.

Still other aspects of the invention provide a method for producing a solid support comprising a plurality of dendrons on its surface, wherein said solid support comprises at least a first surface comprising a surface functional group, and wherein each of the dendron comprises:

a central atom;
a functional group that is attached to said central atom through a linker; and
a base portion attached to the central atom and having a plurality of termini each having a functional group.

The method generally comprises contacting a plurality of dendrons with the solid support surface under conditions sufficient to form a bond between the surface functional group on the first surface of the solid support and the functional group on the terminus of the base such that a plurality of bonds are formed between the base portion of the dendron and the first surface of the solid support.

Within these aspects of the invention, in some embodiments the bond that formed between the surface functional group on the first surface of the solid support and the functional group on the terminus of the base is a covalent bond.

In other embodiments, the bond between the surface functional group on the first surface of the solid support and the functional group on the terminus of the base is formed by a nucleophilic substitution reaction.

Still in other embodiments, the solid support is a non-porous solid support.

Yet in other embodiments, the solid support is a planar non-porous solid support. In some instances within these embodiments, the planar non-porous solid support is a glass.

In other embodiments, the functional group that is attached to the central atom through the linker comprises a protecting group.

Still in other embodiments, the dendrons are attached to predefined regions of the solid support.

Yet other aspects of the invention provide a method for detecting a presence of a ligand in a fluid medium comprising:
 contacting the fluid medium with a solid substrate, wherein the solid substrate comprises:
  array of dendrons on its surface, wherein each of said dendron comprises:
  a central atom;
  a probe that is attached to the central atom optionally through a linker; and
  a base portion attached to the central atom and having a plurality of termini that are attached to the first surface of the solid support; and
 determining the presence of a probe-ligand complex, wherein the presence of the probe-ligand complex is an indication that the fluid medium comprises the ligand.

In some embodiments, the probe-ligand complex is an oligonucleotide-complementary oligonucleotide complex, an oligopeptide-binding oligopeptide complex, a receptor-substrate complex, or a complex.

Still in other embodiments, the receptor-substrate complex comprises a drug-drug receptor complex, an enzyme-enzyme substrate complex, or an antibody-antigen complex.

Yet in other embodiments, such methods are capable of discriminating a single nucleotide polymorphism in the oligonucleotide-complementary oligonucleotide complex.

In other embodiments, such methods are capable of discriminating a single amino acid mismatch in the oligopeptide-binding oligopeptide complex.

Yet other aspects of the invention provide a composition comprising an array of dendrons that are bound to a surface of a planar, non-porous solid support. Each of the dendron comprises:
 a central atom;
 a functional group that is attached to the central atom through a linker; and
 a base portion attached to said central atom and having a plurality of termini that are attached to the surface of said solid support.

The central atom of such a composition comprises a probe for detecting a ligand. Typically, the discrimination efficiency of compositions of the invention is at least about 50%, often at least about 70%, more often at least about 80%, still more often at least about 90%, and still more often at least about 95%.

In many embodiments, the dendron is conically-shaped. Generally the base portion of the cone comprises the plurality of termini. In some instances the base portion comprises more than three termini that are attached to the surface of said solid support. In other instances, the base portion comprises at least six termini that are attached to the surface of said solid support. Still in other instances, the base portion comprises at least nine termini that are attached to the surface of said solid support. Yet in other instances, the base portion comprises at least twelve termini that are attached to the surface of said solid support. Still yet in other instances, the base portion comprises at least twenty one termini that are attached to the surface of said solid support.

Still in other embodiments, the probe comprises an oligonucleotide, an oligopeptide, an enzyme, a substrate, a drug, a drug-receptor, or a combination thereof.

BRIEF DESCRIPTION OF THE DRAWINGS

FIG. 2a shows a scheme for surface modification and hybridization. FIG. 2b shows the molecular structure of the employed dendron. FIG. 2c shows the DNA sequence of the probe and target DNA strands.

Each data point represents the mean value (n=3), and the error bar the standard deviation.

Figure 12:
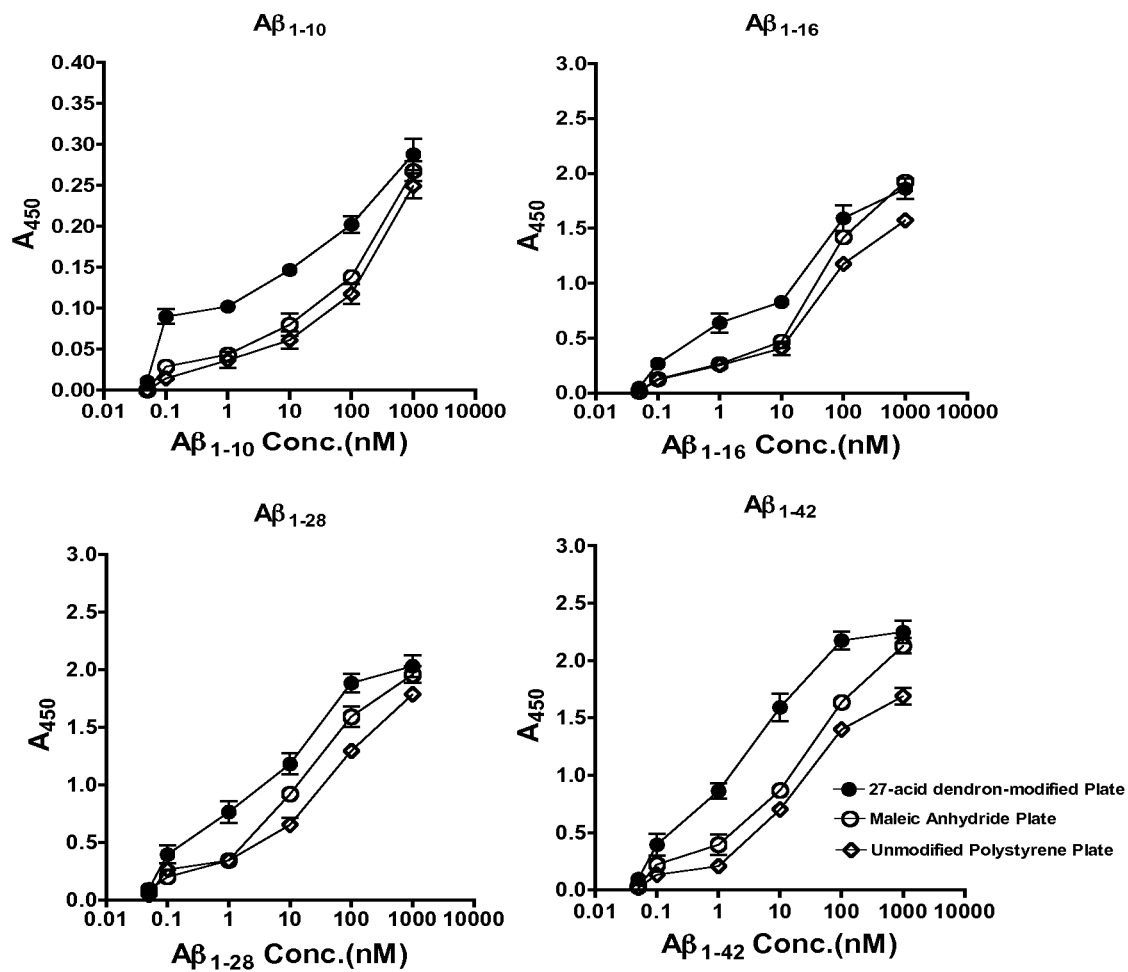

FIG. 12 is ELISA of different Aβ fragments on 27-acid-immobilized plate. Each data point represents the mean value (n=3), and the error bar the standard deviation.

Figure 13:
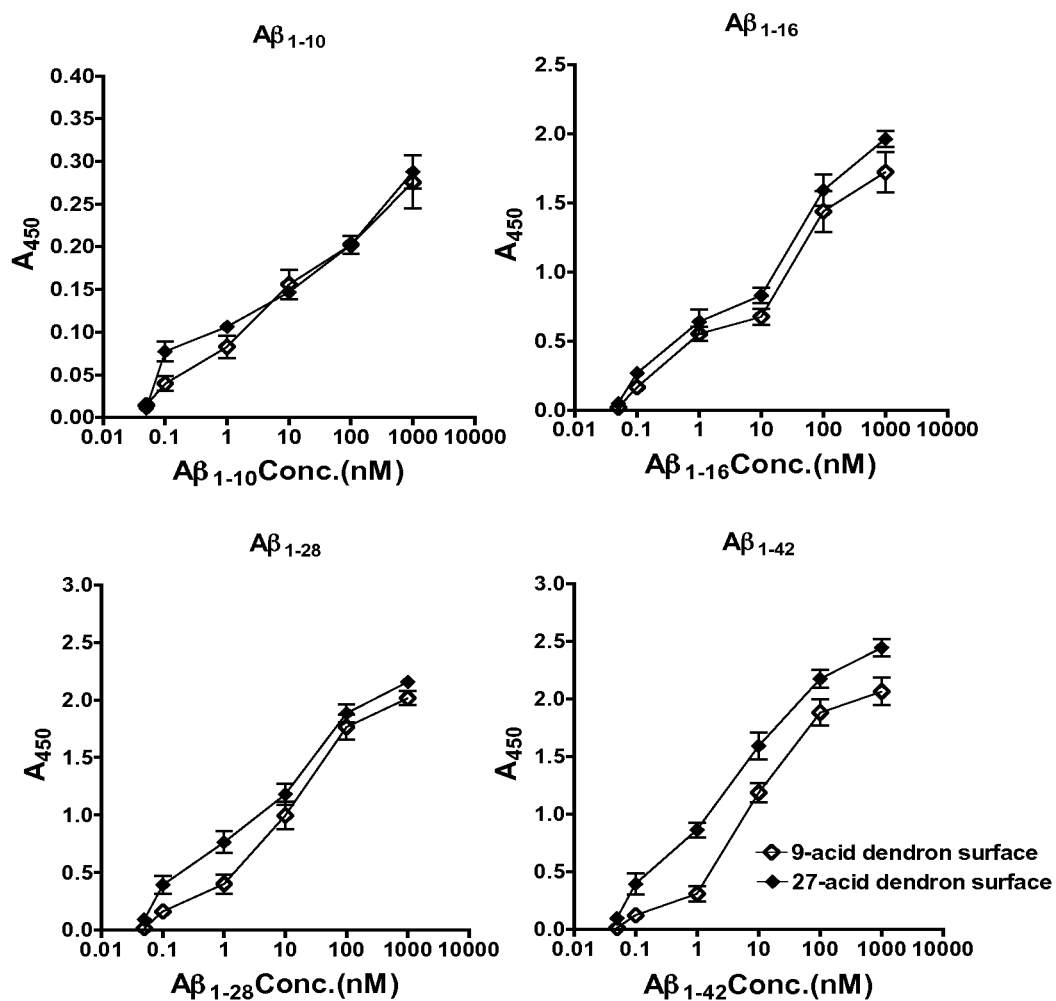

FIG. 13 shows direct comparison of the 9-acid- and 27-acid-immobilized surfaces for detection of different immobilized Aβ fragments by an ELISA. Each data point represents the mean value (n=3), and the error bar the standard deviation.

Figure 14:
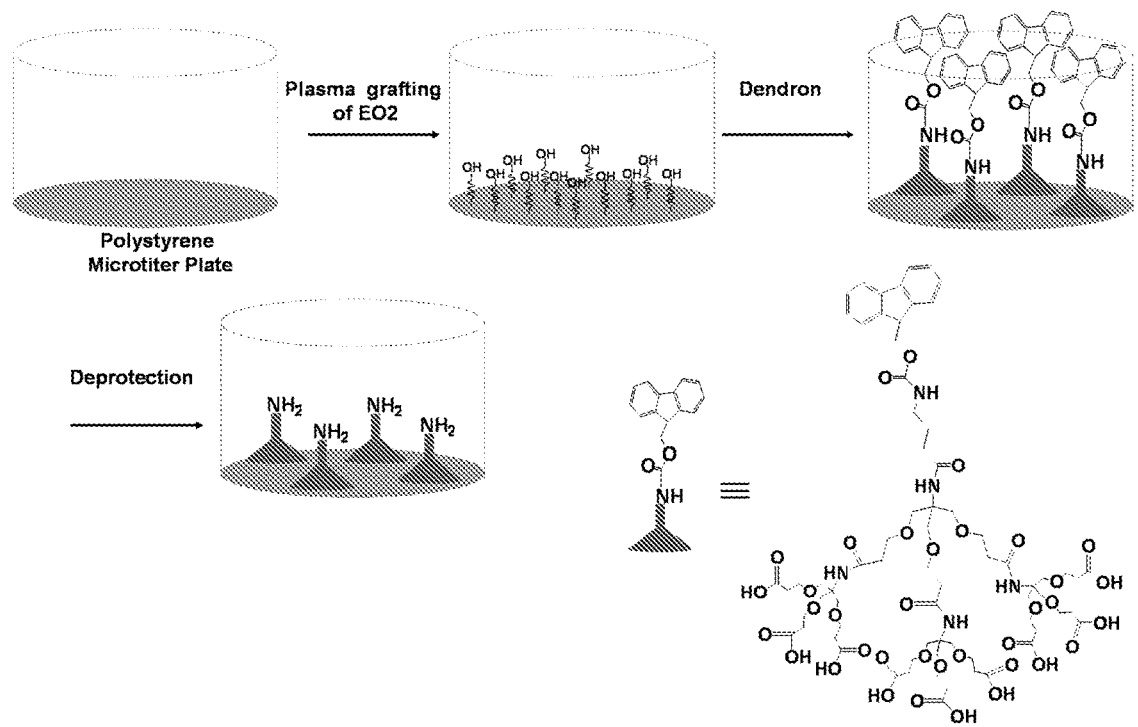

FIG. 14 is a schematic drawing of the surface treatment for the dendron immobilization on polystyrene microtiter plates.

Figure 15:
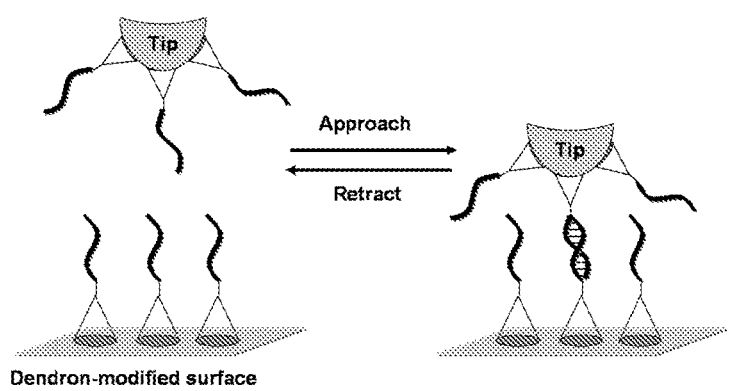

FIG. 15 is schematic diagram of molecular recognition interaction force.

Figure 16:
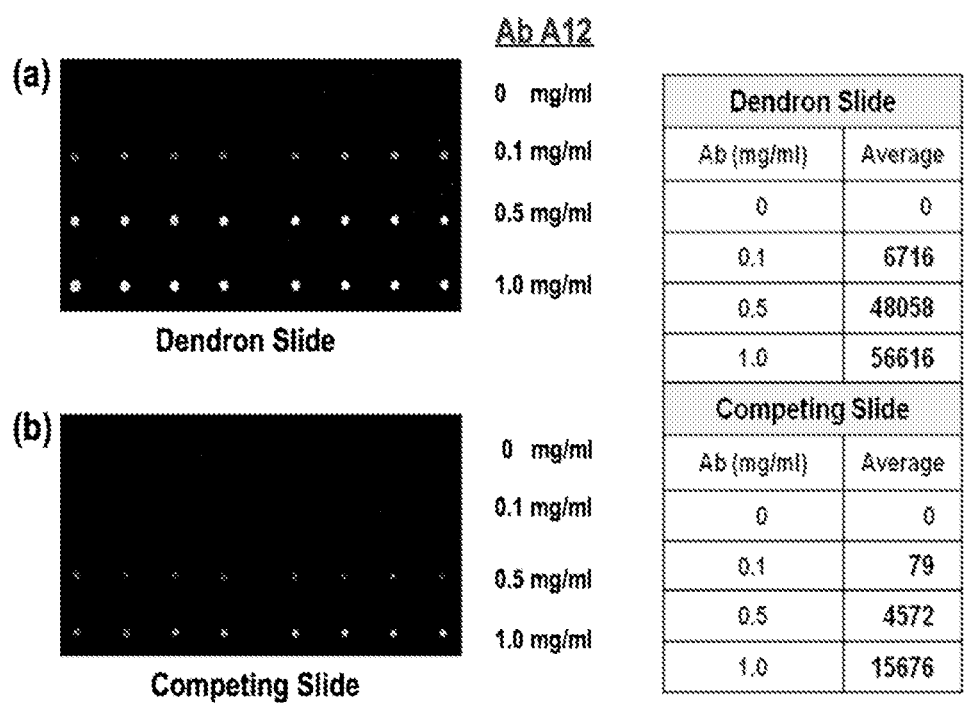

FIG. 16 is fluorescence images of antibody microarrays after hybridization with apoA-I. (a) Dendron slide and (b) Hydrogel slide. The image was scanned by ScanArray Lite (GSI Lumonics) and signal intensity was analyzed by Imagene 4.0 software (Biodiscovery).

Figure 17:
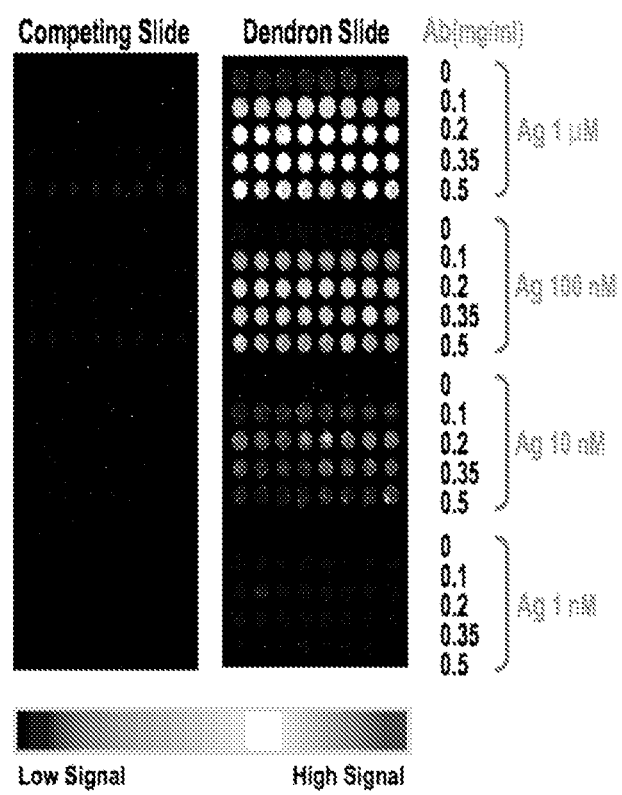

FIG. 17 is fluorescence images of antibody microarrays after hybridization with apoA-I at different concentrations of from 1 nM to 1 μM. The image was scanned by ScanArray Lite (GSI Lumonics) and signal intensity was analyzed by Imagene 4.0 software (Biodiscovery).

DETAILED DESCRIPTION OF THE INVENTION

As used herein, "aptamer" means a single-stranded, partially single-stranded, partially double-stranded or double-stranded nucleotide sequence, advantageously replicable nucleotide sequence, capable of specifically recognizing a selected nonoligonucleotide molecule or group of molecules by a mechanism other than Watson-Crick base pairing or triplex formation.

As used herein, "bifunctional," "trifunctional" and "multifunctional," when used in reference to a synthetic polymer or multivalent homo- or heteropolymeric hybrid structure, mean bivalent, trivalent or multivalent, as the case may be, or comprising two, three or multiple specific recognition elements, defined sequence segments or attachment sites.

As used herein, "biomimetic" means a molecule, group, multimolecular structure or method that mimics a biological molecule, group of molecules, structure.

As used herein, "dendritic molecule" is a molecule exhibiting regular dendritic branching, formed by the sequential or generational addition of branched layers to or from a core.

The term "dendron" refers to a polymer exhibiting regular dendritic branching, formed by the sequential or generational addition of branched layers to or from a core. The term dendritic polymer encompasses "dendrimers", which are characterized by a core, at least one interior branched layer, and a surface branched layer (see, e.g., Petar et al. Pages 641-645 In Chem. in Britain, (August 1994). A "dendron" is a species of dendrimer having branches emanating from a focal point or a central atom, which is or can be joined to a core, either directly or through a linking moiety to form a dendrimer. Many dendrimers comprise two or more dendrons joined to a common core.

Dendrons include, but are not limited to, symmetrical and asymmetrical branching dendrimers, cascade molecules, arborols, and the like. In some embodiments, the branch arms are of equal length. However, it is also contemplated that asymmetric dendrimers may also be used.

Further, it is understood that even though not formed by regular sequential addition of branched layers, hyperbranched polymers, e.g., hyperbranched polyols, may be equivalent to a dendritic polymer where the branching pattern exhibits a degree of regularity approaching that of a dendrimer.

As used herein, "hyperbranched" or "branched" as it is used to describe a macromolecule or a dendron structure is meant to refer to a plurality of polymers having a plurality of termini which are able to bind covalently or ionically to a substrate. In one embodiment, the macromolecule comprising the branched or hyperbranched structure is "pre-made" and is then attached to a substrate. Accordingly, the inventive macromolecule excludes polymer cross-linking methods as disclosed in U.S. Pat. No. 5,624,711 (Sundberg et al.).

As used herein, "immobilized" means insolubilized or comprising, attached to or operatively associated with an insoluble, partially insoluble, colloidal, particulate, dispersed, suspended and/or dehydrated substance or a molecule or solid phase comprising or attached to a solid support.

As used herein, the terms "array" and "library" are used interchangeably herein and refer to a random or nonrandom mixture, collection or assortment of molecules, materials, surfaces, structural shapes, surface features or, optionally and without limitation, various chemical entities, monomers, polymers, structures, precursors, products, modifications, derivatives, substances, conformations, shapes, or features.

As used herein, "linker molecule," and "linker" when used in reference to a molecule that joins the branched portion of a size-controlled macromolecule such as a branched/linear polymer to a protecting group or a ligand. Linkers may include, for instance and without limitation, spacer molecules, for instance selected molecules capable of attaching a ligand to a dendron.

As used herein, "low density" refers to about 0.005 to about 0.5 probe/nm$^2$, preferably about 0.01 to about 0.2, more preferably about 0.01 to about 0.1, and most preferably about 0.05 probe/nm$^2$.

As used herein, "molecular mimics" and "mimetics" are natural or synthetic nucleotide or normucleotide molecules or groups of molecules designed, selected, manufactured, modified or engineered to have a structure or function equivalent or similar to the structure or function of another molecule or group of molecules, e.g., a naturally occurring, biological or selectable molecule. Molecular mimics include molecules and multimolecular structures capable of functioning as replacements, alternatives, upgrades, improvements, structural analogs or functional analogs to natural, synthetic, selectable or biological molecules.

As used herein, "nucleotide analog" refers to molecules that can be used in place of naturally occurring bases in nucleic acid synthesis and processing, preferably enzymatic as well as chemical synthesis and processing, particularly modified nucleotides capable of base pairing and optionally synthetic bases that do not comprise adenine, guanine, cytosine, thymidine, uracil or minor bases. This term includes, but is not limited to, modified purines and pyrimidines, minor bases, convertible nucleosides, structural analogs of purines and pyrimidines, labeled, derivatized and modified nucleosides and nucleotides, conjugated nucleosides and nucleotides, sequence modifiers, terminus modifiers, spacer modifiers, and nucleotides with backbone modifications, including, but not limited to, ribose-modified nucleotides, phosphoramidates, phosphorothioates, phosphonamidites, methyl phosphonates, methyl phosphoramidites, methyl phosphonamidites, 5'-β-cyanoethyl phosphoramidites, methylenephosphonates, phosphorodithioates, peptide nucleic acids, achiral and neutral internucleotidic linkages and nornucleotide bridges such as polyethylene glycol, aromatic polyamides and lipids.

As used herein, "polymer" or "branched/linear polymer" refers to a molecule having a branched structure at one end of the molecule and a linear portion at the other end so that the branched portion binds to a substrate and the linear portion binds to a ligand, probe or a protecting group.

As used herein, "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term may also include variants on the traditional peptide linkage joining the amino acids making up the polypeptide.

As used herein, "protecting group" refers to a group that is joined to a reactive group (e.g., a hydroxyl or an amine) on a molecule. The protecting group is chosen to prevent reaction of the particular radical during one or more steps of a chemical reaction. Generally the particular protecting group is chosen so as to permit removal at a later time to restore the reactive group without altering other reactive groups present in the molecule. The choice of a protecting group is a function of the particular radical to be protected and the compounds to which it will be exposed. The selection of protecting groups is well known to those of skill in the art. See, for example Greene et al., Protective Groups in Organic Synthesis, 2nd ed., John Wiley & Sons, Inc. Somerset, N.J. (1991), which is incorporated by reference herein in its entirety.

As used herein, "protected amine" refers to an amine that has been reacted with an amino protecting group. An amino protecting group prevents reaction of the amide function during attachment of the branched termini to a solid support in the situation where the linear tip functional group is an amino group. The amino protecting group can be removed at a later time to restore the amino group without altering other reactive groups present in the molecule. For example, the exocyclic amine may be reacted with dimethylformamide diethylacetal to form the dimethylaminomethylenamino function. Amino protecting groups generally include carbamates, benzyl radicals, imidates, and others known to those of skill in the art. Preferred amino protecting groups include, but are not limited to, p-nitrophenylethoxycarbonyl or dimethyaminomethylenamino.

As used herein, "regular intervals" refers to the spacing between the tips of the size-controlled macromolecules, which is a distance from about 1 nm to about 100 nm so as to allow room for interaction between the target-specific ligand and the target substantially without steric hindrance. Thus, the layer of macromolecules on a substrate is not too dense so that specific molecular interactions may occur.

As used herein, "solid support" refers to a composition comprising an immobilization matrix such as but not limited to, insolubilized substance, solid phase, surface, substrate, layer, coating, woven or nonwoven fiber, matrix, crystal, membrane, insoluble polymer, plastic, glass, biological or biocompatible or bioerodible or biodegradable polymer or matrix, microparticle or nanoparticle. Solid supports include, for example and without limitation, monolayers, bilayers, commercial membranes, resins, matrices, fibers, separation media, chromatography supports, polymers, plastics, glass, mica, gold, beads, microspheres, nanospheres, silicon, gallium arsenide, organic and inorganic metals, semiconductors, insulators, microstructures and nanostructures. Microstructures and nanostructures may include, without limitation, microminiaturized, nanometer-scale and supramolecular probes, tips, bars, pegs, plugs, rods, sleeves, wires, filaments, and tubes.

As used herein, "specific binding" refers to a measurable and reproducible degree of attraction between a ligand and its specific binding partner or between a defined sequence segment and a selected molecule or selected nucleic acid sequence. The degree of attraction need not be maximized to be optimal. Weak, moderate or strong attractions may be appropriate for different applications. The specific binding which occurs in these interactions is well known to those skilled in the art. When used in reference to synthetic defined sequence segments, synthetic aptamers, synthetic heteropolymers, nucleotide ligands, nucleotide receptors, shape recognition elements, and specifically attractive surfaces. The term "specific binding" may include specific recognition of structural shapes and surface features. Otherwise, specific binding refers explicitly to the specific, saturable, noncovalent interaction between two molecules (i.e., specific binding partners) that can be competitively inhibited by a third molecule (i.e., competitor) sharing a chemical identity (i.e., one or more identical chemical groups) or molecular recognition property (i.e., molecular binding specificity) with either specific binding partner. The competitor may be, e.g., a cross-reactant, or analog of an antibody or its antigen, a ligand or its receptor, or an aptamer or its target. Specific binding between an antibody and its antigen, for example, can be competitively inhibited either by a cross-reacting antibody or by a cross-reacting antigen. The term "specific binding" may be used for convenience to approximate or abbreviate a subset of specific recognition that includes both specific binding and structural shape recognition.

As used herein, "substrate," when used in reference to a substance, structure, surface or material, means a composition comprising a nonbiological, synthetic, nonliving, planar, spherical or flat surface that is not heretofore known to comprise a specific binding, hybridization or catalytic recognition site or a plurality of different recognition sites or a number of different recognition sites which exceeds the number of different molecular species comprising the surface, structure or material. The substrate may include, for example and without limitation, semiconductors, synthetic (organic) metals, synthetic semiconductors, insulators and dopants; metals, alloys, elements, compounds and minerals; synthetic, cleaved, etched, lithographed, printed, machined and microfabricated slides, devices, structures and surfaces; industrial polymers, plastics, membranes; silicon, silicates, glass, metals and ceramics; wood, paper, cardboard, cotton, wool, cloth, woven and nonwoven fibers, materials and fabrics; nanostructures and microstructures unmodified by immobilization probe molecules through a branched/linear polymer.

As used herein, "target-probe binding" means two or more molecules, at least one being a selected molecule, attached to one another in a specific manner. Typically, a first selected molecule may bind to a second molecule that either indirectly, e.g., through an intervening spacer arm, group, molecule, bridge, carrier, or specific recognition partner, or directly, i.e., without an intervening spacer arm, group, molecule, bridge, carrier or specific recognition partner, advantageously by direct binding. A selected molecule may specifically bind to a nucleotide via hybridization. Other noncovalent means for conjugation of nucleotide and nornucleotide molecules include, e.g., ionic bonding, hydrophobic interactions, ligand-nucleotide binding, chelating agent/metal ion pairs or specific binding pairs such as avidin/biotin, streptavidin/biotin, anti-fluorescein/fluorescein, anti-2,4-dinitrophenol (DNP)/DNP, anti-peroxidase/peroxidase, anti-digoxigenin/digoxigenin or, more generally, receptor/ligand. For example, a reporter molecule such as alkaline phosphatase, horseradish peroxidase, β-galactosidase, urease, luciferase, rhodamine, fluorescein, phycoerythrin, luminol, isoluminol, an acridinium ester or a fluorescent microsphere which is attached, e.g., for labeling purposes, to a selected molecule or selected nucleic acid sequence using avidin/biotin, streptavidin/biotin, anti-fluorescein/fluorescein, anti-peroxidase/peroxidase, anti-DNP/DNP, anti-digoxigenin/digoxigenin or receptor/ligand (i.e., rather than being directly and covalently attached) may be conjugated to the selected molecule or selected nucleic acid sequence by means of a specific binding pair.

Unless the context requires otherwise, the term "ligand" refers to any substance that is capable of binding selectively with a probe. A ligand can be an antigen, an antibody, an oligonucleotide, an oligopeptide (including proteins, hormone, etc.), an enzyme, a substrate, a drug, a drug-receptor, cell surface, receptor agonists, partial agonists, mixed agonists, antagonists, response-inducing or stimulus molecules, drugs, hormones, pheromones, transmitters, autacoids, growth factors, cytokines, prosthetic groups, coenzymes, cofactors, substrates, precursors, vitamins, toxins, regulatory factors, antigens, haptens, carbohydrates, molecular mimics, structural molecules, effector molecules, selectable molecules, biotin, digoxigenin, crossreactants, analogs, competitors or derivatives of these molecules as well as library-selected nonoligonucleotide molecules capable of specifically binding to selected targets and conjugates formed by attaching any of these molecules to a second molecule, and any other molecule that binds selectively with a corresponding probe.

Unless the context requires otherwise, the term "probe" refers to any substance that is bound to a substrate surface and is capable of binding selectively with a corresponding ligand. A probe can be an antigen, an antibody, an oligonucleotide, an oligopeptide (including proteins, hormone, etc.), an enzyme, a substrate, a drug, a drug-receptor, cell surface, and any other molecule that binds selectively with a corresponding ligand.

It should be appreciated that the terms "ligand" and "probe" do not refer to any particular substance or size relationship. These terms are only operational terms that indicate selective binding between the ligand and the corresponding probe where the moiety that is bound to a substrate surface is referred to as a probe and any substance that selectively binds to the probe is referred to as a ligand. Thus, if an antibody is attached to the substrate surface then the antibody is a probe and the corresponding antigen is a ligand. However, if an antigen is attached to the substrate surface then the antigen is a probe and the corresponding antibody is a ligand.

The concentration of a probe on a substrate surface is one of the key factors that governs interactions between immobilized probe and their corresponding ligand. In spite of several advantages, probes immobilized at high densities frequently have chemical and biological properties that are substantially different from those of the same probe presented in a natural environment. Moreover, non-inert probes of a high density may promote nonspecific probe-ligand interaction. Varying the density of surface bound probes to relieve the surface materials from steric hinderance while also maintaining signal intensities, specificity, and an apparent binding capacity sufficient for applications such as biosensors and biochips, is desirable.

Conventionally, the functional group densities of the thin film are commonly adjusted by co-deposition of both an inert adsorbate and a functionalized one. However, phase separation into microscopic or nanoscopic domains with distinct functional groups is difficult to prevent especially when strong inter-group interactions are present.

Compositions and methods of the invention provide the probe density that significantly reduces the phase separation. Some embodiments of the invention provide a substrate comprising a plurality of conically shaped dendrimers on its surface. Within these embodiments, in some instances the terminus of each dendrimer is capable of binding to the substrate surface and the apex of each dendrimer is reactive for the immobilization of probes.

The present inventors have shown that multiple ionic attraction between cations on the glass substrates and anionic carboxylates at the termini of the dendrimers was successful in generating a well-behaved monolayer and often providing an inter-probe spacing over 24 Å. In one particular instance, to facilitate deprotection and enhance the reactivity of the apex of the dendrimer, a 9-fluorenylmethoxycarbonyl (Fmoc) group and a spacer is used. In some other particular embodiments, the dendrimer is attached to the substrate surface by a covalent bond between the carboxylic acid group of the dendrimer terminus and the amine functional group that is present on the substrate surface, which provides enhanced environmental stability compared to conventional method of attaching via ionic interactions.

Some aspects of the invention provide an array of dendrons. Generally, the array comprises a solid support having at least a first surface and a plurality of dendrons attached to the first surface of the solid support. Each of the dendron typically comprises a central atom; a functional group or a protected form of the functional group that is attached to the central atom optionally through a linker; and a base portion attached to the central atom and having a plurality of termini that are attached to the first surface of the solid support. As used herein, the term "central atom" refers to a focal point atom from which the branches emanate. For example, the central atom is represented in Formula I, below, as $Q^1$. The term "base portion" when referring to a dendron refers to a moiety comprising a plurality of branches emanating from the central atom. In some embodiments, the dendron can be described or schematically illustrated as being conically-shaped with the base portion of the cone being bound to the solid support surface.

The functional group (or moiety) refers to an atom or a group of atoms within a molecule that are responsible for the chemical reaction. Generally, a functional group comprises a heteroatom (such as halogen, oxygen, nitrogen, sulfur, phosphorous, etc.) or an unsaturation (e.g., carbon-carbon double or triple bond). Exemplary functional groups include, but are not limited to, acyl halides, alcohols, ketones, aldehydes, carbonates (including esters), carboxylates, carboxylic acids, ethers, hydroperoxides, peroxides, halides, olefins, alkynes, amides, amines, imines, imides, azides, azo, cyanates, isocyanates, nitrates, nitriles, nitrites, nitro, nitroso, phosphines, phosphodiesters, phosphonic acids, phosphonates, sulfides, thioethers, sulfones, sulfonic acids, sulfoxides, thiols, thiocyanates, disulfides, thioamides, thioesters, thioketones. Often functional group undergoes a nucleophilic reaction or an electrophilic reaction. In some embodiments, the functional group of the dendron is capable of participating in a nucleophilic reaction. As such, the functional group can be a nucleophile or an electrophile. Often the functional group is adapted for attaching a probe.

In one particular instance, the functional group is capable of forming a bond with the probe by a nucleophilic substitution reaction.

The functional group is used to attach a wide variety of probes, which can then be used to detect the presence of a corresponding ligand in a fluid medium. Typically, when the functional group is attached to a probe, the discrimination efficiency (e.g., the amount of target specific binding relative to non-specific binding) of the probe is at least about 50%, often at least about 70%, more often at least about 80%, and most often at least about 90%. In one particular embodiment, when the functional group is attached to an oligonucleotide probe of 15 nucleotides and an oligonucleotide target of 15 nucleotides in solution is used, the single nucleotide polymorphism (SNP) discrimination efficiency is at least about 80% (1:0.2), often at least about 90% (1:0.1), more often at least about 95% (1:0.05), and more often at least 99% (1:0.01).

The discrimination efficiency of the probe can be determined by any of the variety of methods, for example, by comparing the efficiency and/or selectivity of the probe-ligand complex formation under substantially a similar reaction condition. SNP discrimination efficiency can also be determined in a similar fashion. One exemplary method of measuring the discrimination efficiency is to compare the signal strength of the target-specific probe bound to the substrate surface with that of target-nonspecific probe bound to the substrate. For example, if a target-specific probe bound to the substrate surface produces a signal strength of 100 at 10 nM target concentration and the target-nonspecific probe bound to the substrate surface produces a signal strength of 30 at the same target concentration, then the discrimination efficiency of the probe on the substrate surface is (100−30)/100 or 70% (1:0.3).

In some embodiments, when the functional group is attached to an oligonucleotide probe of 15-21 nucleotides, the signal strength of target-nonspecific oligonucleotide probe (e.g., an oligonucleotide probe having at least one, often at least two, and more often at least three different nucleotide from a target-specific oligonucleotide probe) bound to the substrate is reduced by at least about 70%, often by at least about 80%, more often by at least about 95%, and still more often by at least about 99% compared to the signal strength of the target-specific oligonucleotide probe (e.g., an oligonucleotide probe perfectly complementary to total or part of a target DNA) bound to the substrate. Generally, different oligonucleotide probes may have different discrimination efficiency. Thus, in one particular embodiment of the invention, the discrimination efficiency is measured using the DNA microarray assay with model system, and/or assaying codon 175 of p53 gene with a p53 DNA microarray as disclosed in the Examples section.

In other embodiments, when the functional group is attached to an oligonucleotide probe of 15 nucleotides, the relative amount of non-specific binding to the amount of specific binding is reduced by at least about 50%, often at least about 60%, more often at least 80%, and still more often at least about 90% compared to the oligonucleotide probe attached to a non-dendron. Again, one method of measuring the non-specific binding is those described herein including those in the Examples section. One particular method of determining reduction of the relative amount of non-specific binding is given by the following formula:

[(A−B)/A]×100% where A is the relative amount of non-specific binding using a non-dendron molecule (e.g., APDES-modified surface, see Table 2 in the Examples section, and B is the relative amount of non-specific binding using a dendron modified surface according to the invention (see, Table 2). For example, as can be seen in Table 2 (entries 1 and 4) of the Examples section, the relative amount of non-specific binding to the amount of the specific binding for C:T mismatch is reduced by at least 95% [(0.12−0.006)/0.12×100%=95%].

Yet in other embodiments, the functional group or the optional linker that is attached to the apex of the dendron does not form an α-helix. Without being bound by any theory, it is believed that the presence of an α-helix reduces the discrimination efficiency and/or increases the non-specific binding, thereby reducing the usefulness of the dendron.

In some aspects of the invention, the dendron is of the formula:

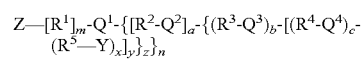

$$Z-[R^1]_m-Q^1-\{[R^2-Q^2]_a-\{(R^3-Q^3)_b-[(R^4-Q^4)_c-(R^5-Y)_x]_y\}_z\}_n \qquad I$$

where
each of m, a, b, and c is independently 0 or 1;
x is 1 when c is 0 or when c is 1, x is an integer from 1 to the oxidation state of $Q^4$-1;
y is 1 when b is 0 or when b is 1, y is an integer from 1 to the oxidation state of $Q^3$-1;
z is 1 when a is 0 or when a is 1, z is an integer from 1 to the oxidation state of $Q^2$-1;
n is an integer from 1 to the oxidation state of $Q^1$-1;
$Q^1$ is a central atom having the oxidation state of at least 3;
each of $Q^2$, $Q^3$ and $Q^4$ is independently a branch atom having the oxidation state of at least 3;
each of $R^1$, $R^2$, $R^3$, $R^4$, and $R^5$ is independently a linker;
Z is the functional group that is optionally protected; and
each of Y is independently a functional group on the terminus of said base portion,
wherein a plurality of Y are attached to said first surface of said solid support, provided the product of n, x, y, and z is at least 3.

It should be appreciated that when a, b or c is 1 and the corresponding z, y or x is less than the oxidation state of $Q^2$-1, $Q^3$-1 or $Q^4$-1, respectively, the remaining atoms attached to $Q^2$, $Q^3$, or $Q^4$, respectively, is hydrogen. As used herein, "Q" refers to any one of or all of $Q^1$, $Q^2$, $Q^3$, $Q^4$. Typically, Q is any atom in group IVA or VA of the periodic table. Exemplary atoms for Q include, but are not limited to, N, P, C, Si, Ge, and the like. Often, Q is N, P, C, or Si.

As can be seen in Formula I, Z is attached to the central atom optionally through a linker $R^1$. Often a is 1 such that Z is attached to the central atom through a linker $R^1$. Moreover, Z or its unprotected form (i.e., when Z is a protected functional group) is adapted for attaching a probe. In some embodiments, Z is a nucleophile. A nucleophile is an atom or a group of atoms that forms a chemical bond with its reaction partner (i.e., the electrophile) by donating both bonding electrons. Typically, the nucleophile is a heteroatom such as N, P, O, and S, or a carbanion particularly a carbanion that is stabilized by resonance and/or by the presence of nearby electron withdrawing group(s). One skilled in the art of organic chemistry can readily recognize suitable nucleophiles for the dendron of Formula I. Some of the representative nucleophiles are disclosed above in exemplary functional groups.

In other embodiments, Z is an electrophile. An electrophile is an atom or a group of atoms that are attracted to electrons and participates in a chemical reaction by accepting an electron pair in order to bond to a nucleophile. Most electrophiles are positively charged, have an atom which carries a partial positive charge, or have an atom which does not have an octet of electrons. Typically, the electrophile is a carbon atom that has at least a positive dipole moment due to one or more electronegative atoms (e.g., halides or other heteroatoms) that are attached to or are near the electrophilic center. One skilled in the art of organic chemistry can readily recognize suitable electrophiles for the dendron of Formula I. Some of the representative electrophiles are disclosed above in exemplary functional groups.

Yet in other embodiments, Z comprises a heteroatom selected from the group consisting of N, O, S, P, and a combination thereof.

Each Y can be independently a function group. That is, each Y can be independent of the other Y group. Often, however, all of the Y's are the same functional group. However, in general Z and Y are different functional groups. In some instances, Z and Y can be the same functional group, but one or the other is in a protected form. Such differences in functional group and/or the presence of a protecting group allow one to distinguish the reactivity of Z and Y, thereby allowing one to attach the dendron to the solid support via a plurality of Y's and allows attachment of a probe on Z.

Figure 1:
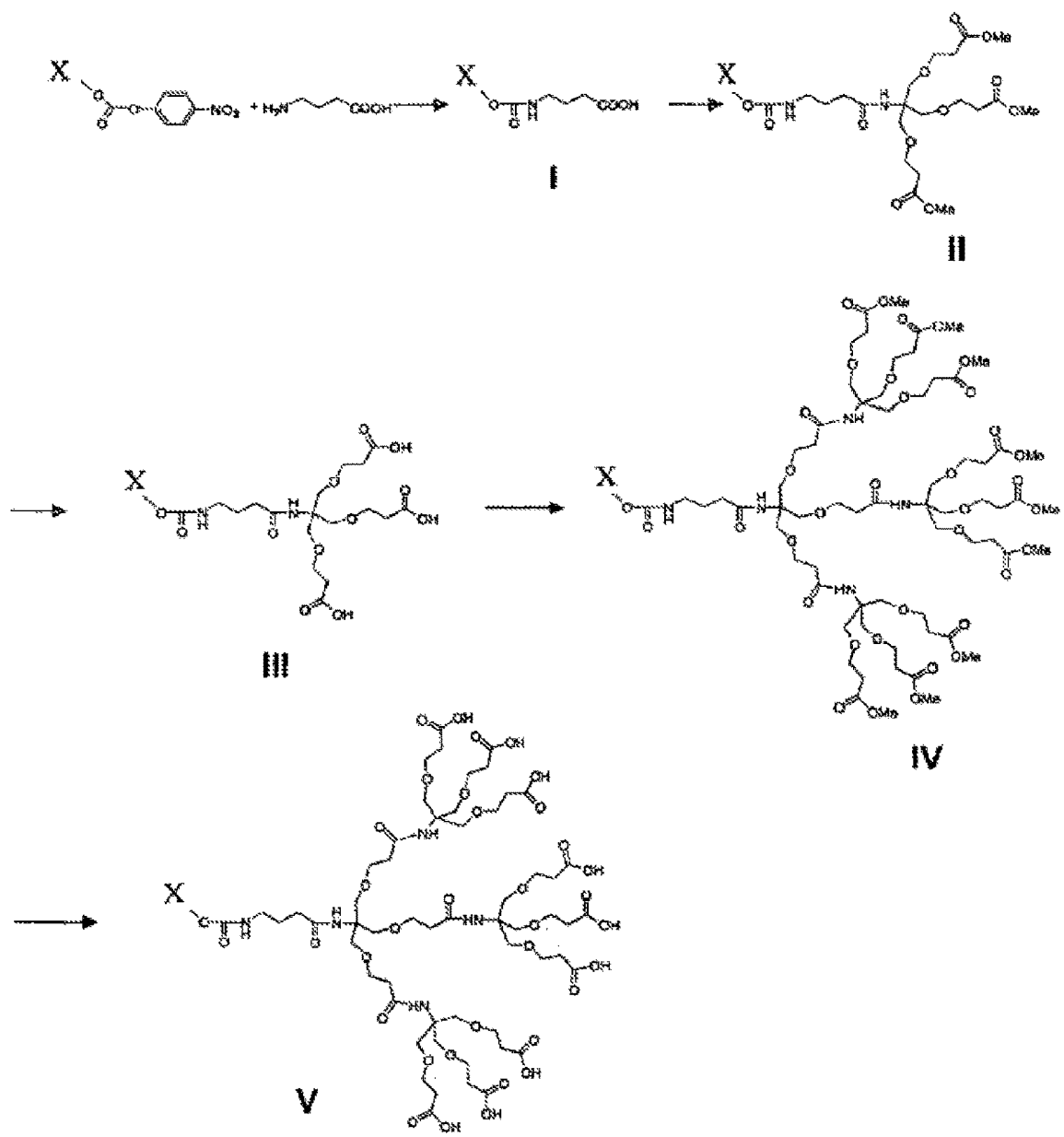
FIG. 1 is a reaction scheme for producing a dendron.

FIG. 1 is a synthetic scheme illustrating one method for synthesizing a dendron. A wide variety of starting materials can be used to produce a vast number of intermediate compounds and dendrons. In FIG. 1, X can be hydrogen, a protecting group, including anthracenemethyl (A), Boc, Fmoc, Ns, etc., or any other suitable group. Some of the details of synthesizing various dendrons can be found throughout this disclosure including the Examples section.

Linker

Referring again to Formula I, the dendron generally comprises various linkers, e.g., $R^1$, $R^2$, $R^3$, $R^4$, $R^5$. Each linker is connected to another linker by a branch atom $Q^2$, $Q^3$, or $Q^4$. The terminal linker comprises functional group Y so that it is capable of binding to the solid support.

The length of each of the linker may be determined by a variety of factors, including the number of branched functional groups binding to the solid support, strength of the binding to the solid support, spacing desired, etc. Therefore, it is understood that the linker is not to be limited to any particular type of chain or polymer of any particular length. However, as a general guideline, the length of the linker may be from about 0.5 nm to about 20 nm, typically from about 0.5 nm to about 10 nm, and often from about 0.5 nm to about 5 nm. Alternatively, each linker is independently a chain having from about 1 to about 100 atoms, typically from about 1 to about 50 atoms, often from about 1 to about 25 atoms, and more often about 3 atoms to about 10 atoms in chain length. The chemical construct of the linker include without limitation, a linear or branched organic moiety, such as but not limited to substituted or unsubstituted alkyl, alkenyl, alkynyl, cycloalkyl, cycloalkenyl, aryl, ether, polyether, ester, aminoalkyl, polyalkenylglycol and so on.

Linkers $R^1$, $R^2$, $R^3$, $R^4$, $R^5$ can be the same or different. Typically, each linker is a repeating unit, a linear or branched organic moiety. However, it is also understood that not all the linkers need to be the same repeating unit. Nor do all valence positions for a linker need be filled with a repeating unit. For example, all of the $R^2$ can be the same repeating units. Or one or two of the $R^2$ may be a repeating unit, and the remaining $R^2$'s may be H or other chemical entities. Likewise, one or two of each of $R^3$, $R^4$, or $R^5$ may be, independently, a repeating unit, H or any other chemical entity. Thus, a variety of shapes of polymers may be made in this way. Accordingly, it is possible that a dendron can have from about 3 to about 81 Y functional groups. Typically, the dendron has from about 6 to about 81 Y functional groups, from about 6 to about 54 Y functional groups, from about 6 to about 27 Y functional groups, from about 8 to about 27 Y functional groups, from about 9 to about 27 Y functional groups, from about 9 to about 18 Y functional groups, or from about 9 to about 12 Y functional groups.

Functional Group Y

Each of functional group Y is sufficiently reactive to undergo addition or substitution reactions. The functional group (or moiety) refers to an atom or a group of atoms within a molecule that are responsible for the chemical reaction. Generally, a functional group comprises a heteroatom (such as halogen, oxygen, nitrogen, sulfur, phosphorous, etc.) or an unsaturation (e.g., carbon-carbon double or triple bond). Exemplary functional groups include, but are not limited to, acyl halides, hydroxy, ketones, aldehydes, carbonates (including esters), carboxylates, carboxylic acids, urea, ethers, hydroperoxides, peroxides, oxiranyl, halides, olefins, alkynes, amides, amines, imines, imides, azides, aziridinyl, azo, cyanates, isocyanates, nitrates, nitriles, nitrites, nitro, nitroso, oxazolinyl, imidazolinyl, phosphines, phosphodiesters, phosphonic acids, phosphonates, sulfides, thioethers, sulfones, sulfonic acids, sulfoxides, thiols, thiocyanates, isothiocyanantes, disulfides, thioamides, thioesters, thioketones, silanyl, as well as other groups that are known to undergo a chemical reaction. Often functional group undergoes a nucleophilic reaction or an electrophilic reaction.

Protecting Group

When present, the choice of protecting group depends on numerous factors. Therefore, the invention is not limited to any particular protecting group so long as it serves the function of preventing the reaction of the functional group to another chemical entity, and that it is capable of being removed under desired specified conditions. Typically, the protecting group used can be removed relatively easily.

Exemplary suitable protecting groups include without limitation the following:

Amino acid protecting groups: Methyl, Formyl, Ethyl, Acetyl, t-Butyl, Anisyl, Benzyl, Trifluoroacetyl, N-hydroxysuccinimide, t-Butyloxycarbonyl, Benzoyl, 4-Methylbenzyl, Thioanizyl, Thiocresyl, Benzyloxymethyl, 4-Nitrophenyl, Benzyloxycarbonyl, 2-Nitrobenzoyl, 2-Nitrophenylsulphenyl, 4-Toluenesulphonyl, Pentafluorophenyl, Diphenylmethyl (Dpm), 2-Chlorobenzyloxycarbonyl, 2,4,5-trichlorophenyl, 2-bromobenzyloxycarbonyl, 9-Fluorenylmethyloxycarbonyl, Triphenylmethyl, 2,2,5,7,8-pentamethyl-chroman-6-sulphonyl, Phthaloyl, 3-Nitrophthaloyl, 4,5-dichlorophthaloyl, tetrabromophthaloyl, and tetrachlorophthaloyl.

Hydroxy protecting groups: p-Anisyloxymethyl (p-AOM), Benzyloxymethyl (BOM), t-Butoxymethyl, 2-Chlorotetrahydrofuran (THF), Guaiacolmethyl (GUM), (1R)-Menthoxymethyl (MM), p-Methoxybenzyloxymethyl (PMBM), metoxyethoxymethyl (MEM), Methoxymethyl (MOM), o-Nitrobenzyloxymethyl, (Phenyldimethylsilyl)methoxymethyl (SMOM), and 2-(Trimethylsilyl)ethoxymethyl (SEM).

DNA, RNA protecting reagent: 2'-OMe-Ac-C-CE Phosphoramidite, 2'-OMe-Ac-RNA CPG, 2'-OMe-1-CE Phosphoramidite, 2'-OMe-5-Me-C-CE Phosphoramidite, Ac-C-CE Phosphoramidite, Ac-C-RNA 500, dmf-dG-CE Phosphoramidite, dmf-dG-CPG 500, and 2-Amino-dA-CE Phosphoramidite.

Other suitable protecting groups for various functional groups are well known to one skilled in the art. See, for example, T. W. Greene and P. G. M. Wuts, *Protective Groups in Organic Synthesis*, $3^{rd}$ edition, John Wiley & Sons, New York, 1999, and Harrison and Harrison et al., *Compendium of Synthetic Organic Methods*, Vols. 1-8 (John Wiley and Sons, 1971-1996)

Table 1 below lists various types of exemplified compounds. However, it is to be understood that variations in X, $R^1$, Q, R and Y are encompassed by the present invention.

TABLE 1

Representative and Exemplified Macromolecule Compounds

| Cpd No. | X | R$^1$ | Q | R | Y |
|---|---|---|---|---|---|
| 3-1 | A | NH—(CH$_2$)$_3$C(O)NH | C | CH$_2$O(CH$_2$)$_2$C(O) | OH |
| 3-2 | A | NH—(CH$_2$)$_3$C(O)NH | C | CH$_2$O(CH$_2$)$_2$C(O) | OMe |
| 3-3 | Boc | NH—(CH$_2$)$_3$C(O)NH | C | CH$_2$O(CH$_2$)$_2$C(O) | OH |
| 3-4 | Boc | NH—(CH$_2$)$_3$C(O)NH | C | CH$_2$O(CH$_2$)$_2$C(O) | OMe |
| 3-5 | A | NH—(CH$_2$CH$_2$O)$_2$CH$_2$C(O)NH | C | CH$_2$O(CH$_2$)$_2$C(O) | OH |
| 3-6 | A | NH—(CH$_2$CH$_2$O)$_2$CH$_2$C(O)NH | C | CH$_2$O(CH$_2$)$_2$C(O) | OMe |
| 6-1 | A | NH—(CH$_2$)$_3$C(O)NH | C | CH$_2$O(CH$_2$)$_2$C(O) | OH |
| 6-2 | Boc | NH-(cyclohexyl)(CO)CH$_2$ | C | (CH$_2$)$_2$-(cyclohexyl)-C(O) | NH$_2$ |
| 6-3 | Boc | NH—(CH$_2$CH$_2$O)$_2$CH$_2$C(O)NH | C | CH$_2$O(CH$_2$)$_2$C(O) | OH |
| 6-4 | Fmoc | NH—(CH$_2$)$_6$NHC(O)NH | C | CH$_2$—C≡C—CH$_2$C(O) | OH |
| 6-5 | Fmoc | NH—(CH$_2$)$_7$C(O)O | C | CH$_2$—C≡C—CH$_2$C(O) | OMe |
| 6-6 | NS | NH-(cyclohexyl)(CO)O | C | CH$_2$O(CH$_2$)$_2$C(O) | NH$_2$ |
| 6-7 | NS | NH—(CH$_2$)$_6$NHC(O)NH | C | (CH2)$_7$ | NH$_2$ |
| 8-1 | A | NH—(CH$_2$)$_3$C(O)NH | C | CH$_2$O(CH$_2$)$_2$C(O) | OH |
| 8-2 | Boc | NH—(CH$_2$)$_7$C(O)NH | C | (CH2)$_2$C(O) | OH |
| 8-3 | NS | NH—(CH$_2$)$_6$(CO)NH | C | (CH2)$_2$-(cyclohexyl)-C(O) | OH |
| 8-4 | Fmoc | NH—(CH$_2$)$_6$(CO)O | C | CH$_2$—C≡C—CH$_2$C(O) | NH$_2$ |
| 8-5 | Fmoc | NH—(CH$_2$)$_6$NH(CO)O | C | (CH2)$_2$-(cyclohexyl)-C(O) | OH |
| 8-6 | NS | NH-(cyclohexyl)(CO)O | C | CH$_2$OCH(CH$_3$)CH$_2$C(O) | NH$_2$ |
| 8-7 | Boc | NH-(cyclopropyl)(CO)O | C | CH$_2$—C≡C—CH$_2$C(O) | NH$_2$ |
| 9-1 | A | NH—(CH$_2$)$_3$C(O)NH | C | CH$_2$O(CH$_2$)$_2$C(O) | OH |
| 9-2 | A | NH—(CH$_2$)$_3$C(O)NH | C | CH$_2$O(CH$_2$)$_2$C(O) | OMe |
| 9-3 | A | NH—(CH$_2$CH$_2$O)$_2$CH$_2$C(O)NH | C | CH$_2$O(CH$_2$)$_2$C(O) | OH |
| 9-4 | A | NH—(CH$_2$CH$_2$O)$_2$CH$_2$C(O)NH | C | CH$_2$O(CH$_2$)$_2$C(O) | OMe |
| 9-5 | Fmoc | NH—(CH$_2$)$_6$C(O)NH | C | CH$_2$O(CH$_2$)$_2$C(O) | OH |
| 9-6 | Fmoc | NH—(CH$_2$)$_6$C(O)NH | C | CH$_2$O(CH$_2$)$_2$C(O) | OMe |
| 9-7 | Boc | NH—(CH$_2$)$_3$C(O)NH | C | CH$_2$O(CH$_2$)$_2$C(O) | OH |
| 9-8 | Boc | NH—(CH$_2$)$_3$C(O)NH | C | CH$_2$O(CH$_2$)$_2$C(O) | OMe |
| 9-9 | Ns | NH—(CH$_2$)$_3$C(O)NH | C | CH$_2$O(CH$_2$)$_2$C(O) | OH |
| 9-10 | Ns | NH—(CH$_2$)$_3$C(O)NH | C | CH$_2$O(CH$_2$)$_2$C(O) | OMe |
| 9-11 | A | NH—(CH$_2$)$_6$NHC(O)CH$_2$CH$_2$ | C | (CH2)$_7$ | OBzl |
| 12-1 | A | NH—(CH$_2$)$_3$C(O)NH | C | CH$_2$O(CH$_2$)$_2$C(O) | OH |
| 12-2 | Fmoc | NH—(CH$_2$)$_6$NHC(O)NH | C | (CH2)$_2$-(cyclohexyl)-C(O) | NH$_2$ |
| 12-3 | Boc | NH-(cyclohexyl)(CO)O | C | CH$_2$—C≡C—CH$_2$C(O) | OMe |
| 12-4 | Boc | NH—(CH$_2$)$_5$NH | C | CH$_2$OCH(CH$_3$)CH$_2$C(O) | NH$_2$ |
| 12-5 | NS | NH-(cyclopropyl)(CO)CH$_2$ | C | (CH2)$_2$ | NH$_2$ |
| 12-6 | NS | NH—(CH$_2$)$_6$C(O)O | C | CH$_2$OCH$_2$CH(CH$_3$)C(O) | NH$_2$ |
| 12-7 | Fmoc | NH—(CH$_2$)$_6$NHC(O)O | C | CH$_2$OCH(CH$_3$)CH$_2$C(O) | NH$_2$ |
| 16-1 | Boc | NH—(CH$_2$)$_3$C(O)NH | C | CH$_2$O(CH$_2$)$_2$C(O) | NH$_2$ |
| 16-2 | Boc | NH-(cyclohexyl)(CO)CH$_2$ | C | (CH2)$_2$-(cyclohexyl)-C(O) | OH |
| 16-3 | Fmoc | NH—(CH$_2$CH$_2$O)$_2$CH$_2$C(O)O | C | CH$_2$O(CH$_2$)$_2$C(O) | OH |
| 16-4 | Fmoc | NH—(CH$_2$)$_6$NHC(O)NH | C | (CH2)$_2$-(cyclohexyl)-C(O) | NH$_2$ |
| 16-5 | NS | NH-(cyclohexyl)(CO)NH | C | CH$_2$—C≡C—CH$_2$C(O) | OH |
| 16-6 | NS | NH-(cyclopropyl)(CO)CH$_2$ | C | CH$_2$O(CH$_2$)$_2$C(O) | OMe |
| 16-7 | A | NH-(cyclopropyl)(CO)CH$_2$ | C | CH$_2$OCH(CH$_3$)CH$_2$C(O) | OH |
| 16-8 | A | NH-(cyclopropyl)(CO)CH$_2$ | C | CH$_2$OCH(CH$_3$)CH$_2$C(O) | NH$_2$ |
| 16-9 | A | NH—(CH$_2$)$_5$O | C | CH$_2$OCH$_2$CH(CH$_3$)C(O) | OH |
| 18-1 | A | NH—(CH$_2$)$_3$C(O)NH | C | CH$_2$O(CH$_2$)$_2$C(O) | OH |
| 18-2 | Fmoc | NH-(cyclohexyl)(CO)O | C | CH$_2$OCH(CH$_3$)CH$_2$C(O) | NH$_2$ |
| 18-3 | Boc | NH-(cyclopropyl)(CO)O | C | CH$_2$OCH$_2$CH(CH$_3$)C(O) | NH$_2$ |
| 18-4 | Fmoc | NH—(CH$_2$)$_6$NHC(O)CH$_2$NH | C | (CH2)$_2$-(cyclohexyl)-C(O) | OH |
| 18-5 | NS | NH—(CH$_2$)$_6$NHC(O)CH$_2$ | C | CH$_2$—C≡C—CH$_2$C(O) | OMe |
| 18-6 | Boc | NH—(CH$_2$)$_5$O | C | CH$_2$OCH$_2$CH(CH$_3$)C(O) | NH$_2$ |
| 27-1 | A | NH—(CH$_2$)$_3$C(O)NH | C | CH$_2$O(CH$_2$)$_2$C(O) | OH |
| 27-2 | A | NH—(CH$_2$)$_6$NHC(O)CH$_2$CH$_2$ | C | (CH2)$_7$ | OH |
| 27-3 | Fmoc | NH—(CH$_2$CH$_2$O)$_2$CH$_2$C(O)O | C | (CH2)$_2$-(cyclohexyl)-C(O) | NH$_2$ |
| 27-4 | NS | NH-(cyclopropyl)(CO)NH | C | (CH2)$_2$-(cyclohexyl)-C(O) | NH$_2$ |
| 27-5 | Boc | NH-(cyclohexyl)(CO)CH$_2$ | C | CH$_2$OCH(CH$_3$)CH$_2$C(O) | OMe |
| 27-6 | Fmoc | NH—(CH$_2$)$_5$O | C | CH$_2$OCH$_2$CH(CH$_3$)C(O) | NH$_2$ |

In some aspects of the invention, the solid support is a non-porous solid substrate. Suitable non-porous solid substrates include, but not limited to, metals, metal alloys, ceramics, plastics, silicon, and silicates (such as glass and semi-conductor wafer). The solid support can be in the form of a slide, particle, bead, or micro-well. In some embodiments, the solid support is a non-porous solid substrate. Within these embodiments, in some instances the solid support is glass.

In other aspects of the invention, the solid support is a porous solid substrate. Exemplary porous materials include, but are not limited to, a membrane, bead (including controlled pore bead), gelatin, and hydrogel.

Another aspect of the invention provides a method for producing a solid support comprising a plurality of dendrons on its surface. The solid support comprises at least a first surface comprising a surface functional group for forming a bond with a dendron. The dendron comprises a central atom; a functional group that is attached to the central atom optionally through a linker; and a base portion attached to the central atom and having a plurality of termini, where each terminus of the base portion comprises a functional group. The method generally involves contacting a plurality of dendrons with the solid support surface under conditions sufficient to form a bond between the surface functional group on the first surface of the solid support and the functional group on the terminus of the base such that a plurality of bonds are formed between the base portion of the dendron and the first surface of the solid support.

In some embodiments, the bond that formed between the surface functional group on the first surface of the solid support and the functional group on the terminus of the base is a covalent bond.

Yet in other embodiments, the bond between the surface functional group on the first surface of the solid support and the functional group on the terminus of the base is formed by a nucleophilic substitution reaction. Reaction conditions for a suitable nucleophilic substitution reaction are well known to one skilled in the art. See, for example, Harrison and Harrison et al., *Compendium of Synthetic Organic Methods*, Vols. 1-8 (John Wiley and Sons, 1971-1996).

A variety of solid supports can be used in methods of the invention. Suitable solid supports are discussed herein and include non-porous as well as porous solid supports. Exemplary solid supports that can be used include those given above. In some embodiments, the solid support is a non-porous solid support. Within these embodiments, in some instances, the solid support is a non-porous solid support. In one particular embodiments, the non-porous solid support is a glass.

In some embodiments, the functional group that is attached to the central atom optionally through a linker is protected prior to attaching the dendron to the solid support surface to reduce or prevent its reactivity. In this manner, the functional group attached to the central atom (or the one that is present on the apex of the dendron) remains relatively inert under the reaction conditions while the functional group on the terminus of the base undergoes bond forming reaction with the surface functional group on the solid support. Use of a protecting group to reduce or prevent reactivity of a particular functional group is well known to one of ordinary skill in the art. See, for example, T. W. Greene and P. G. M. Wuts, *Protective Groups in Organic Synthesis*, 3$^{rd}$ edition, John Wiley & Sons, New York, 1999, and Harrison and Harrison et al., *Compendium of Synthetic Organic Methods*, Vols. 1-8 (John Wiley and Sons, 1971-1996), which are incorporated herein by reference in their entirety. Representative hydroxy protecting groups include acyl groups, benzyl and trityl ethers, tetrahydropyranyl ethers, trialkylsilyl ethers and allyl ethers. Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like. It should be appreciated, however, that in some instances the reactivity of the functional group on the base terminus and the reactivity of the functional that is attached to the central atom optionally through a linker (i.e., "apex functional group") is sufficiently different enough to allow attachment of the dendrons onto the solid substrate surface without the need to protect the apex functional group.

Once the dendron is attached to the solid support, the protecting group, if present, can be removed from the apex functional group. A desired probe can then be attached to the apex functional group using a suitable reaction condition.

In some embodiments, the dendrons are attached to predefined regions of the solid support. Such attachments can be achieved using any of the variety of methods known to one skilled in the art, for example, by using a wet or dry coating technology.

Other aspects of the invention provide methods for detecting a presence of a ligand in a fluid medium using a solid support that comprises an array of dendrons on its surface. The base portion of the dendron is attached to the solid support and the apex functional group comprises a probe that is selective for a given ligand. The method generally involves contacting the fluid medium with the solid substrate under conditions sufficient to selectively form a probe-ligand complex if the ligand is present in the fluid medium; and determining the presence of the desired probe-ligand complex. The presence of the desired probe-ligand complex is an indication that the fluid medium comprises the ligand.

In some embodiments, the desired probe-ligand complex is an oligonucleotide-complementary oligo- or polynucleotide complex, an oligopeptide-binding oligo- or polypeptide complex, PNA-complementary oligo- or polynucleotide complex, LNA-complementary oligo- or polynucleotide complex, or a receptor-substrate complex. Within these embodiments, in some instances the receptor-substrate complex comprises a drug-drug receptor complex, an enzyme-enzyme substrate complex, an antibody-antigen complex, or an aptamer-protein complex.

In some embodiments, methods of the invention are capable of discriminating a single nucleotide polymorphism in the oligonucleotide probe-complementary DNA complex, herein the oligonucleotide probe having at least about 75 nucleotide sequences, often having at least about 50 nucleotide sequences, more often having at least about 30 nucleotide sequences, and most often having at least about 15. One method of determining such selectivity is to analyze a DNA microarray with model system and/or codon 175 of the seven hot spots in p53 gene as disclosed in the Examples section.

Still in some embodiments, methods of the invention are capable of discriminating a single amino acid mismatch in the oligopeptide probe-specific peptide target complex, herein the oligopeptide probe having at least about 200 amino acids, often having at least about 50 amino acids, and more often having at least about 20 amino acids, and most often having at least about 10 amino acids.

The distance between the probes among the plurality of dendrons on the solid support can range from about 0.1 nm to about 100 nm, typically from about 1 nm to about 100 nm, often from about 2 nm to about 50 nm, more often from about 2 nm to about 30 nm, and most often about 2 nm to about 10 nm.

Target-Specific Ligand or Probe

The target-specific ligand, also known as the probe, which is to be attached to the polymer includes a variety of compounds, including chemicals, biochemicals, bioactive compounds and so on. In this regard, the probe can be a nucleic acid, an oligonucleotide, RNA, DNA, PNA, LNA, aptamer, antigen, antibody, etc. The oligonucleotide can be a naturally occurring nucleic acid or an analog thereof. Thus, the probe can be a polypeptide composed of naturally occurring amino acids or synthetic amino acids. The probe can be a combination of nucleic acid, amino acid, carbohydrate or any other chemical so long as it is capable of being attached to the functional group of the polymer. In particular, the probe can also be a chemical, such as based on a triazine backbone, which can be used as a component in a combinatorial chemistry library, in particular, a triazine tagged library.

Solid Support

The solid support can be any solid material to which the polymer can be attached. Typically, the polymer binds to the solid support surface through either covalent or ionic bond. The solid support can be functionalized so that bonding occurs with the functional group that is present on the base portion of the polymer. The surface of the solid support can be a variety of surfaces according to the needs of the practitioner in the art. If a microarry or biochip format is desired then typically oxidized silicon wafer, fused silica or glass can be the substrate. In some embodiments, the solid support is a glass slide. Other exemplary solid support includes membrane filters such as but not limited to nitrocellulose or nylon. The solid support can be hydrophilic or polar, and can possess negative or positive charge before or after coating.

Controlled Pore Glass Bead

Natural polymers such as dextran and agarose are the most frequently used chromatography supports for affinity chromatography. Sepharose 6B, 4B, and 2B are chromatographic materials composed of cross-linked agarose, which exhibit extremely low nonspecific adsorption. In spite of their wide use, agarose gel, typically in a bead shape, suffers some drawbacks. For instance, the flow (or elution) rates are moderate due to their soft nature, they cannot be dried or frozen since they shrink severely and essentially irreversibly, and they do not tolerate some organic solvents. In comparison, controlled pore glass (CPG) exhibits many exceptional properties for the support: it is mechanically stable; it has a fixed three dimensional structure; it does not swell or shrink upon change of environment; it is chemically stable from pH 1 to pH 14; it is inert to a broad range of nucleophilic and electrophilic reagents; it is stable against heating; it exhibits excellent flow (or elution) properties; and it shows less tendency to adhere to surface of containers. In addition, after a modification step, removal of reagents and byproducts through washing is rapid and efficient. All of these characteristics are useful in many fields such as permeation chromatography, solid phase synthesis, affinity purification, etc.

Pore Size

Effective porosity of CPG toward an adsorbed dendron is determined by the accessibility of the dendron to the CPG surface. To a first approximation, the accessibility of CPG to a dendron depends on geometric factors, which are related to the relative size of the pores of the CPG compared to the size of the dendron. If a dendron has a molecular size that is larger than the pore openings leading to the internal surface, adsorption and interactions can only occur with the external surface. From these considerations, it is apparent that the extent and strength of adsorption of a dendron onto CPG depends on a variety of parameters including, but not limited to, pore size of CPG, the total surface area of CPG, and the chemical composition of accessible surface of CPG.

Modification of Glutathione CPG

One of the concerns of affinity matrices is degree of nonspecific binding (or NSB). It is considered to be a ubiquitous problem in affinity purification and solid-phase synthesis. In general, some of the key factors to suppress nonspecific binding are to avoid the hydrogen bond donor groups and increase the hydrophilicity of matrices. CPG surface, even when modified with an aminoalkyl group, is polar and retains partial negative charge. In some embodiments of the invention, 1,4-butanediol diglycidyl ether (or BUDGE) is used as a linker to attach the dendron onto the solid support surface (e.g., leading to samples E1 and E3). Without being bound by any theory, it is believed that some of the advantages of incorporating BUDGE are inclusion of ethereal bond that is stable against hydrolysis, enhanced flexibility due to its relatively long length, relatively a long distance from the CPG surface, and reduction of nonspecific binding. Use of a linker to attach dendron to a solid support surface provides flexibility of the bound probe (e.g., GSH).

Figure 3:
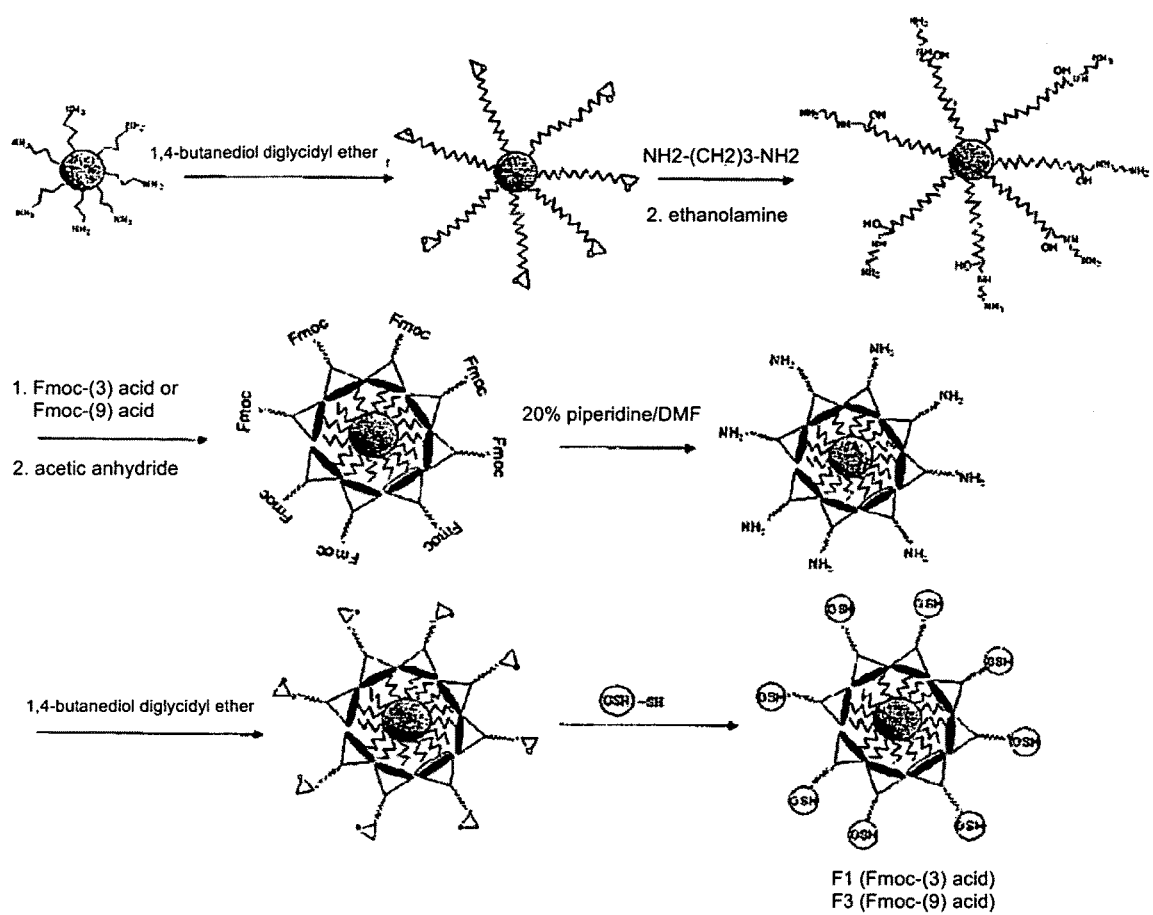
FIG. 3 shows a schematic presentation of sample E1 (Fmoc-(3)acid) and E3 (Fmoc-(9)acid) preparation with the dendron on AMPCPG matrices and the incorporation of glutathione.

FIG. 3 shows a schematic summary of attaching a dendron onto a solid support surface. Typically, dendrons comprising a carboxylic acid functional group on the base termini are attached to a solid support surface using EDC and NHS. After dendrons are attached to the solid support surface, acetic anhydride used to cap unreacted amino functional groups on the solid support surface. The Fmoc protecting group is then removed using piperidine to release a free amino group on the apex of the dendron. The dendron is reacted with BUDGE to increase the length of the linker (i.e., $R^1$). GSH is then attached to the dendron by reacting the thiol group of GSH and the epoxide group of the dendron.

Microarray

In order to improve the performance of microarrays, various issues such as probe design, reaction conditions during spotting, hybridization and washing conditions, suppression of non-specific binding, distance between the biomolecules and the surface, and/or the space between the immobilized biomolecules should be considered. Because most of these factors are associated with the nature of the microarray surface, surface optimization has become one of the major goals in microarray research. Some aspects of the present invention provide solid supports comprising surface bound dendrons. In some embodiments, the dendrons are cone-shaped and provide oligonucleotide microarrays with single nucleotide polymorphism (or SNP) discrimination efficiency close to the solution value (1:0.01), reduce nonspecific binding, or both.

Figure 2:
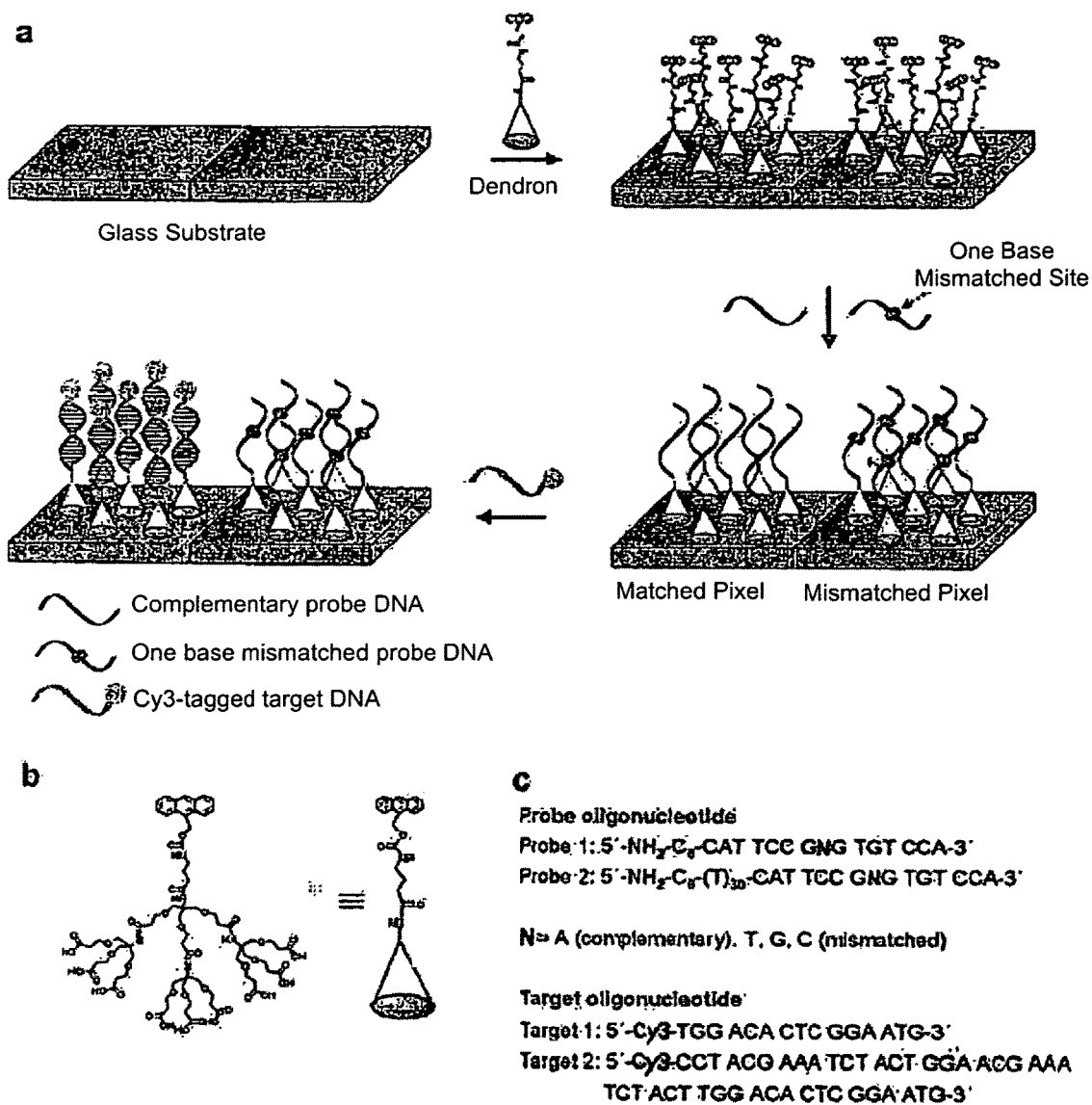
FIGS. 2a-2c show detection of a dendron-modified solid support surface.

FIG. 2a illustrates one method for attaching dendrons of FIG. 2b and selectively hybridizing a fluorophore-tagged target oligonucleotide (see FIG. 2c) with a matched oligonucleotide probe while discriminating a single base mismatched pair on the dendron-modified glass surface. In some embodiments, the dendron was modified as shown in FIG. 3b to facilitate deprotection and increase the reactivity of the resulting apex amine functional group. The present inventors have found that a covalent bond between the dendron's carboxylic acid groups and the surface hydroxyl groups provides enhanced thermal stability relative to attaching a dendron to a solid support surface via an ionic interaction. The present inventors have also found that in some instances an oligoethereal interlayer (i.e., polyether linker) significantly reduces non-specific oligonucleotide binding.

The surface of a solid support can be prepared using any of the various methods known to one skilled in the art. For example, hydroxylated glass surface can be prepared by using a method disclosed by Maskis et al. in *Nucleic Acids Res.*, 1992, 20, 1679-1684. Solid supports including oxidized silicon wafer, fused silica, and glass slide can be modified with (3-glycidoxypropyl)methyldiethoxysilane (GPDES) and ethylene glycol (EG). Typically, the dendron was attached to the solid support surface using a coupling reaction between the apex functional group of the dendron (e.g., carboxylic acid group) and the functional group on the solid support surface (e.g., hydroxyl group), for example, by using 1-[3-(dimethylamino)propyl]-3-ethylcarbodiimide hydrochloride (EDC) or 1,3-dicyclohexylcarbodiimide (DCC) in the presence of 4-dimethylaminopyridine (DMAP).

Referring again to FIGS. 2a-2c, in some instances, the increase in thickness after attaching the dendron was 11±12 Å, which is comparable to the ionic bonding. After the immobilization, a UV absorption peak arising from the anthracene moiety of the dendron was observed at 257 nm. The molecular layer was stable enough to show no change in terms of thickness and absorption characteristics upon stirring in dimethylformamide for 1 d. The topographical images obtained by tapping mode atomic force microscope (AFM) also showed that the resulting layer was very smooth and substantially homogeneous without any significant aggregates or holes. It should be appreciated that FIGS. 2a-2c are only illustrative in forming a solid support surface bound dendrons. The present invention is not limited to this technique. In fact, any conventionally known methods for attaching a compound on a solid support surface can be used to produce microarrays of the invention.

In some embodiments, preparation of oligonucleotide microarrays includes deprotecting the apex functional group. It should be appreciated that such step is only necessary if the apex functional group is in a protected form. In cases where the apex functional group is not protected, such step is not necessary. Referring again to FIGS. 2a-2c, the immobilized dendron was activated (i.e., deprotected) to generate a primary amine group. The amine group was activated by reacting with di(N-succinimidyl)carbonate (DSC) and the probe oligonucleotides were attached by spotting 50 mM sodium bicarbonate buffer (10% dimethylsulfoxide (DMSO), pH 8.5) solution of the appropriate amine-tethered oligonucleotide (20 μM) using a Microsys 5100 Microarrayer (Cartesian Technologies, Inc.). Conventionally, for solid supports with a reactive amine surface group, a thiol-tethered oligonucleotide and a heterobifunctional linker such as succinimidyl 4-maleimido butyrate (SMB) or sulphosuccinimidyl-4-(N-maleimidomethyl)cyclohexane-1-carboxylate (SSMCC) are employed. In contrast, some embodiments of the invention use linkers such as DSC, which allows spotting of amine-tethered oligonucleotides. Thus, some of the advantages of methods and compositions of the invention is the cost effectiveness and avoiding using easily oxidized thiol-tethered oligonucleotide. It should be appreciated, however, that thiol-tethered oligonucleotides can be useful under certain conditions.

Additional objects, advantages, and novel features of this invention will become apparent to those skilled in the art upon examination of the following examples thereof, which are not intended to be limiting.

EXAMPLES

Synthesis of Dendrons
Preparation of 9-anthrylmethyl N-(3-carboxylpropyl)carbamate To a solution of 4-Aminobutyric acid (0.50 g, 4.8 mmol, 1.0 equiv) and triethylamine (TEA) (1.0 ml, 7.3 mmol, 1.5 equiv) in N,N-dimethylformamide (DMF) at 50° C. was added 9-anthrylmethyl p-nitrophenyl carbonate (1.81 g, 4.8 mmol, 1.0 equiv). After stirring at 50° C. for 2 h, the solution was evaporated to dryness, and the solution was basified with 0.50 N sodium hydroxide solution. The aqueous solution was washed with ethyl acetate (EA), stirred in an ice bath and acidified with dilute hydrochloric acid (HCl). After the product was extracted with EA, the organic solution was dried with anhydrous $MgSO_4$, filtered and concentrated to yield 1.06 g (65% yield) of a yellow powder.

$^1$H NMR ($CDCl_3$): δ 11.00-9.00 (br, $CH_2COOH$, 1H), 8.41 (s, $C_{14}H_9CH_2$, 1H), 8.31 (d, $C_{14}H_9CH_2$, 2H), 7.97 (d, $C_{14}H_9CH_2$, 2H), 7.51 (t, $C_{14}H_9CH_2$, 2H), 7.46 (t, $C_{14}H_9CH_2$, 2H), 6.08 (s, $C_{14}H_9CH_2O$, 2H), 5.01 (t, $OCONHCH_2$, 1H), 3.23 (q, $NHCH_2CH_2$, 2H), 2.34 (t, $CH_2CH_2COOH$, 2H), 1.77 (m, $CH_2CH_2CH_2$, 2H).

$^{13}$C NMR ($CDCl_3$): δ 178.5 ($CH_2COOH$), 157.9 (OCONH), 132.1 ($C_{14}H_9CH_2$), 131.7 ($C_{14}H_9CH_2$), 129.7 ($C_{14}H_9CH_2$), 129.7 ($C_{14}H_9CH_2$), 127.3 ($C_{14}H_9CH_2$), 126.8 ($C_{14}H_9CH_2$), 125.8 ($C_{14}H_9CH_2$), 124.6 ($C_{14}H_9CH_2$), 60.2 ($C_{14}H_9CH_2$), 41.0 ($NHCH_2CH_2$), 31.7 ($CH_2CH_2COOH$), 25.6 ($CH_2CH_2CH_2$).

Preparation of A-[3]-ester (9-anthrylmethyl N-{[(tris{[2-(methoxycarbonyl)ethoxy]methyl}methyl)amino]carbonyl}propylcarbonate)

To a room temperature solution of 9-anthrylmethyl N-(3-carboxylpropyl)carbamate (0.65 g, 1.93 mmol, 1.5 equiv), 1-[3-(dimethylamino)propyl]-3-ethylcarbodiimide hydrochloride (EDC) (0.37 g, 1.93 mmol, 1.5 equiv), and 1-hydroxybenzotriazole hydrate (HOBT) (0.261 g, 1.93 mmol, 1.5 equiv) in acetonitrile was added a solution of tris {[(methoxycarbonyl)ethoxy]methyl}aminomethane (0.49 g, 1.29 mmol, 1.0 equiv) in acetonitrile. After 12 h at room temperature, the reaction mixture was concentrated and the crude product was dissolved in EA and washed with 1.0 N HCl and saturated sodium bicarbonate solution. The organic layers were combined, dried over $MgSO_4$, filtered, concentrated, and purified by column chromatography (eluent:ethyl acetate:hexane=5:1 (v/v)) to yield 0.67 g (74% yield) of a viscous yellow liquid.

$^1$H NMR ($CDCl_3$): δ 8.43 (s, $C_{14}H_9CH_2$, 1H), 8.36 (d, $C_{14}H_9CH_2$, 2H), 7.99 (d, $C_{14}H_9CH_2$, 2H), 7.53 (t, $C_{14}H_9CH_2$, 2H), 7.47 (t, $C_{14}H_9CH_2$, 2H), 6.15 (s, CONHC, 1H), 6.08 (s, $C_{14}H_9CH_2O$, 2H), 5.44 (t, $OCONHCH_2$, 1H), 3.63-3.55 (m, $CH_2OCH_2CH_2COOCH_3$, 21H), 3.27 (q, $NHCH_2CH_2$, 2H), 2.46 (t, $CH_2CH_2COOCH_3$, 6H), 2.46 (t, $CH_2CH_2CONH$, 2H), 1.81 (m, $CH_2CH_2CH_2$, 2H).

$^{13}$C NMR ($CDCl_3$): δ173.2 ($CH_2CONH$), 172.7 ($CH_2COOCH_3$), 157.4 (OCONH), 132.9 ($C_{14}H_9CH_2$), 131.5 ($C_{14}H_9CH_2$), 129.5 ($C_{14}H_9CH_2$), 129.4 ($C_{14}H_9CH_2$), 127.5 ($C_{14}H_9CH_2$), 127.0 ($C_{14}H_9CH_2$), 125.6 ($C_{14}H_9CH_2$), 124.7 ($C_{14}H_9CH_2$), 69.6 ($NHCCH_2O$), 67.2 ($C_{14}H_9CH_2$), 60.1 ($OCH_2CH_2$), 59.4 ($NHCCH_2$), 52.1 ($OCH_3$), 40.8 ($NHCH_2CH_2$), 35.1 ($OCH_2CH_2$), 34.7 ($CH_2CH_2CONH$), 26.3 ($CH_2CH_2CH_2$).

Anal. Calcd for $C_{36}H_{46}N_2O_{12} \cdot 0.5H_2O$: C, 61.18; H, 6.65; N, 4.03. Found: C, 61.09, H, 6.69, N, 3.96.

Preparation of A-[3]-acid (9-anthrylmethyl N—[({tris[(2-carboxyethoxy)methyl]methyl}amino) carbonyl]propylcarbamate)

A mixture of 9-anthrylmethyl N-{[(tris{[2-(methoxycarbonyl)ethoxy]methyl}methyl)amino]carbonyl}propyl carbonate (0.67 g, 0.93 mmol) and 0.20 N NaOH (30 ml, 6 mmol) in acetone (30 ml) was stirred at room temperature for 1 d, after which acetone was evaporated. The aqueous solution was washed with EA, stirred in an ice bath and acidified with dilute HCl. The resulting aqueous solution was extracted with EA. The combined organic layers were dried with anhydrous $MgSO_4$, filtered and concentrated. Solidification in acetone and ether solution at −20° C. and filtration gave 0.54 g (88% yield) of a pale yellow powder.

$^1$H NMR ($CDCl_3$): δ 11.00-9.00 (br, $CH_2COOH$, 3H), 8.61 (s, $C_{14}H_9CH_2$, 1H), 8.47 (d, $C_{14}H_9CH_2$, 2H), 8.11 (d, $C_{14}H_9CH_2$, 2H), 7.60 (t, $C_{14}H_9CH_2$, 2H), 7.52 (t, $C_{14}H_9CH_2$, 2H), 6.63 (s, CONHC, 1H), 6.36 (t, OCON-

HCH$_2$, 1H), 6.12 (s, C$_{14}$H$_9$CH$_2$, 2H). 3.40-363 (m, CH$_2$OCH$_2$CH$_2$COOH, 12H), 3.20 (q, NHCH$_2$CH$_2$, 2H), 2.52 (t, CH$_2$CH$_2$COOH, 6H), 2.17 (t, CH$_2$CH$_2$CONH, 2H), 1.75 (m, CH$_2$CH$_2$CH$_2$, 2H).

$^{13}$C NMR (CDCl$_3$): δ 172.2 (CH$_2$COOH), 172.0 (CH$_2$CONH), 156.7 (OCONH), 131.2 (C$_{14}$H$_9$CH$_2$), 130.7 (C$_{14}$H$_9$CH$_2$), 128.6 (C$_{14}$H$_9$CH$_2$), 128.4 (C$_{14}$H$_9$CH$_2$), 127.3 (C$_{14}$H$_9$CH$_2$), 126.2 (C$_{14}$H$_9$CH$_2$), 124.8 (C$_{14}$H$_9$CH$_2$), 124.0 (C$_{14}$H$_9$CH$_2$), 68.6 (NHCCH$_2$O), 66.5 (C$_{14}$H$_9$CH$_2$), 59.5 (OCH$_2$CH$_2$), 58.0 (NHCCH$_2$), 40.0 (NHCH$_2$CH$_2$), 34.0 (OCH$_2$CH$_2$), 33.5 (CH$_2$CH$_2$CONH), 25.8 (CH$_2$CH$_2$CH$_2$).

Anal. Calcd for C$_{33}$H$_{40}$N$_2$O$_{12}$.1.5H$_2$O: C, 57.97; H, 6.34; N, 4.10. Found: C, 57.89; H, 6.21; N, 4.09.

Preparation of A-[9]-ester (9-anthrylmethyl N—[({tris[(2-{[(tris{[2-(methoxycarbonyl)ethoxy]methyl}(methyl)amino]carbonyl}ethoxy)methyl]methyl}amino)carbonyl]propylcarbamate)

To a solution of 9-anthrylmethyl N-[({tris[(2-carboxyethoxy)methyl]methyl}amino)carbonyl]propylcarbamate (0.54 g, 0.82 mmol, 1.0 equiv), EDC (0.55 g, 2.87 mmol, 3.5 equiv), and HOBT (0.39 g, 2.89 mmol, 3.5 equiv) in acetonitrile at room temperature was added a solution of tris{[(methoxycarbonyl)ethoxy]methyl}aminomethane (0.96 g, 2.53 mmol, 3.1 equiv) in acetonitrile. After stirring at room temperature for 36 h, acetonitrile was evaporated. The crude product was dissolved in EA and washed with 1.0 N HCl and saturated sodium bicarbonate solution. The organic layer was dried over anhydrous MgSO$_4$, filtered, concentrated, and purified by chromatography (eluent:ethyl acetate:methanol=20:1 (v/v)) to yield 1.26 g (88% yield) of a viscous yellow liquid.

$^1$H NMR (CDCl$_3$): δ 8.47 (s, C$_{14}$H$_9$CH$_2$, 1H), 8.39 (d, C$_{14}$H$_9$CH$_2$, 2H), 8.02 (d, C$_{14}$H$_9$CH$_2$, 2H), 7.53 (t, C$_{14}$H$_9$CH$_2$, 2H), 7.47 (t, C$_{14}$H$_9$CH$_2$, 2H), 6.60 (s, CH$_2$CH$_2$CH$_2$CONHC, 1H), 6.13 (s, OCH$_2$CH$_2$CONHC, 3H), 6.11 (s, C$_{14}$H$_9$CH$_2$O, 2H), 5.79 (t, OCONHCH$_2$, 1H), 3.65-3.60 (m, CH$_2$OCH$_2$CH$_2$CONH, CH$_2$OCH$_2$CH$_2$COOCH$_3$, 75H), 3.29 (q, NHCH$_2$CH$_2$, 2H), 2.50 (t, CH$_2$CH$_2$COOCH$_3$, 18H), 2.36 (t, OCH$_2$CH$_2$CONH, 6H), 2.27 (t, CH$_2$CH$_2$CH$_2$CONH, 2H), 1.85 (m, CH$_2$CH$_2$CH$_2$, 2H).

$^{13}$C NMR (CDCl$_3$): δ 173.3 (OCH$_2$CH$_2$CONH), 172.5 (CH$_2$CH$_2$CH$_2$CONH), 171.6 (CH$_2$COOCH$_3$), 157.2 (OCONH), 131.8 (C$_{14}$H$_9$CH$_2$), 131.5 (C$_{14}$H$_9$CH$_2$), 129.4 (C$_{14}$H$_9$CH$_2$), 129.3 (C$_{14}$H$_9$CH$_2$), 127.6 (C$_{14}$H$_9$CH$_2$), 127.0 (C$_{14}$H$_9$CH$_2$), 125.6 (C$_{14}$H$_9$CH$_2$), 124.7 (C$_{14}$H$_9$CH$_2$), 69.5 (NHCCH$_2$OCH$_2$CH$_2$COOCH$_3$), 67.9 (NHCCH$_2$OCH$_2$CH$_2$CONH), 67.2 (C$_{14}$H$_9$CH$_2$), 60.3 (OCH$_2$CH$_2$CONH), 60.2 (OCH$_2$CH$_2$COOCH$_3$), 59.2 (NHCCH$_2$OCH$_2$CH$_2$COOCH$_3$, NHCCH$_2$OCH$_2$CH$_2$CONH), 52.1 (OCH$_3$), 41.0 (NHCH$_2$CH$_2$), 37.6 (OCH$_2$CH$_2$CONH), 35.1 (OCH$_2$CH$_2$COOCH$_3$), 34.7 (CH$_2$CH$_2$CH$_2$CONH), 26.3 (CH$_2$CH$_2$CH$_2$).

Anal. Calcd for C$_{81}$H$_{121}$N$_5$O$_{36}$.H$_2$O: C, 55.31; H, 7.05; N, 3.98. Found: C, 55.05; H, 7.08; N, 4.04.

MALDI-TOF-MS: 1763.2 (MNa+), 1779.2 (MK+).

Preparation of A-[9]-acid (9-anthrylmethyl N-({[tris({2-[({tris[(2-carboxyethoxy)methyl]methyl}amino)carbonyl]ethoxy}methyl)methyl]amino}carbonyl)propylcarbamate)

A mixture of 9-anthrylmethyl N-[({tris(2-{[(tris {[2-(methoxycarbonyl)ethoxy]methyl}methyl)amino]carbonyl}ethoxy)methyl]methyl}amino)carbonyl]propylcarbamate (0.60 g, 0.34 mmol) in acetone (30 ml) and 0.20 N NaOH (30 ml) was stirred at room temperature for 1 d, after which acetone was removed. The aqueous solution was washed with EA, stirred in an ice bath, acidified with dilute HCl, and extracted with EA. The organic layer was dried with MgSO$_4$, filtered, and concentrated to yield 0.37 g (68% yield) of a yellow powder.

$^1$H NMR (DMSO): δ 13.00-11.00 (br, CH$_2$COOH, 9H), 8.66 (s, C$_{14}$H$_9$CH$_2$, 1H), 8.42 (d, C$_{14}$H$_9$CH$_2$, 2H), 8.13 (d, C$_{14}$H$_9$CH$_2$, 2H), 7.62 (t, C$_{14}$H$_9$CH$_2$, 2H), 7.54 (t, C$_{14}$H$_9$CH$_2$, 2H), 7.12 (t, OCONHCH$_2$, 1H), 7.10 (s, OCH$_2$CH$_2$CONHC, 3H), 7.06 (s, CH$_2$CH$_2$CH$_2$CONHC, 1H), 6.06 (s, C$_{14}$H$_9$CH$_2$O, 2H), 3.57-3.55 (m, CH$_2$OCH$_2$CH$_2$CONH, CH$_2$OCH$_2$CH$_2$COOH, 48H), 3.02 (q, NHCH$_2$CH$_2$, 2H), 2.42 (t, CH$_2$CH$_2$COOH, 18H), 2.32 (t, OCH$_2$CH$_2$CONH, 6H), 2.11 (t, CH$_2$CH$_2$CONH, 2H), 1.60 (m, CH$_2$CH$_2$CH$_2$, 2H).

$^{13}$C NMR (DMSO): δ 172.8 (CH$_2$COOH), 172.2 (CH$_2$CH$_2$CH$_2$CONH), 170.5 (OCH$_2$CH$_2$CONH), 156.5 (OCONH), 131.0 (C$_4$H$_9$CH$_2$), 130.6 (C$_{14}$H$_9$CH$_2$), 129.0 (C$_{14}$H$_9$CH$_2$), 128.7 (C$_{14}$H$_9$CH$_2$), 127.6 (C$_{14}$H$_9$CH$_2$), 126.7 (C$_{14}$H$_9$CH$_2$), 125.4 (C$_{14}$H$_9$CH$_2$), 124.3 (C$_{14}$H$_9$CH$_2$), 68.3 (NHCCH$_2$OCH$_2$CH$_2$COOH), 67.4 (NHCCH$_2$OCH$_2$CH$_2$CONH), 66.8 (C$_{14}$H$_9$CH$_2$), 59.8 (OCH$_2$CH$_2$COOH), 59.6 (OCH$_2$CH$_2$CONH), 57.9 (NHCCH$_2$OCH$_2$CH$_2$CONH), 55.9 (NHCCH$_2$OCH$_2$CH$_2$COOH), 36.4 (NHCH$_2$CH$_2$), 34.6 (OCH$_2$CH$_2$COOH), 30.8 (OCH$_2$CH$_2$CONH), 29.7 (CH$_2$CH$_2$CH$_2$CONH), 25.9 (CH$_2$CH$_2$CH$_2$).

Preparation of A-[27]-ester (9-anthrylmethyl-3-({[tris({[(1-{tris[(2-{[(tris{[2-(methoxycarbonyl)ethoxy]methyl}methyl)amino]carbonyl}ethoxy)methyl]methyl}amino)carbonyl]-2-ethoxy}methyl)methyl]amino}carbonyl)propylcarbamate)

The A-[9]-acid (0.5 g, 0.31 mM, 1.0 equiv), 1-[3-(dimethylamino)propyl]-3-ethylcarbodiimide hydrochloride (EDC, 0.59 g, 3.1 mM, 10 equiv) and 1-hydroxybenzotriazole hydrate (HOBT, 0.42 g, 3.1 mM, 10 equiv) were dissolved in methylene chloride and stirred at room temperature. Tris[((methoxycarbonyl)ethoxy)methyl]-aminomethane (1.1 g, 2.9 mM, 9.3 equiv) dissolved in methylene chloride was added with stirring. After stirring at room temperature for 36 h, the methylene chloride was evaporated. The crude product was dissolved in ethyl acetate (200 ml) and sequentially washed with 10% HCl, water, 10% aqueous Na$_2$CO$_3$, saturated aqueous NaHCO$_3$ and brine. After drying with anhydrous MgSO$_4$, filtered, and evaporated, viscous yellow liquid was dried under vacuum. The total weight of crude yellow liquid was 1.5 g, which was hydrolyzed without further purification.

Preparation of A-[27]-acid (9-anthrylmethyl-3-({[tris({[(1-{tris[(2-{[(tris{[2-carboxyethoxy]methyl}methyl)amino]carbonyl}ethoxy)methyl]methyl}amino)carbonyl]-2-ethoxy}methyl)methyl]amino}carbonyl)propylcarbamate)

The crude 9-anthrylmethyl-3-({[tris({[(1-{tris[(2-{[(tris{[2-(methoxycarbonyl)-ethoxy]methyl}methyl)amino]carbonyl}ethoxy)methyl]methyl}amino)carbonyl]-2-ethoxy}methyl)methyl]amino}carbonyl)propylcarbamate (or 27-ester, 1.5 g) obtained above was dissolved in acetone (75 ml) and 0.40 N NaOH (75 ml). After stirring at room temperature for 1 d, the acetone was evaporated. The aqueous solution was washed with ethyl acetate, stirred in an ice bath and acidified with aqueous 10% HCl. After the product was extracted with ethyl acetate, the organic solution was dried with anhydrous MgSO$_4$, filtered and evaporated. The total weight of final yellow powder was 1.1 g (Y=79%).

$^1$H NMR (DMSO-d$_6$): δ 13.00-11.00 (br, CH$_2$COOH, 27H), 8.67 (s, C$_{14}$H$_9$CH$_2$, 1H), 8.42 (d, C$_{14}$H$_9$CH$_2$, 2H), 8.14 (C$_{14}$H$_9$CH$_2$, 2H), 7.62 (t, C$_{14}$H$_9$CH$_2$, 2H), 7.54 (t, C$_{14}$H$_9$CH$_2$, 2H), 6.97 (t, OCONHCH$_2$, 1H), 6.85 (s, OCH$_2$CH$_2$CONHC, 3H), 6.82 (s, OCH$_2$CH$_2$CONHC, 9H), 6.80 (s, CH$_2$CH$_2$CH$_2$CONHC, 1H), 6.06 (s, C$_{14}$H$_9$CH$_2$O, 2H), 3.55 (m, CH$_2$OCH$_2$CH$_2$CONH, CH$_2$OCH$_2$CH$_2$COOH, 156H), 3.02 (q, NHCH$_2$CH$_2$, 2H), 2.42 (t, CH$_2$CH$_2$COOH, 54H), 2.32 (t, OCH$_2$CH$_2$CONH, 24H), 2.11 (t, CH$_2$CH$_2$CH$_2$CONH, 2H), 1.59 (m, CH$_2$CH$_2$CH$_2$, 2H)

$^{13}$C NNMR (DMSO-d$_6$): δ 172.6 (CH$_2$COOH), 170.4 (OCH$_2$CH$_2$CONH), 170.2 (CH$_2$CH$_2$CH$_2$CONH), 156.3 (OCONH), 130.9 (C$_{14}$H$_9$CH$_2$), 130.4 (C$_{14}$H$_9$CH$_2$), 128.8 (C$_{14}$H$_9$CH$_2$), 127.4 (C$_{14}$H$_9$CH$_2$), 126.6 (C$_{14}$H$_9$CH$_2$), 125.2 (C$_{14}$H$_9$CH$_2$), 124.9 (C$_{14}$H$_9$CH$_2$), 124.2 (C$_{14}$H$_9$CH$_2$), 68.2 (NHCCH$_2$OCH$_2$CH$_2$COOH), 67.3 (NHCCH$_2$OCH$_2$CH$_2$CONH), 67.0 (NHCCH$_2$OCH$_2$CH$_2$CONH), 66.6 (NHCCH$_2$OCH$_2$CH$_2$COOH), 59.6 (C$_{14}$H$_9$CH$_2$), 59.4 (NHCCH$_2$O), 36.3 (NHCH$_2$CH$_2$CH$_2$CONH), 34.5 (NHCCH$_2$OCH$_2$CH$_2$), 30.4 (NHCH$_2$CH$_2$CH$_2$CONH), 25.1 (CH$_2$CH$_2$CH$_2$)

Preparation of A-[81]-ester

To a solution of A-[27]-acid (0.5 g, 0.11 mM, 1 eq), 1-[3-(dimethylamino)-propyl]-3-ethylcarbodiimide hydrochloride (EDC, 0.64 g, 3.3 mM, 30 eq) and 1-hydroxybenzotriazole hydrate (HOBT, 0.45 g, 3.3 mM, 30 eq) dissolved in MC (15 ml), a solution of tris[((methoxycarbonyl)ethoxy)methyl]-aminomethane (1.26 g, 3.3 mM, 30 eq) in MC (10 ml) was added and stirred at RT for 36 h. At the end of this period, MC was evaporated; the residue obtained was dissolved in ethyl acetate (200 ml) and sequentially washed with 10% HCl (2×100 ml), water (100 ml), 10% aq. Na$_2$CO$_3$ (100 ml), saturated aq. NaHCO$_3$ (5×100 ml) and brine (100 ml). The organic phase was dried (anh. MgSO$_4$). Removal of solvent in vacuum gave a thick viscous residue (1.59 g, [crude compound yield]), which was hydrolyzed without further purification.

Preparation of A-[81]-Acid

The A-[81]-ester (1.5 g) obtained above was dissolved in a mixture of acetone (75 ml) and 0.4 N NaOH (75 ml) and stirred at RT. After completion of reaction (~30 h), acetone was evaporated and the aqueous solution was washed with ethyl acetate (2×50 ml), cooled in an ice bath and acidified with aqueous dilute HCl (10%); the product formed was extracted with ethyl acetate (6×100 ml). The combined organic layer was dried (anh. MgSO$_4$), filtered. To the filtrate toluene (50 ml) was added and evaporated to afford anthryl-81-acid (1.2 g, 82% when calculated from anthryl-27-acid).

Preparation of Fmoc-[9]-acid

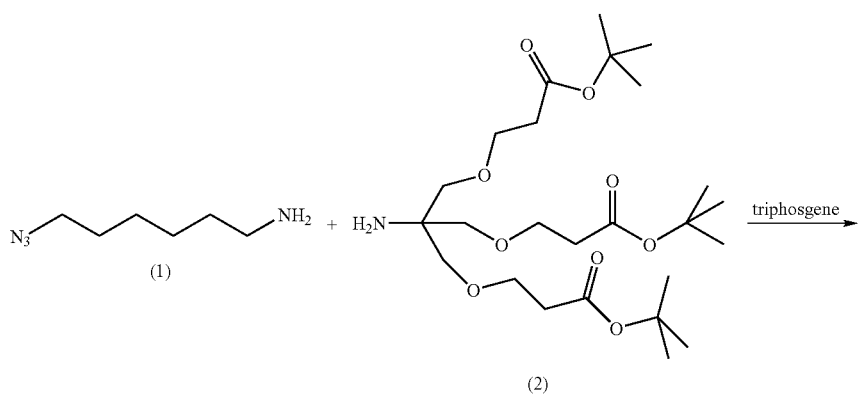

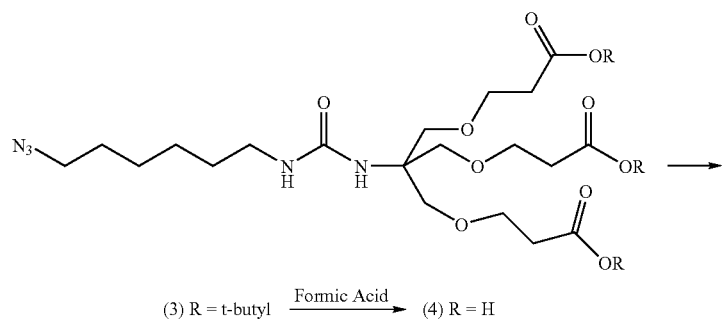

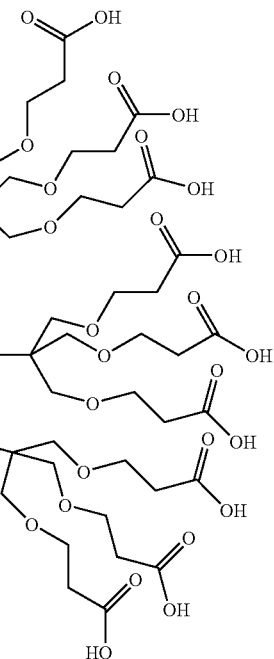

(5)

Triphosgene (1.3 g, 4.3 mmol) was dissolved in anhydrous $CH_2Cl_2$ (20 mL). A mixture of 6-azidohexylamine (1) (1.6 g, 12 mmol) and N,N-diisopropylethylamine (DIEA, 2.4 mL, 13.8 mmol) in anhydrous $CH_2Cl_2$ (35 mL) was added dropwise to the stirred solution of triphosgene over a period of 7 h using a syringe pump. After further stirring for 2 h, a solution of (2) (6.4 g, 13 mmol) and DIEA (2.7 mL, 15.2 mmol) in anhydrous $CH_2Cl_2$ (20 mL) was added. The reaction mixture was stirred for 4 h at room temperature under nitrogen, and washed with 0.5 M HCl and brine. The organic layer was then dried over anhydrous $MgSO_4$, and the solvent was removed. Purification with column chromatography (silica, 1:1 EtOAc/hexane) yielded colorless oil (3.0 g, 40%).

$^1$H NMR ($CDCl_3$, 300 MHz): δ 1.45 (s, $(CH_3)_3C$, 27H); 1.36-1.58 (m, $CH_2CH_2CH_2CH_2$, 8H); 2.46 (t, $CH_2CH_2O$, J=6.4 Hz, 6H), 3.13 (m, $CONHCH_2$, 2H), 3.26 (t, $N_3CH_2$, J=6.9 Hz, 2H), 3.64-3.76 (m, $CCH_2O$ and $CH_2CH_2O$, 12H); 5.00 (t, $CH_2NHCO$, J=6.7 Hz, 1H), 5.29 (s, CONHC, 1H).

$^{13}$C NMR ($CDCl_3$, 75 MHz): δ 26.52, 26.54, 28.81, 30.26 ($CH_2CH_2CH_2CH_2$); 28.14 (($CH_3)_3C$); 36.20 ($CH_2CH_2O$); 39.86 ($CONHCH_2$); 51.40 ($N_3CH_2$); 58.81 ($CCH_2O$); 67.16 ($CH_2CH_2O$); 69.23 ($CCH_2O$); 80.58 (($CH_3)_3C$); 157.96 (NHCONH); 171.26 (COOt-Bu).

FAB-MS: 674.26 (M$^+$).

$N_3$-spacer-[3]ester (3) (0.36 g, 0.56 mmol) was stirred in 6.6 mL of 96% formic acid for 24 h. The formic acid was then removed at reduced pressure at 50° C. to produce compound (4) as a colorless oil in a quantitative yield.

$^1$H NMR ($CD_3COCD_3$, 300 MHz): δ 1.34-1.60 (m, $CH_2CH_2CH_2CH_2$, 8H); 2.53 (t, $CH_2CH_2O$, J=6.4 Hz, 6H), 3.07 (t, $CONHCH_2$, J=6.9 Hz, 2H), 3.32 (t, $N_3CH_2$, J=6.9 Hz, 2H), 3.67-3.73 (m, $CCH_2O$ and $CH_2CH_2O$, 12H).

$^{13}$C NMR ($CD_3COCD_3$, 75 MHz): δ 27.21, 29.54, 31.02 ($CH_2CH_2CH_2CH_2$); 35.42 ($CH_2CH_2O$); 40.27 ($CONHCH_2$); 52.00 ($N_3CH_2$); 59.74 ($CCH_2O$); 67.85 ($CH_2CH_2O$); 70.96 ($CCH_2O$); 158.96 (NHCONH); 173.42 (COOH).

FAB-MS: 506.19 (MH$^+$).

The HOBt (0.20 g, 1.5 mmol), DIEA (0.30 mL, 1.8 mmol), and EDC (0.33 g, 1.8 mmol) were added to (4) (0.25 g, 0.50 mmol) in 5.0 mL of dry acetonitrile. Then, the amine (2) (1.14 g, 2.3 mmol) dissolved in 2.5 mL of dry acetonitrile was added, and the reaction mixture was stirred under $N_2$ for 48 h. After removal of the solvent at reduced pressure, the residue was dissolved in MC and washed with 0.5 M HCl and brine. The organic layer was then dried over $MgSO_4$, the solvent was removed in vacuo, and column chromatography (SiO2, 2:1 EtOAc/hexane) yielded an azido nona-tert-butyl ester as a colorless oil (0.67 g, 70%).

$^1$H NMR ($CDCl_3$, 300 MHz): δ 1.45 (s, $(CH_3)_3C$, 81H); 1.36-1.58 (m, $CH_2CH_2CH_2CH_2$, 8H); 2.40-2.47 (m, $CH_2CH_2O$ gen. 1 & 2, 24H), 3.13 (m, $CONHCH_2$, 2H), 3.26 (t, $N_3CH_2$, 6.9 Hz, 2H), 3.62-3.69 (m, $CCH_2O$ gen. 1 & 2, $CH_2CH_2O$ gen. 1 & 2, 48H); 5.36 (t, $CH_2NHCO$, J=6.7 Hz, 1H), 5.68 (br, CONHC, 1H), 6.28 (br, amide NH, 3H).

$^{13}$C NMR ($CDCl_3$, 75 MHz): δ 26.59, 26.69, 28.91, 30.54 ($CH_2CH_2CH_2CH_2$); 28.22 (($CH_3)_3C$); 36.20 ($CH_2CH_2O$ gen. 2); 37.43 ($CH_2CH_2O$ gen. 1); 39.81 ($CONHCH_2$); 51.47 ($N_3CH_2$); 58.93 ($CCH_2O$ gen. 1); 59.89 ($CCH_2O$ gen. 2); 67.15 ($CH_2CH_2O$ gen. 2); 67.68 ($CH_2CH_2O$ gen. 1); 69.23 ($CCH_2O$ gen. 2); 70.12 ($CCH_2O$ gen. 1); 80.57 (($CH_3)_3C$); 158.25 (NHCONH); 171.01 (COOt-Bu) 171.41 (CONH amides).

MALDI-MS: 1989.8 (MNa$^+$), 2005.8 (MK$^+$).

The azido nona-tert-butyl ester (0.37 g, 0.20 mmol) was stirred with 10% Pd/C (37.0 mg) in ethanol (20.0 mL) under $H_2$ at room temperature for 12 h, filtered, and concentrated to yield an amino nona-tert-butyl ester as a colorless oil. This compound (0.33 g, 0.17 mmol) and DIEA (33 μL, 0.19 mmol) were dissolved in 5.0 mL of $CH_2Cl_2$, and stirred for 30 min under nitrogen atmosphere. 9-Fluorenylmethyl chloroformate (48 mg, 0.19 mmol) in 2.0 mL of $CH_2Cl_2$ was added, and the reaction mixture was stirred for 3 h at room temperature. The solvent was removed under reduced pressure and washed with 0.5 M HCl and brine. The residue was purified with column chromatography (silica, EtOAc) to yield a Fmoc-protested ester as a colorless oil (0.18 g, 64%).

$^1$H NMR (CDCl$_3$, 300 MHz): δ 1.45 (s, (CH$_3$)$_3$C, 81H); 1.23-1.58 (m, CH$_2$CH$_2$CH$_2$CH$_2$, 8H); 2.37-2.47 (m, CH$_2$CH$_2$O gen. 1 & 2, 24H); 3.10-3.22 (m, CONHCH$_2$, 4H); 3.62-3.70 (m, CCH$_2$O gen. 1 & 2, CH$_2$CH$_2$O gen. 1 & 2, 48H); 4.22 (t, CH(fluorenyl)-CH$_2$, J=7.1 Hz, 1H); 4.36 (d, fluorenyl-CH$_2$, J=7.1 Hz, 2H); 5.27-5.35 (m, CH$_2$NHCO, 2H); 5.67 (br, CONHC, 1H); 6.25 (br, amide, 3H); 7.28-7.77 (fluorenyl, 8H).

$^{13}$C NMR (CDCl$_3$, 75 MHz): δ 26.85, 27.02, 30.27, 30.88 (CH$_2$CH$_2$CH$_2$CH$_2$); 28.49 ((CH$_3$)$_3$C); 36.48 (CH$_2$CH$_2$O gen. 2); 37.73 (CH$_2$CH$_2$O gen. 1); 40.03, 41.34 (CONHCH$_2$); 47.68 (CH(fluorenyl)-CH$_2$); 59.22 (CCH$_2$O gen. 1); 60.16 (CCH$_2$O gen. 2); 66.87 (fluorenyl-CH$_2$); 67.43 (CH$_2$CH$_2$O gen. 2); 67.98 (CH$_2$CH$_2$O gen. 1); 69.52 (CCH$_2$O gen. 2); 70.42 (CCH$_2$O gen. 1); 80.84 ((CH$_3$)$_3$C); 120.28, 125.52, 127.38, 127.98, 141.65, 144.48 (fluorenyl); 156.88 (OCONH); 158.52 (NHCONH); 171.27 (COOt-Bu) 171.65 (amide CONH).

MALDI-MS: 2186.8 (MNa$^+$), 2002.8 (MK$^+$).

The Fmoc-protested ester (0.12 g, 72 mmol) was stirred in 10 mL of 96% formic acid for 18 h. The formic acid was then removed at reduced pressure at 50° C. to produce compound (5) as a colorless oil in a quantitative yield.

$^1$H NMR (CD$_3$COCD$_3$, 300 MHz): δ 1.23-1.51 (m, CH$_2$CH$_2$CH$_2$CH$_2$, 8H); 2.44-2.58 (m, CH$_2$CH$_2$O gen. 1 & 2, 24H); 3.15-3.18 (m, CONHCH$_2$, 4H); 3.61-3.75 (m, CCH$_2$O gen. 1 & 2, CH$_2$CH$_2$O gen. 1 & 2, 48H); 4.23 (t, CH(fluorenyl)-CH$_2$, J=7.0 Hz, 1H); 4.35 (d, fluorenyl-CH$_2$, J=7.0 Hz, 2H); 5.85, 6.09 (br, CH$_2$NHCO, 2H); 6.57 (br, CONHC, 1H); 6.88 (br, amide NH, 3H); 7.31-7.88 (fluorenyl, 8H).

$^{13}$C NMR (CD$_3$COCD$_3$, 75 MHz): δ 27.21, 27.33, 30.69, 30.98 (CH$_2$CH$_2$CH$_2$CH$_2$); 35.31 (CH$_2$CH$_2$O gen. 2); 37.83 (CH$_2$CH$_2$O gen. 1); 40.56, 41.54 (CONHCH$_2$); 48.10 (CH(fluorenyl)-CH$_2$); 59.93 (CCH$_2$O gen. 1); 61.10 (CCH$_2$O gen. 2); 66.86 (fluorenyl-CH$_2$); 67.81 (CH$_2$CH$_2$O gen. 2); 68.37 (CH$_2$CH$_2$O gen. 1); 69.80 (CCH$_2$O gen. 2); 70.83 (CCH$_2$O gen. 1); 120.84, 126.13, 127.98, 128.56, 142.10, 145.16 (fluorenyl); 157.50 (OCONH); 159.82 (NHCONH); 173.20 (amide CONH); 173.93 (COOH).

Other Dendrons

Some of the other representative dendrons that were prepared are shown below. It should be appreciated, however, that while a particular protecting group may be shown with a macromolecule, the compounds are not limited to the specific protecting groups shown. Moreover, while various chains and spacers are depicted indicating an exact molecular structure, modifications are possible according to accepted chemical modification methods to achieve the function of a density controlled, typically a low density, array on a substrate surface. As a point of reference for the short-hand description of the compounds, the left most letter(s) indicates the protecting group; the numeral in brackets indicates the number of branched termini; and the right most chemical entity indicates the chemistry on the branched termini. For example, "A-[27]-acid" indicates anthrylmethyl protecting group; 27 termini, and acid groups at the termini.

A-[27]-acid:

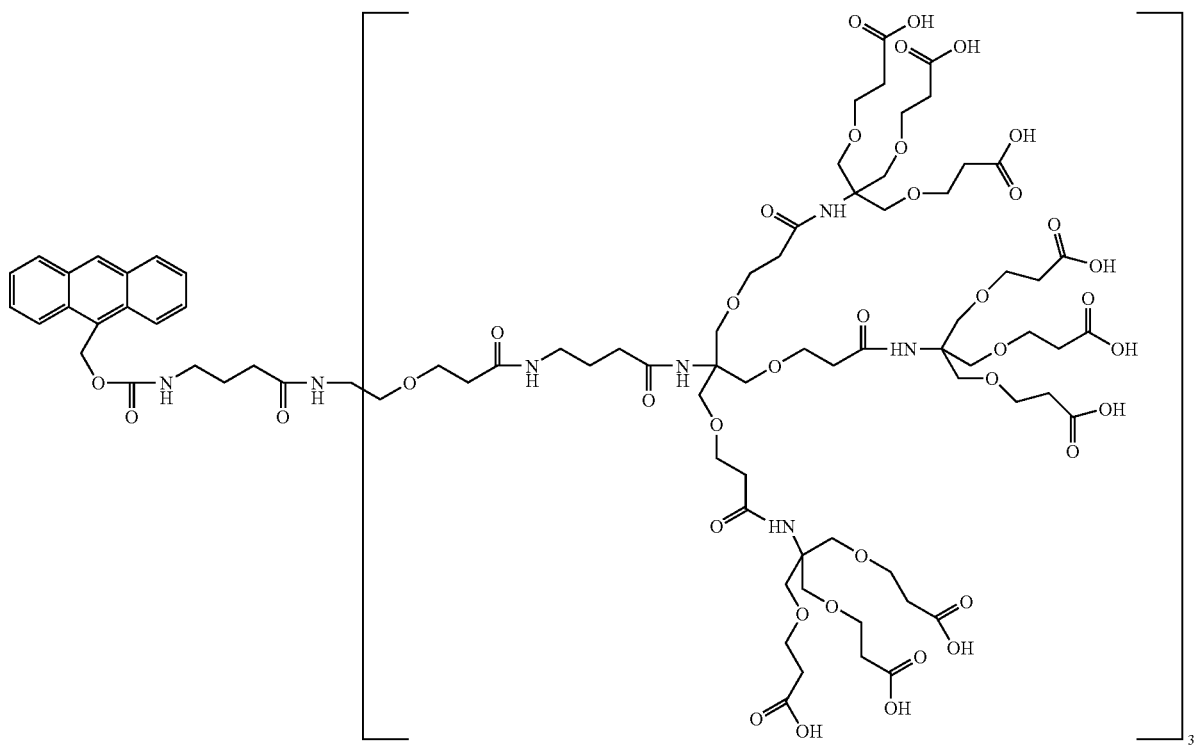

Boc-[1]-acid:
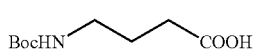
Boc-[3]-ester:
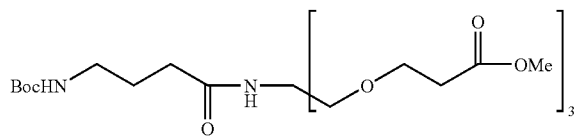
Boc-[3]-acid:
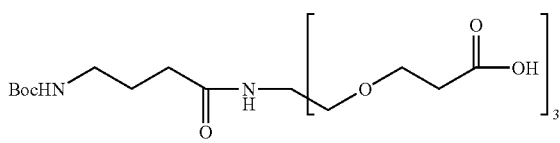
Boc-[9]-ester:
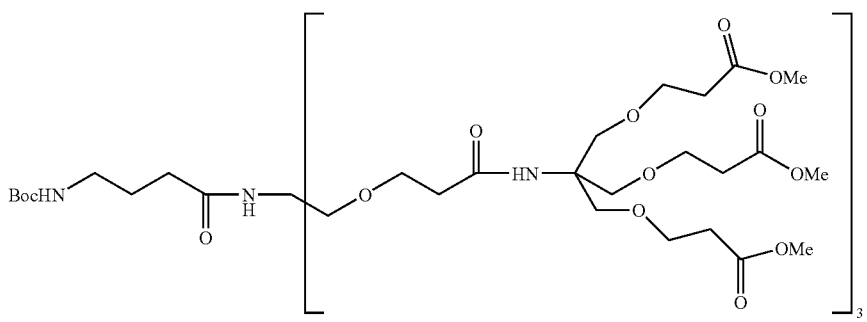
Boc-[9]-acid:
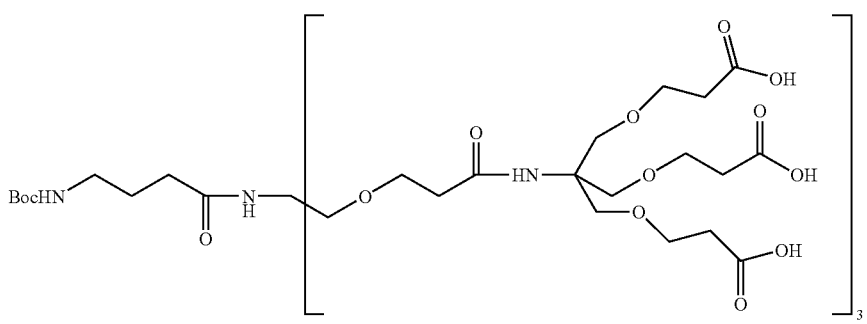
Ns-[9]-ester:
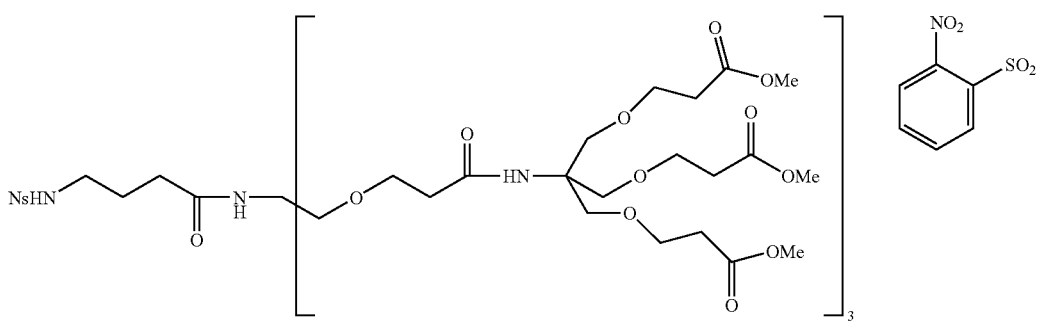
Ns:

-continued
Ns-[9]-acid:
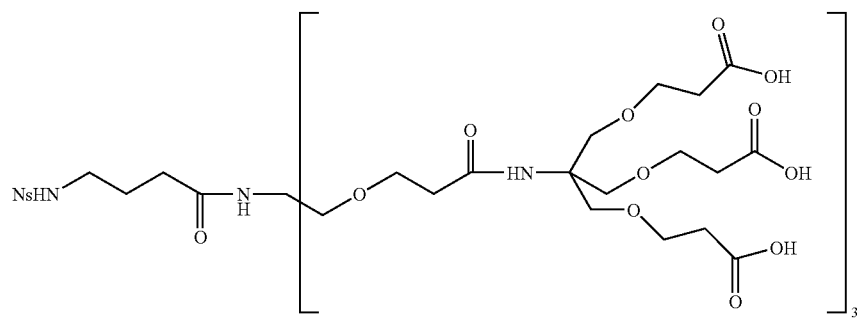
Fmoc-[9]-ester (R = t-butyl)
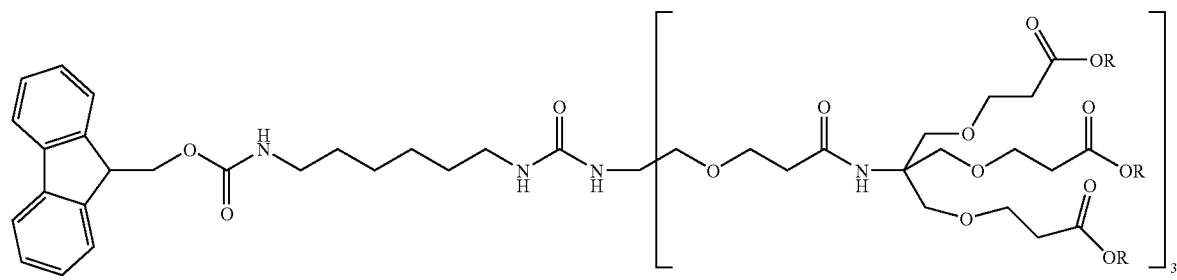
Fmoc-[9]-acid
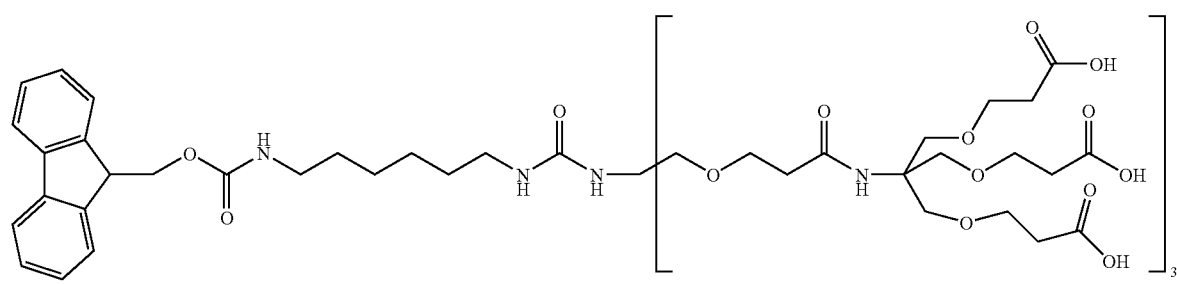
AE-[1]-acid:
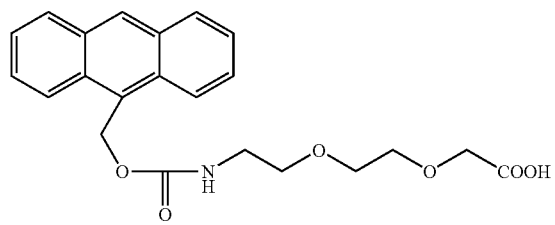
AE-[3]-acid:
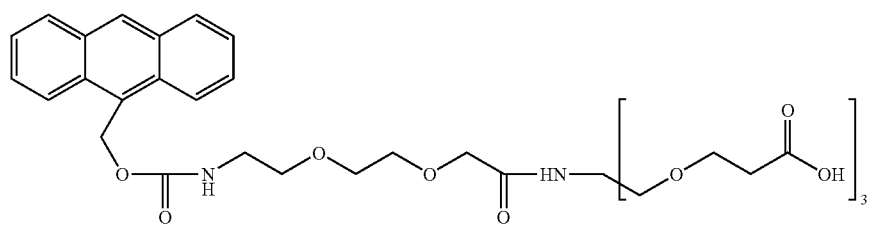

AE-[9]-acid:
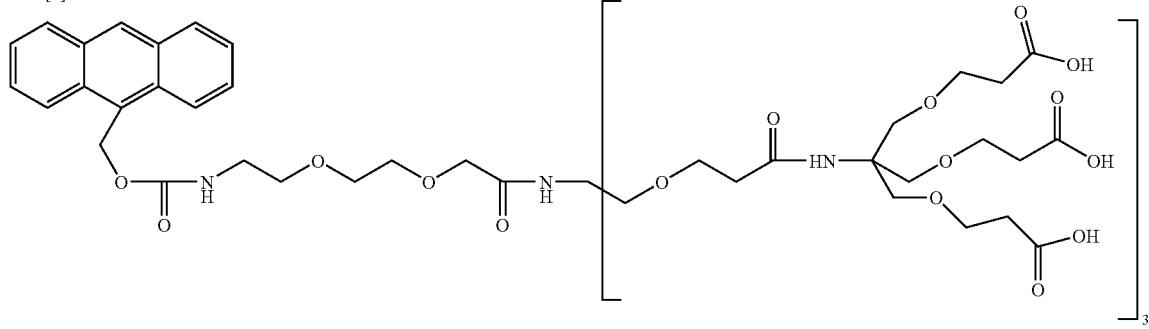
A-[6]-acid:
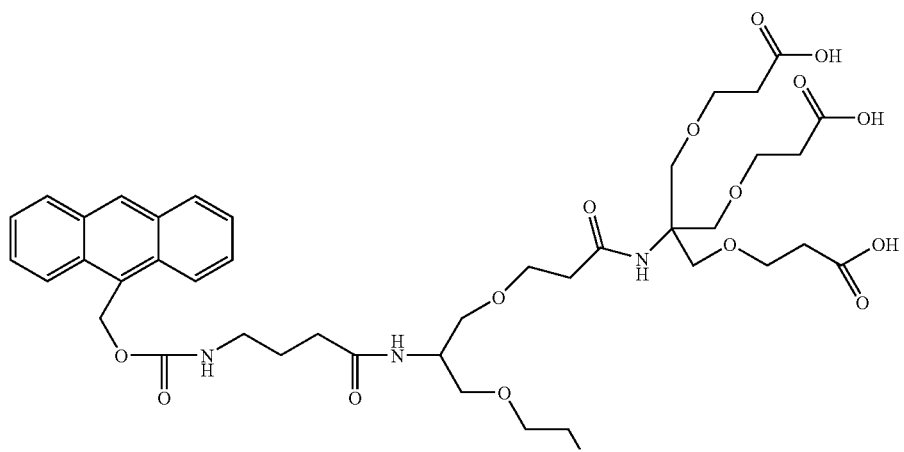
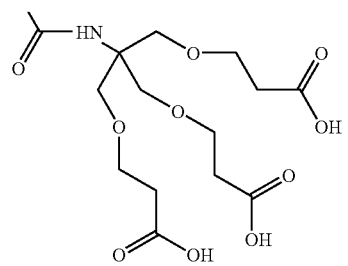

A-[8]-acid:
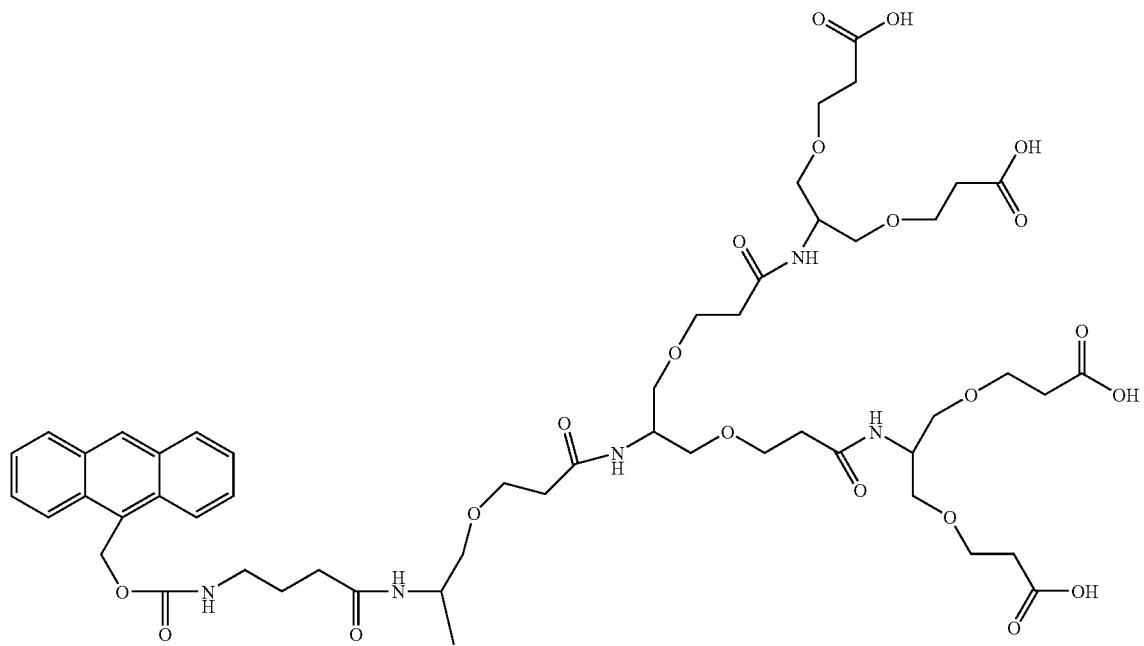
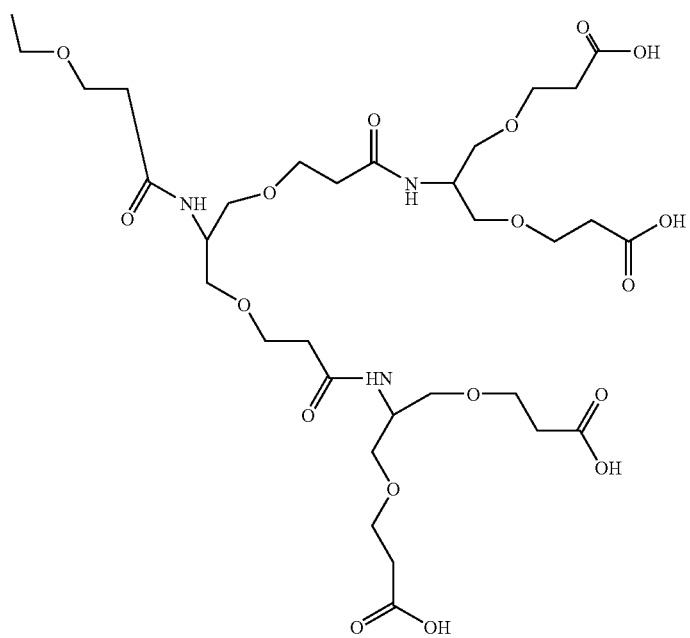

A-[12]-Acid:
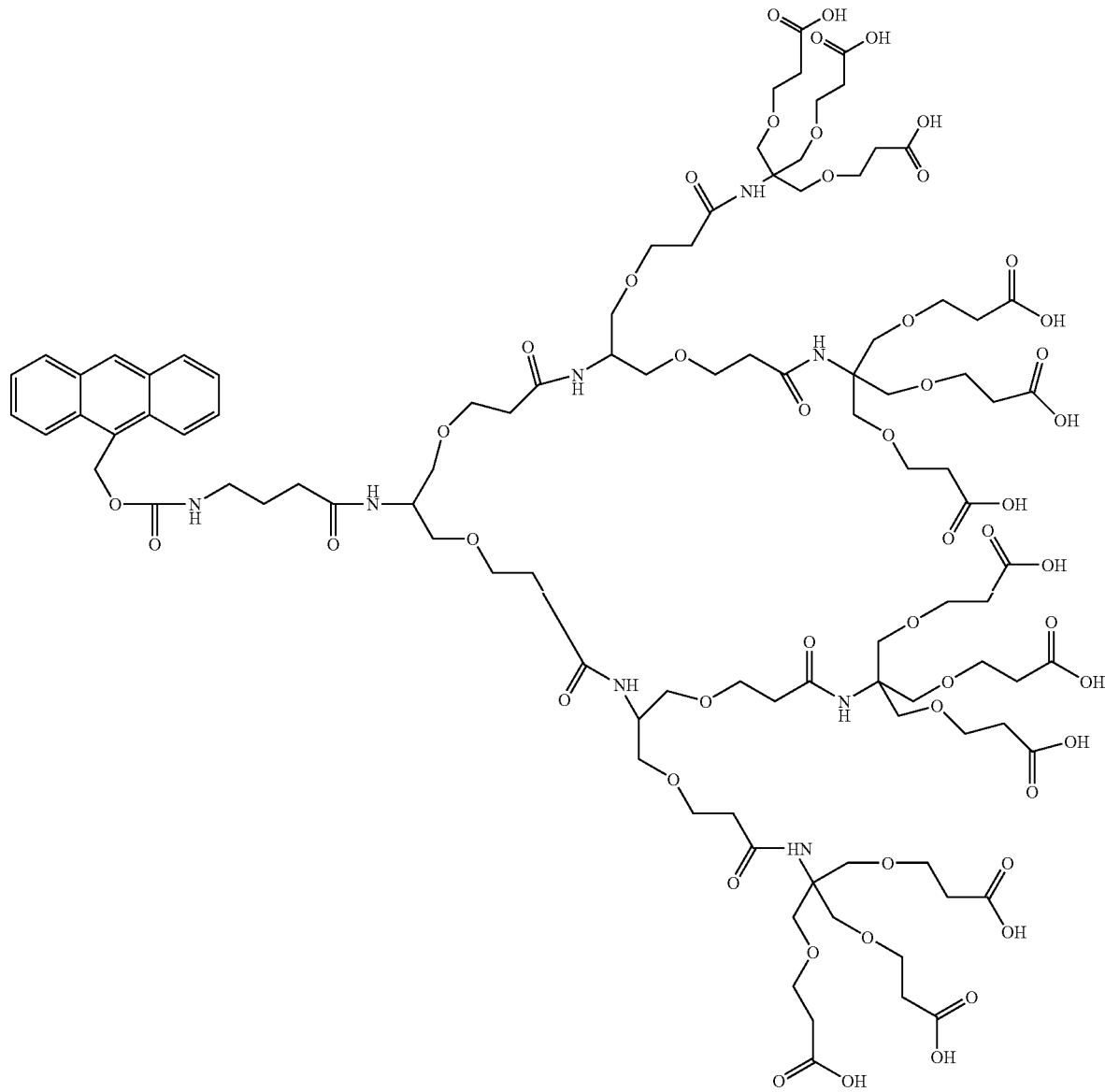
A-[16]-Acid:
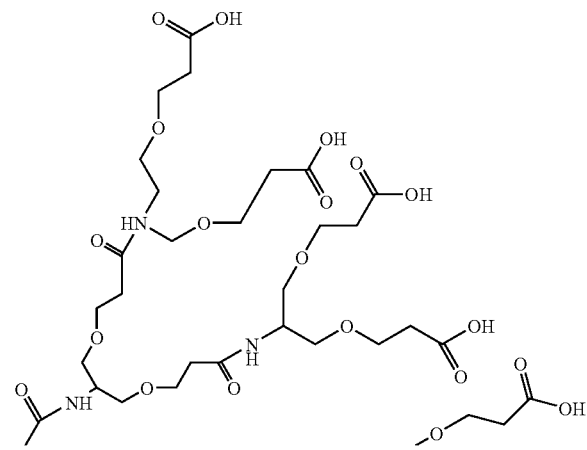

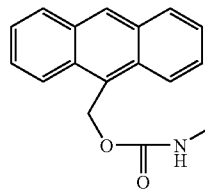
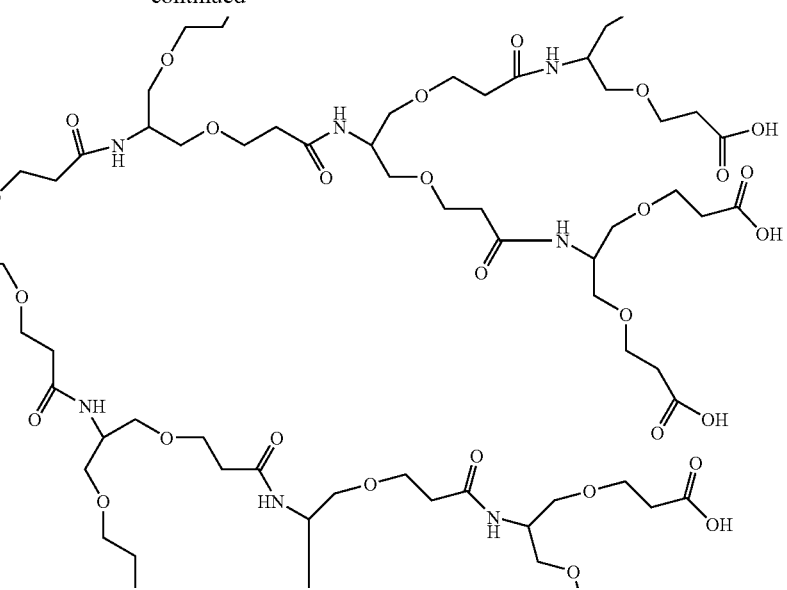
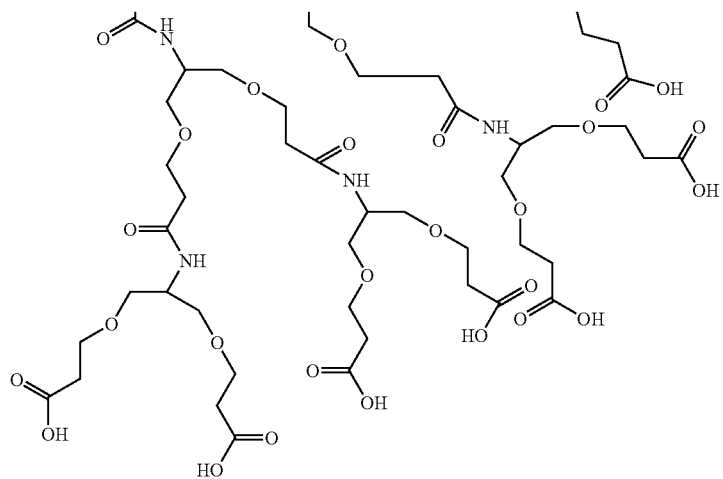
A-[18]-Acid:
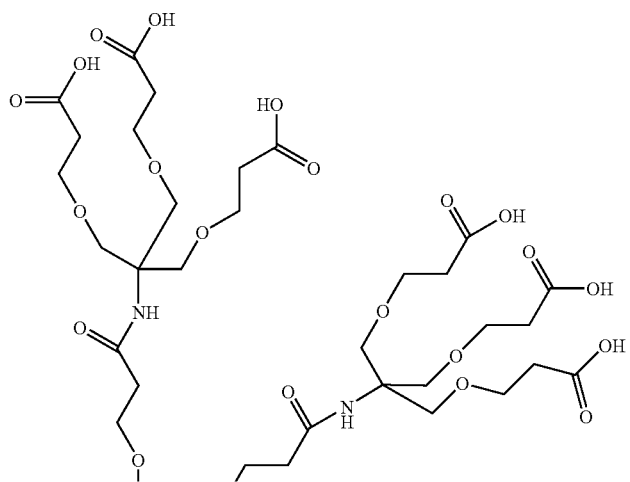

43
-continued
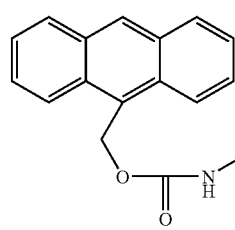
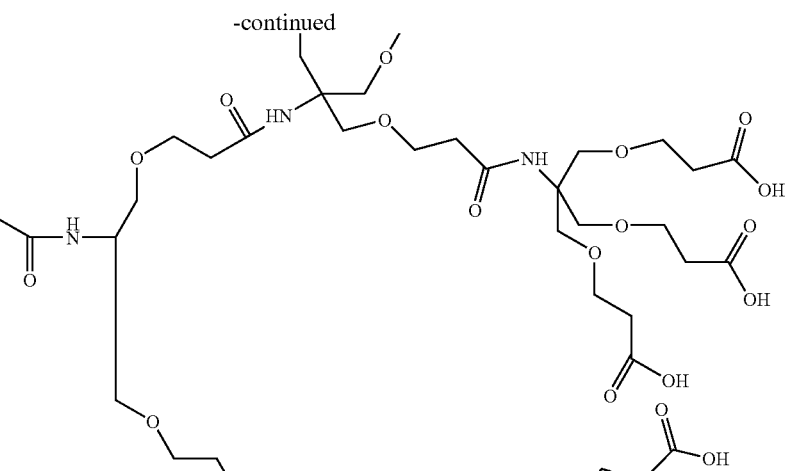
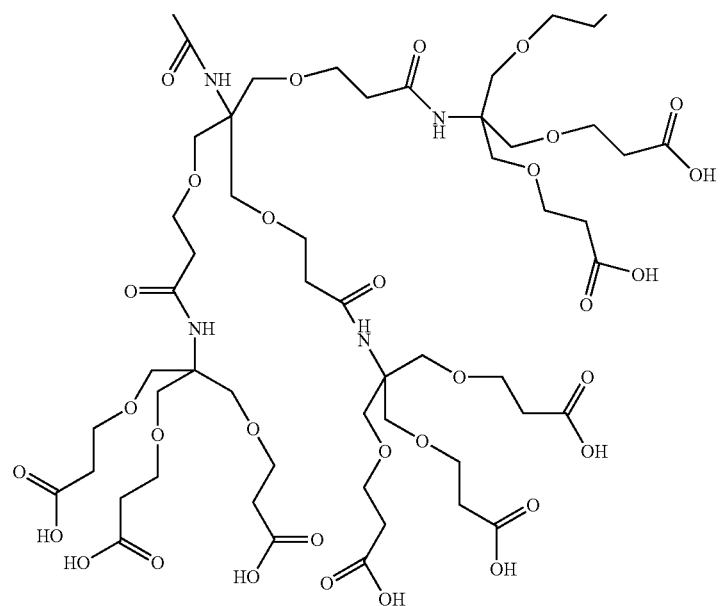
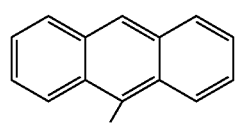
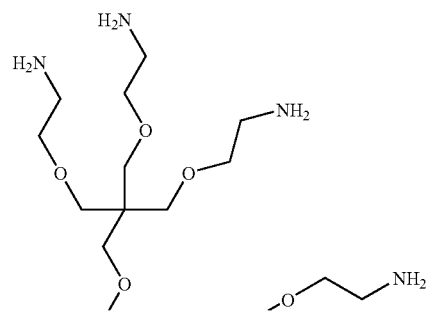

-continued
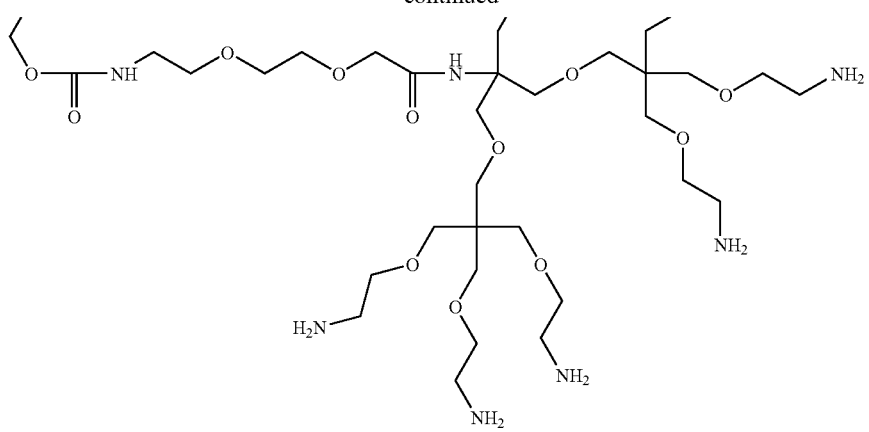
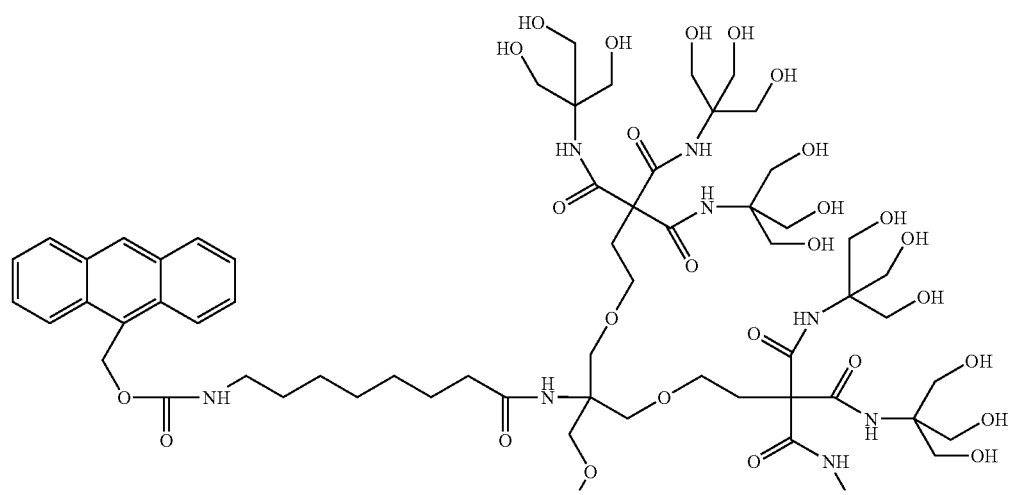
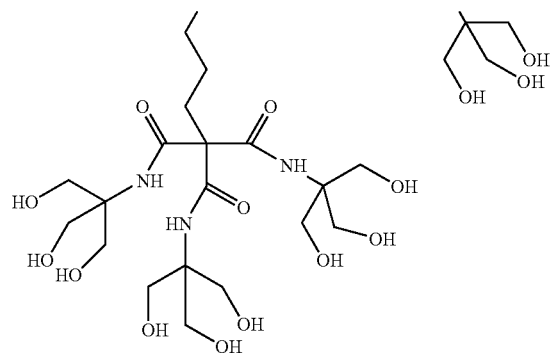

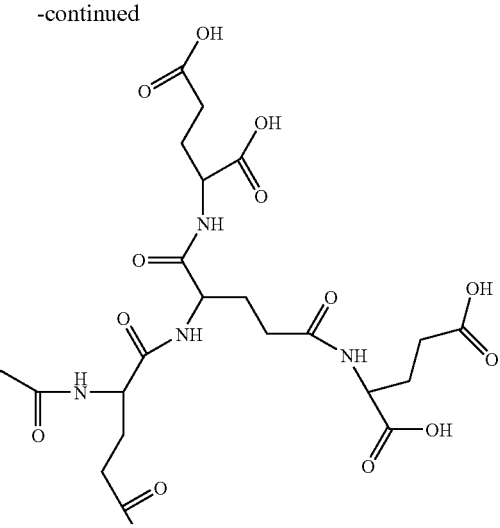
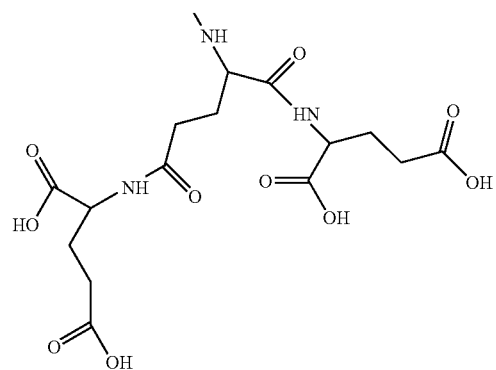
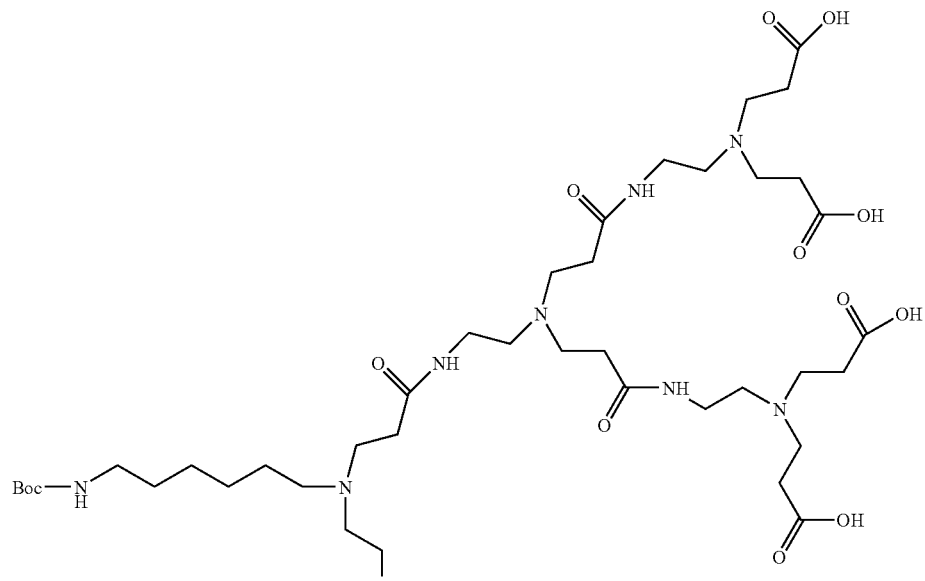

-continued
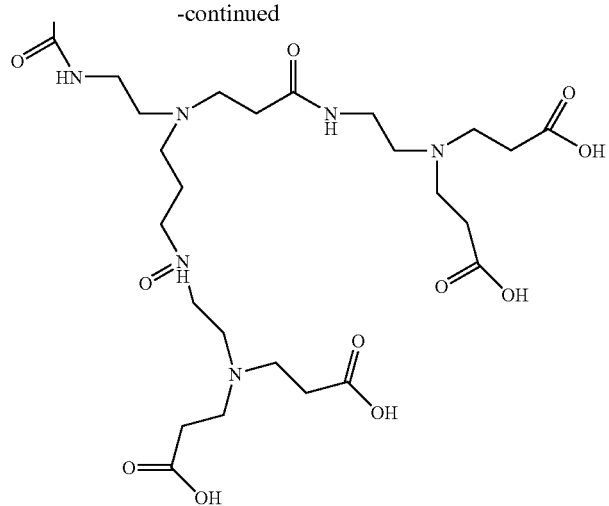
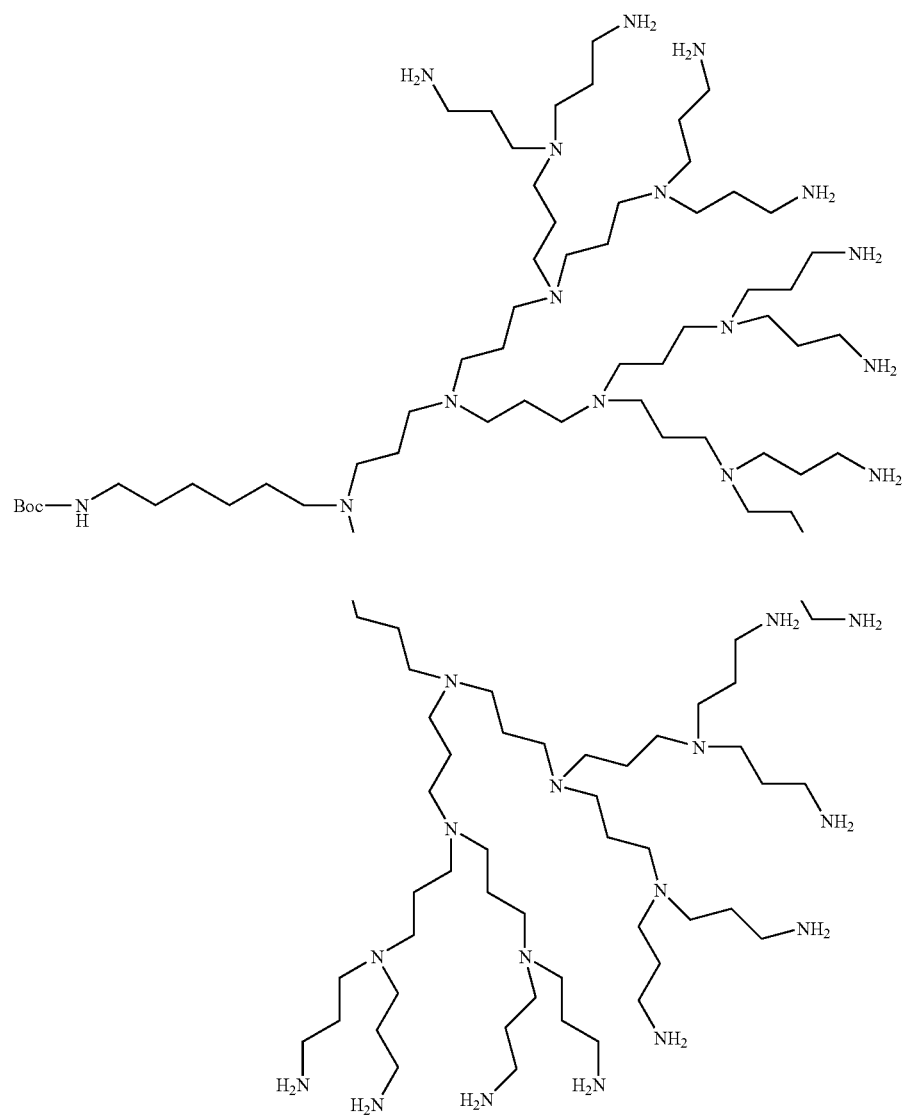

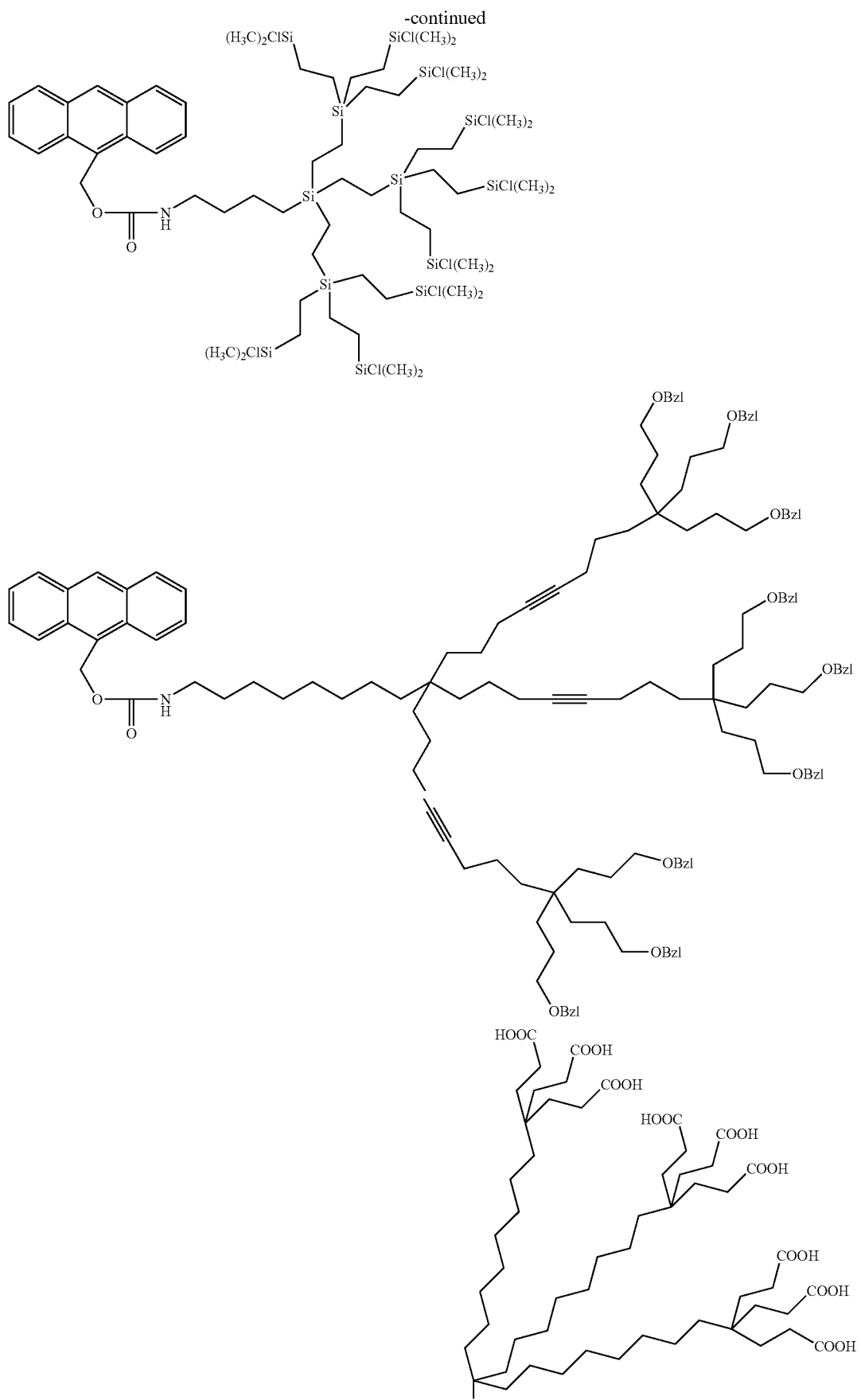

-continued
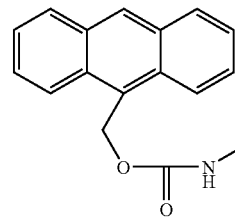
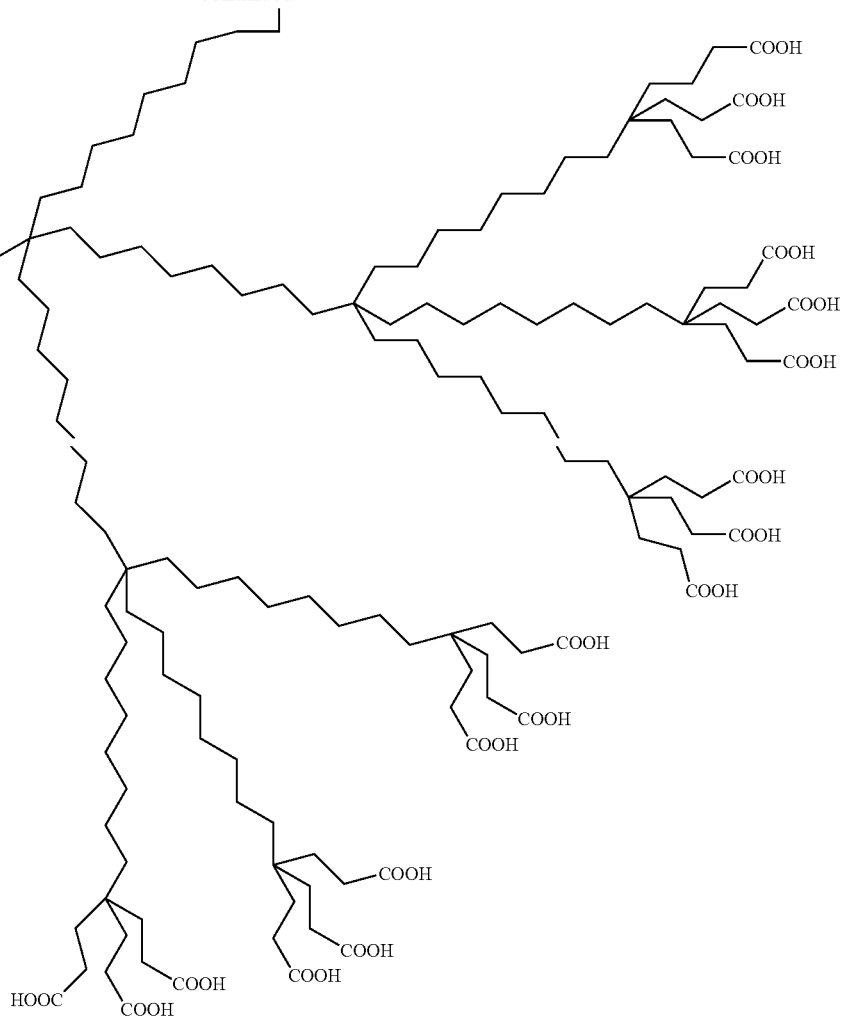
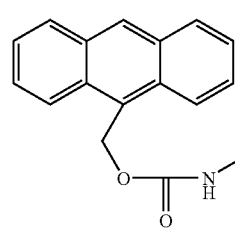

-continued
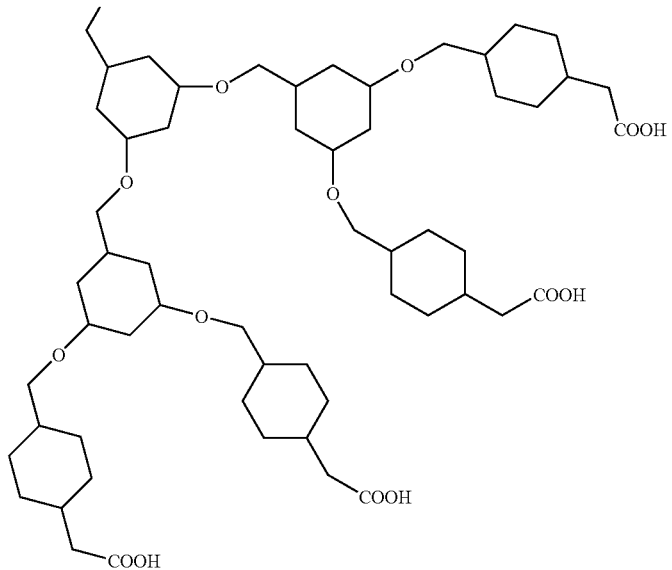
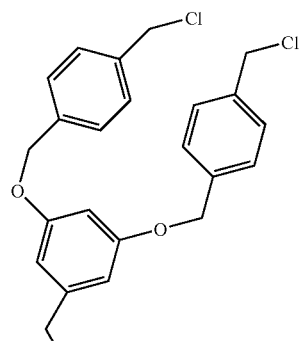
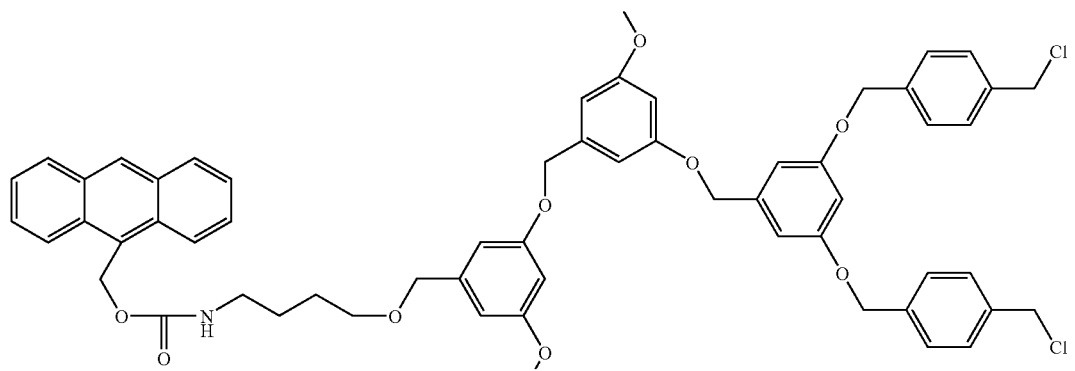

-continued
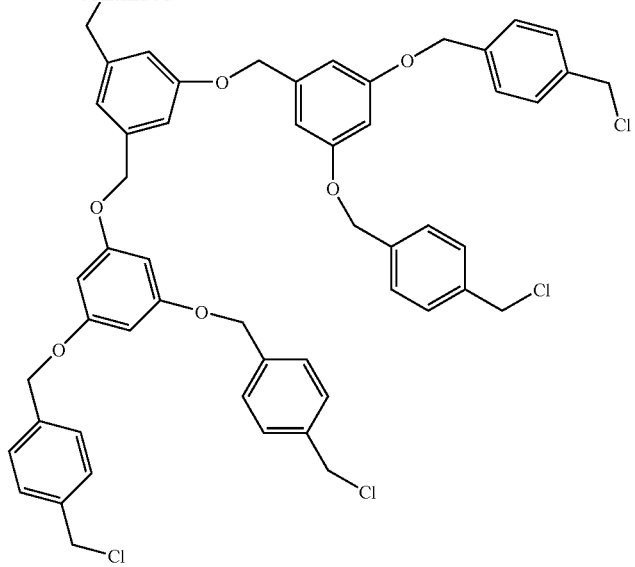
Preparation of A-[27]-OH
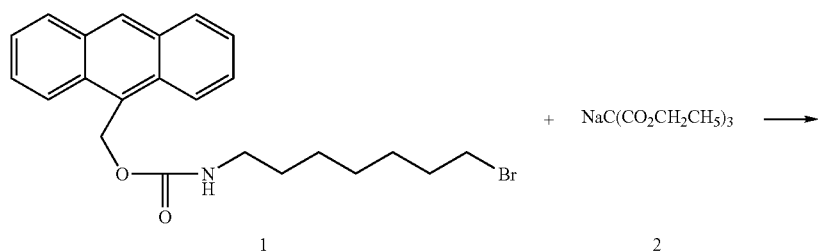
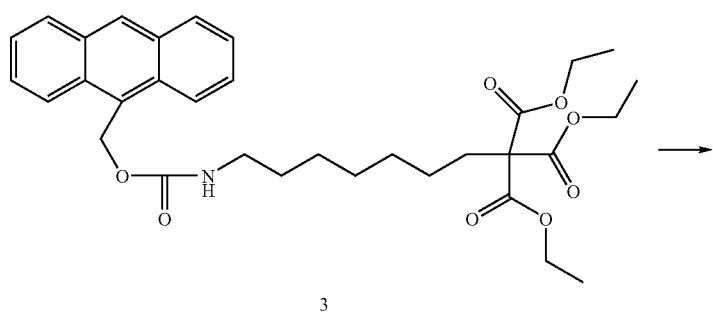
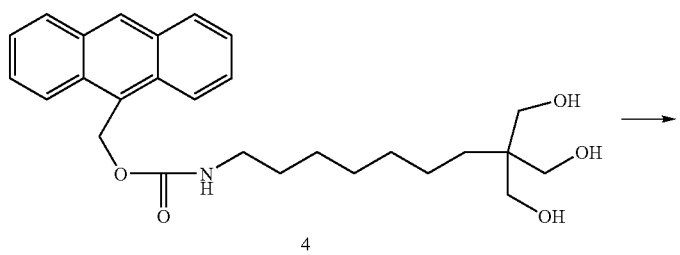

-continued
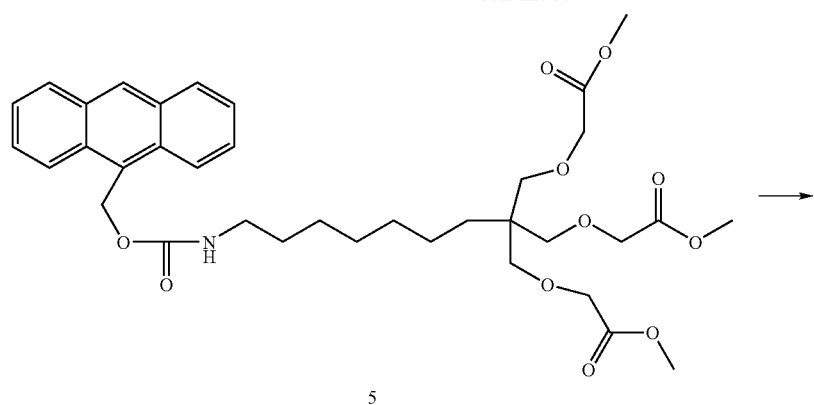
5
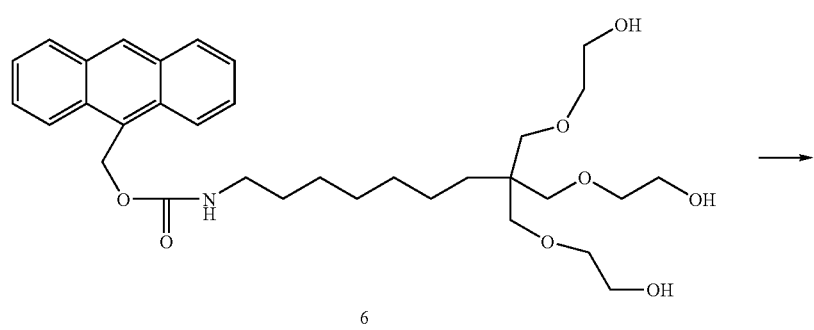
6
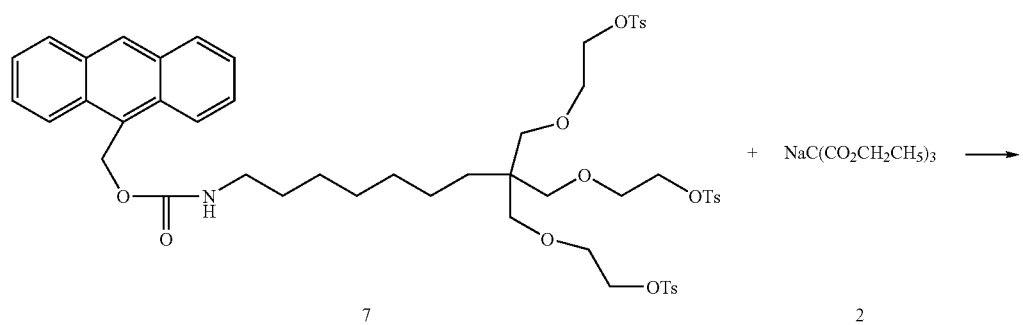
7  +  NaC(CO$_2$CH$_2$CH$_3$)$_3$ ⟶
2
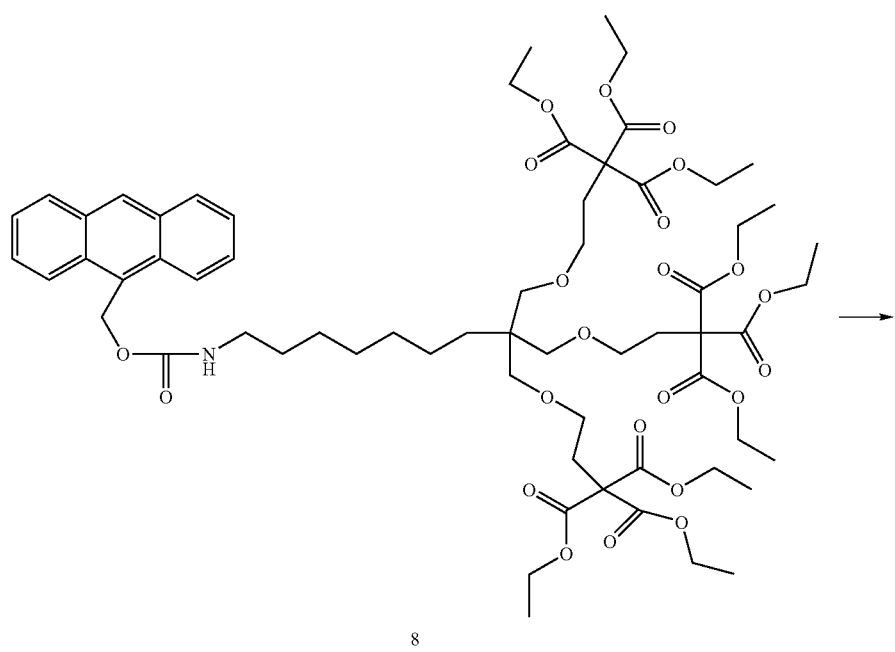
8

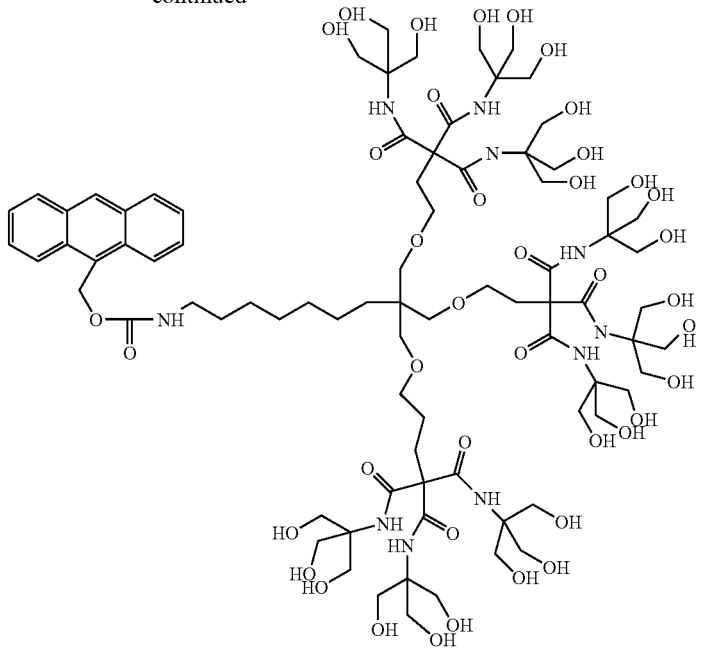

9

Compound 1 was treated with NaC(CO$_2$Et)$_3$ 2 in C$_6$H$_6$/DMF at 80° C. to afford A-[3]-OEt (Compound 3). Compound 3 was reduced with LiAlH$_4$ or LiBH$_4$ in ether, reacted with chloroacetic acid in the presence of t-BuOK/t-BUOH, and esterified with MeOH to produce compound of Formula 5. Reduction of A-[3]-OMe 5 with LiAlH$_4$ in ether gave triol compound 6, which was tosylated to afford compound 7.

A-[3]-OTs (Compound 7) was treated with NaC(CO$_2$Et)$_3$ in C$_6$H$_6$-DMF to afford the desired nonaester (compound 8). Compound 8 (A-[9]-OEt) was treated with tris(hydroxymethyl)aminomethane and K$_2$CO$_3$ in DMSO at 70° C. to afford A-[27]-OH (compound 9).

Preparation of Boc-[8]-OMe

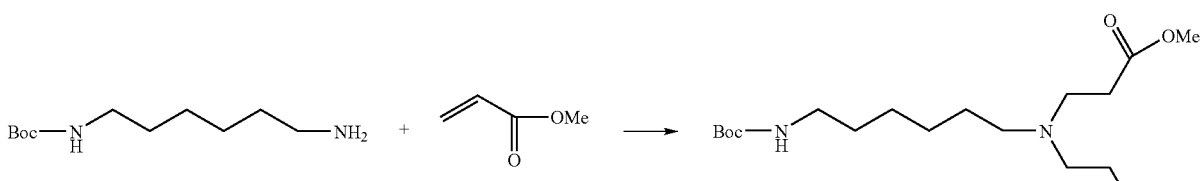

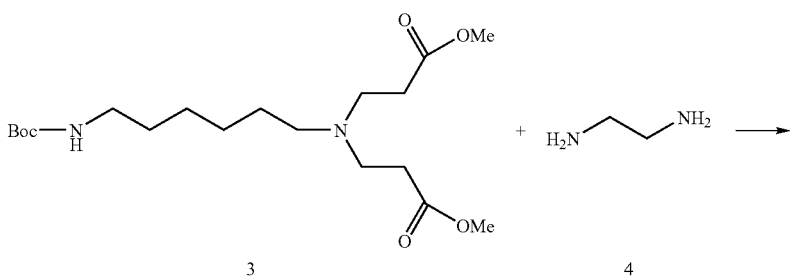

-continued
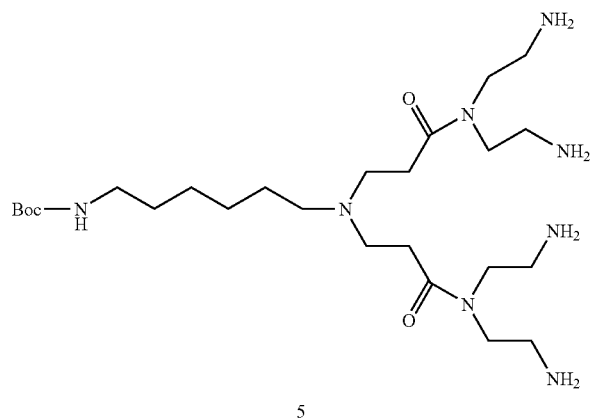
5
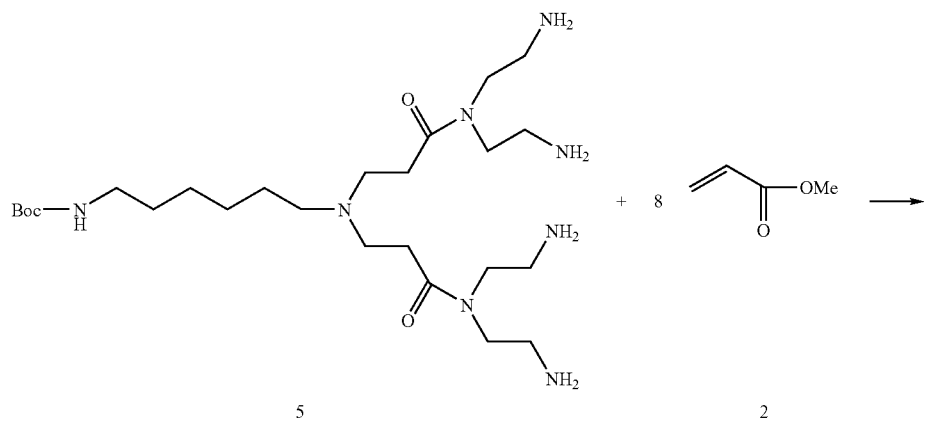
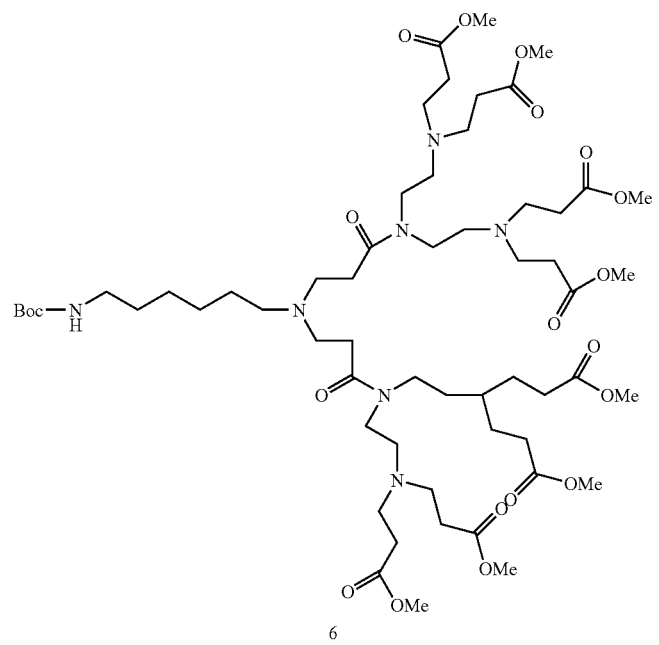 [SMILES: COC(=O)CCC(CCC(=O)OC)CCN(CCN(CCC(=O)OC)CCC(=O)OC)C(=O)CCN(CCCCCCNC(=O)OC(C)(C)C)CCC(=O)N(CCN(CCC(=O)OC)CCC(=O)OC)CCN(CCC(=O)OC)CCC(=O)OC]

Compound 1 was reacted with methyl acrylate 2 in methanol at temperature below 50° C. to afford Compound 3. Boc-[2]-OMe (Compound 3) was reacted with large excesses of ethylenediamine in methanol at temperature below 50° C. to afford Compound 5. Boc-[4]—NH$_2$ (Compound 5) was reacted with methyl acrylate in methanol at temperature below 50° C. to afford Compound 6 (Boc-[8]-OMe).
Preparation of Boc-[8]-OH
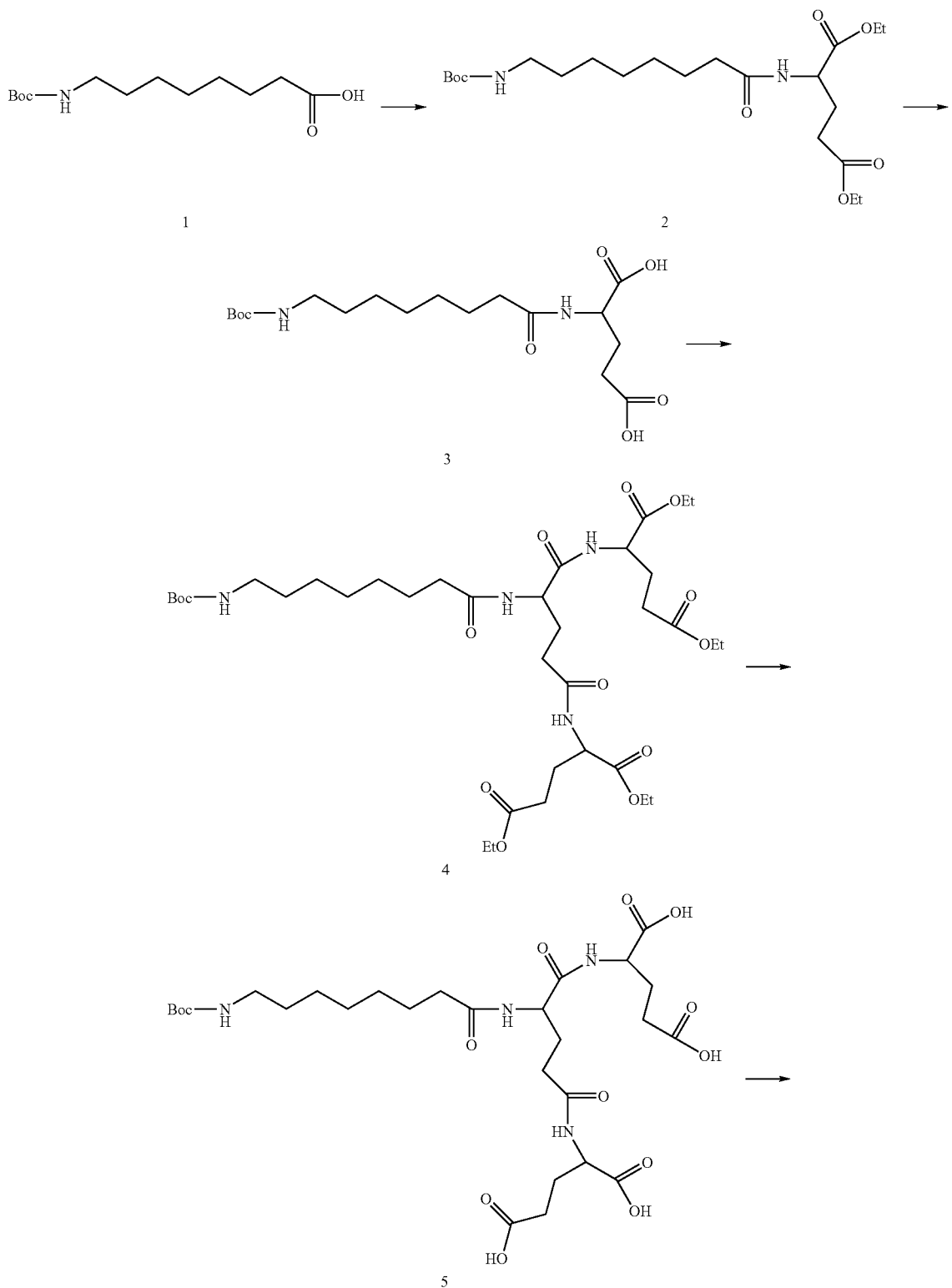

-continued

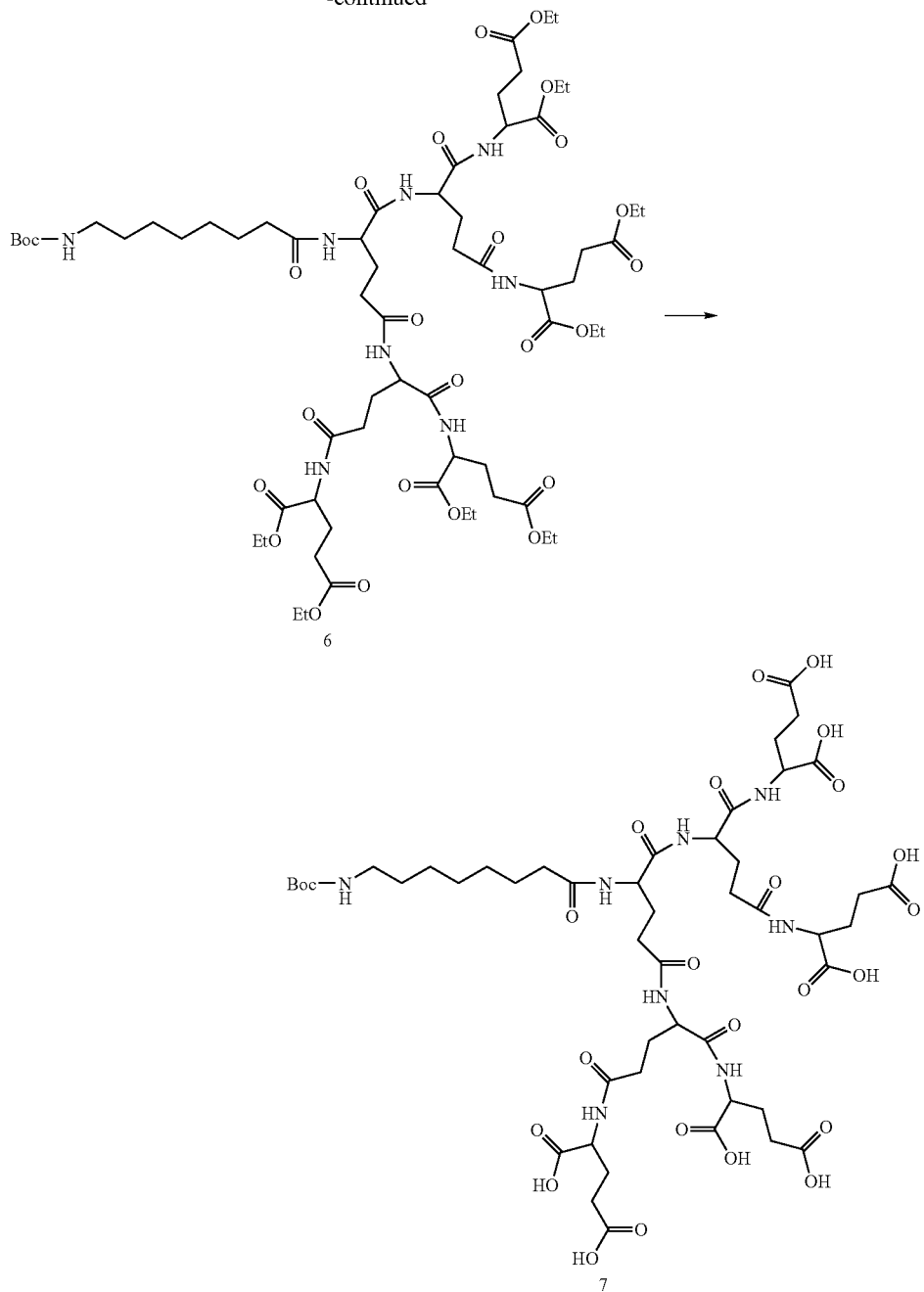

A mixture of 1-[3-(dimethylamino)propyl]-3-ethylcarbodiimide hydrochloride (EDC) and 1-hydroxybenzotriazole hydrate (HOBT) in acetonitrile was stirred at room temperature. To this mixture a solution of L-glutamic acid-diethyl ester in acetonitrile was added with stirring at room temperature. After 12 h, the acetonitrile was removed, and the crude product was dissolved in EA and washed with 1.0 N HCl and saturated sodium bicarbonate solution. The organic layer was dried over MgSO$_4$, filtered, concentrated, and purified by silica gel chromatography (eluent:ethyl acetate: haxane) to yield Compound 2 as a viscous yellow liquid.

Compound 2 in an organic solvent was stirred at room temperature in the presence of a NaOH solution for 1 d, after which the organic liquid was evaporated. The resulting aqueous solution was washed with EA, stirred in an ice bath and acidified with dilute HCl. The aqueous solution was then extracted with EA. The organic layers were combined, dried over MgSO$_4$, filtered, and concentrated to afford Compound 3.

To a mixture of Compound 3, 1-[3-(dimethylamino)propyl]-3-ethylcarbodiimide hydrochloride (EDC), and 1-hydroxybenzotriazole hydrate (HOBT) in acetonitrile at room temperature was added a solution of L-glutamic acid-diethyl ester in acetonitrile. After 12 h, the acetonitrile was evaporated and the crude product was dissolved in EA and washed with 1.0 N HCl and saturated sodium bicarbonate solution. The organic layer was dried over MgSO$_4$, filtered, concentrated, and purified by column chromatography (eluent:ethyl acetate:haxane) to afford Compound 4 as a viscous yellow liquid.

A mixture of Compound 4 in an organic solvent and a NaOH solution was stirred at room temperature for 1 d, after which the organic liquid was evaporated. The aqueous solution was washed with EA, stirred in an ice bath and acidified with dilute HCl. After the product was extracted with EA, the organic solution was dried with anhydrous MgSO$_4$, filtered and evaporated to provide Compound 5.

To a solution of Compound 5, 1-[3-(dimethylamino) propyl]-3-ethylcarbodiimide hydrochloride (EDC), and 1-hydroxybenzotriazole hydrate (HOBT) in acetonitrile was added a solution of L-glutamic acid-diethyl ester in acetonitrile. After stirring at room temperature for 12 h, the acetonitrile was evaporated. The crude product was dissolved in EA and washed with 1.0 N HCl and saturated sodium bicarbonate solution. The resulting organic layer was dried over MgSO$_4$, filtered, concentrated, and purified by column chromatography (eluent:ethyl acetate:haxane) to afford Compound 6 as a viscous yellow liquid.

A mixture of Compound 6 in an organic solvent and a NaOH solution was stirred at room temperature for 1 d, after which the organic liquid was evaporated. The aqueous solution was washed with EA, stirred in an ice bath and acidified with dilute HCl. After the product was extracted with EA, the organic solution was dried with anhydrous MgSO$_4$, filtered and evaporated to afford Compound 7 (Boc-[8]-OH).

Preparation of Boc-[16]—NH$_2$

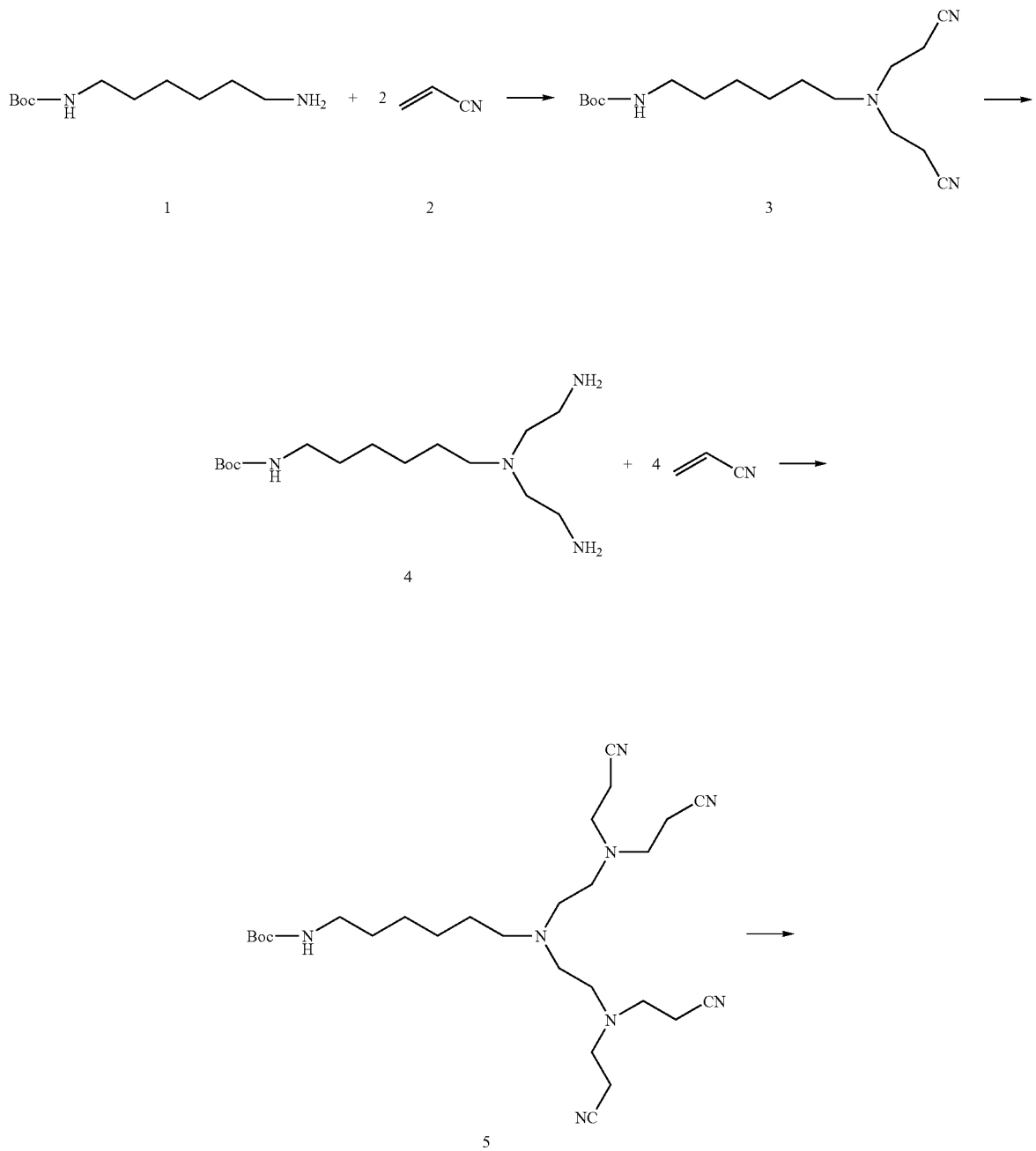

-continued
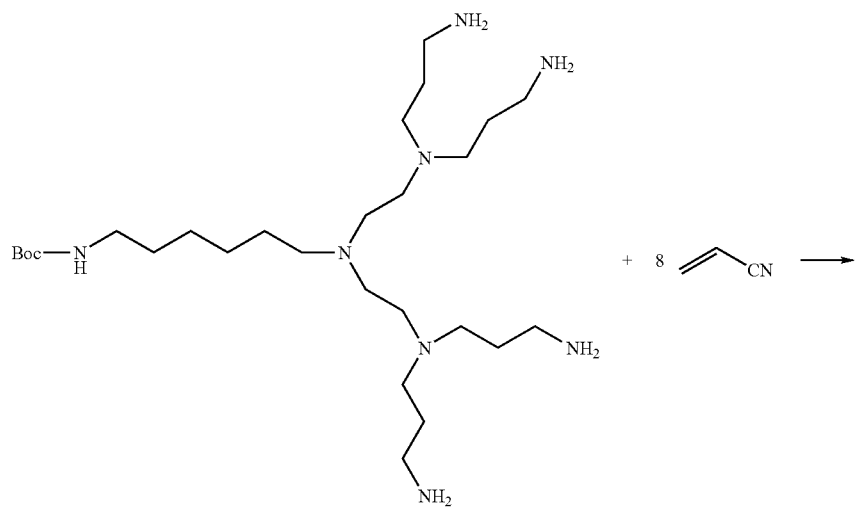
6
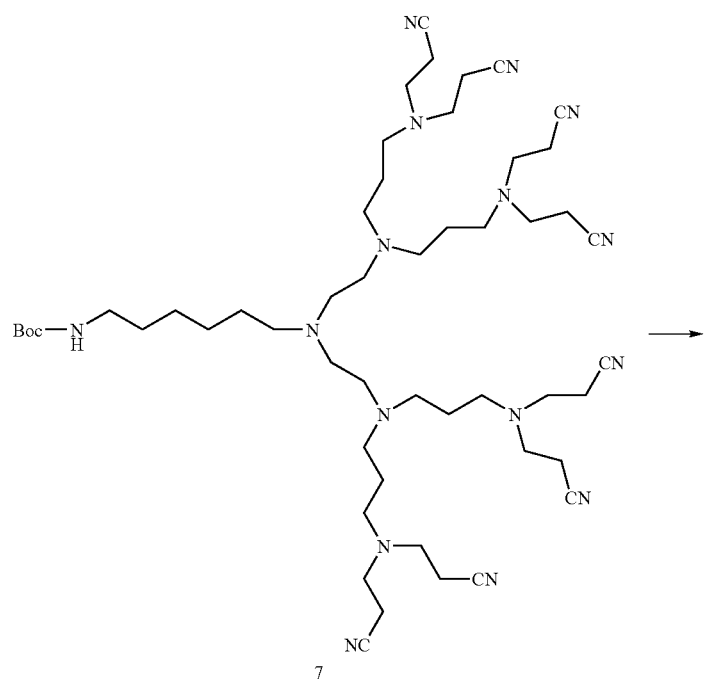
7

-continued
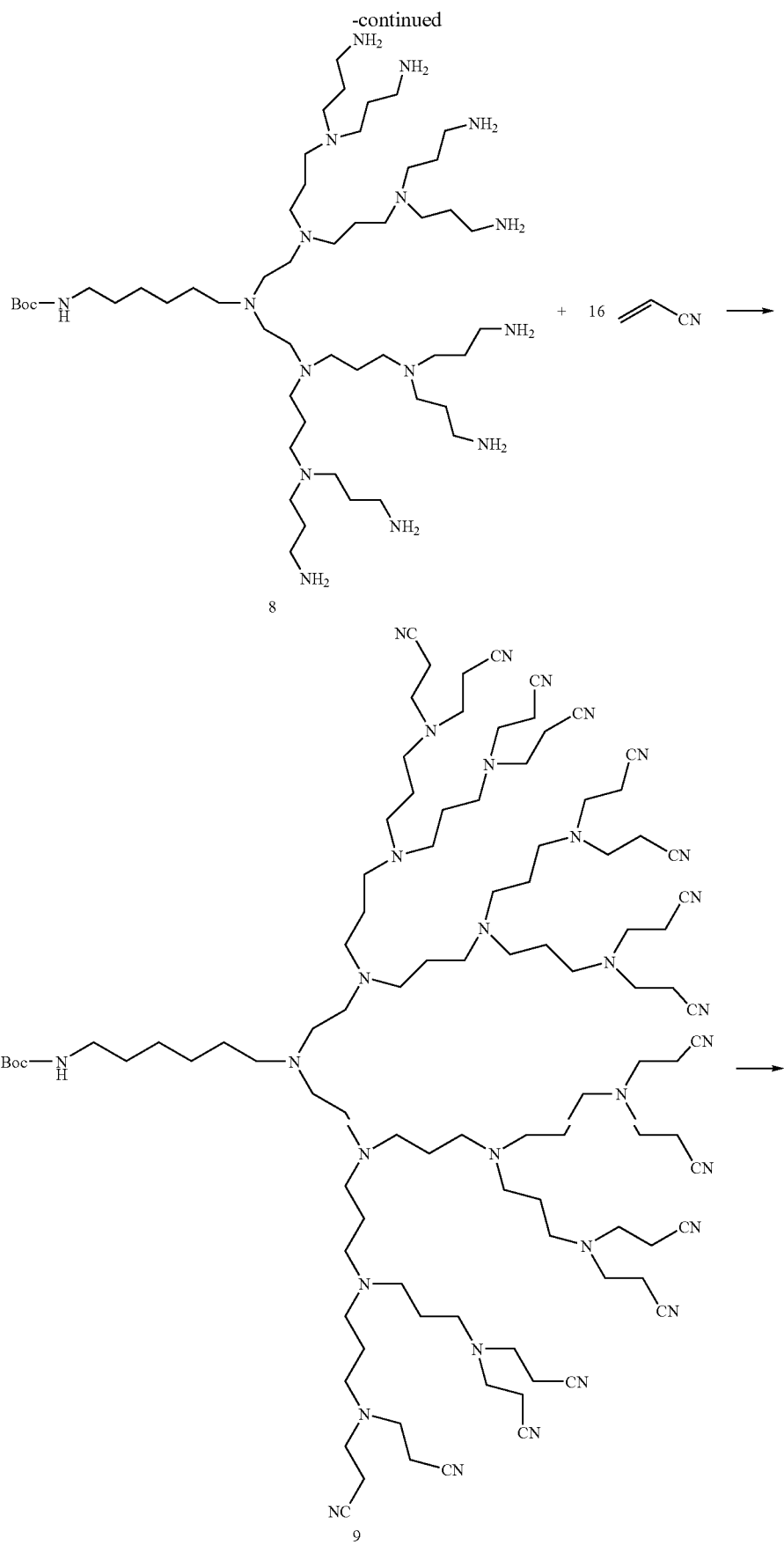

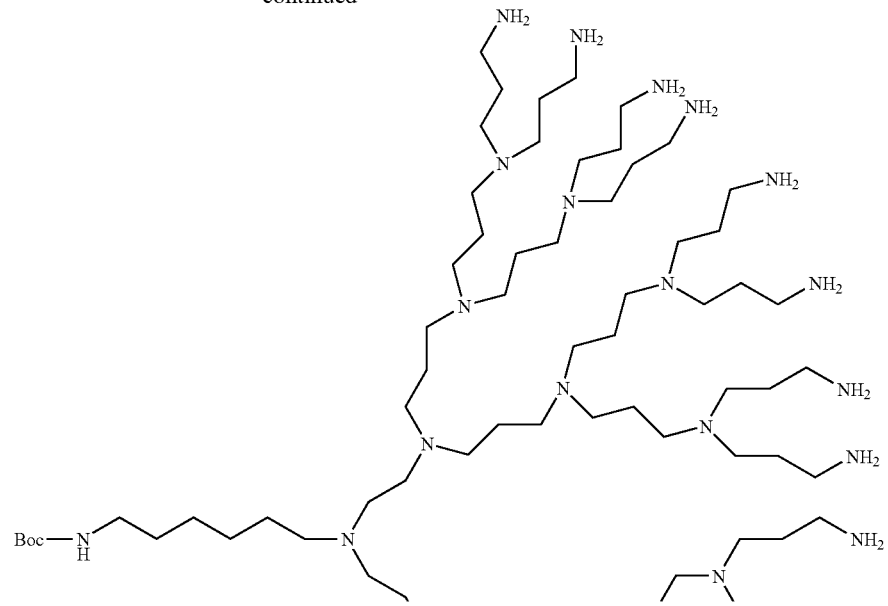

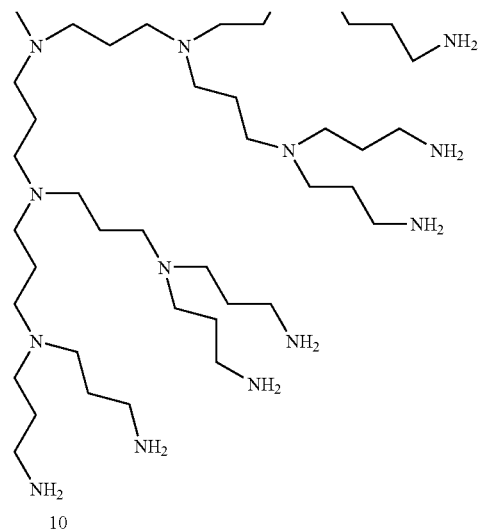

10

To a solution of Compound 1 in acrylonitrile was added acetic acid and the resulting solution was refluxed for 24 h. Acrylonitrile was distilled off under vacuum, and the residue was extracted with chloroform, and added to concentrated ammonia solution. The organic phase was separated, washed with water, and dried with sodium sulfate to yield Compound 3. To a mixture of Boc-[2]-CN (Compound 3) and cobalt(II) chloride hexahydrate in methanol was added sodium borohydride. The resultant mixture was stirred for 2 h at room temperature and then acidified with concentrated hydrochloric acid. Methanol was removed and the residue was diluted with an organic solvent, washed with water, and dried with sodium sulfate to yield Compound 4.

The above processes were repeated with Boc-[2]—$NH_2$ (Compound 4) to yield Compound 6.

The above processes were again repeated with Boc-[4]—$NH_2$ (Compound 6) to yield Compound 8.

The above processes were again repeated with Boc-[8]—$NH_2$ (Compound 8) to yield Compound 10 (Boc-[16]—$NH_2$).

Preparation of A-[9]—SiCl₃
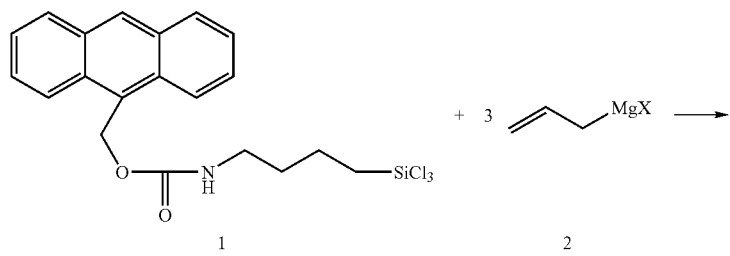
1 + 3 ⟶ ²⁄MgX ⟶
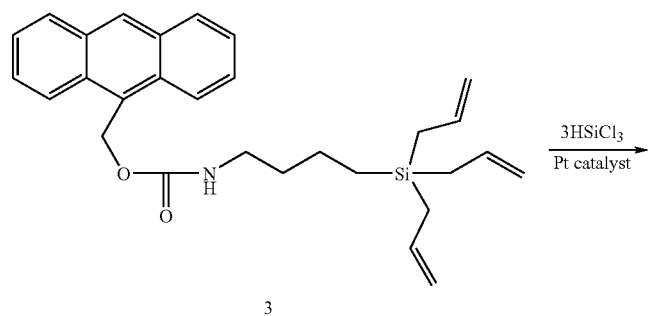
3
$\xrightarrow{\text{3HSiCl}_3}{\text{Pt catalyst}}$
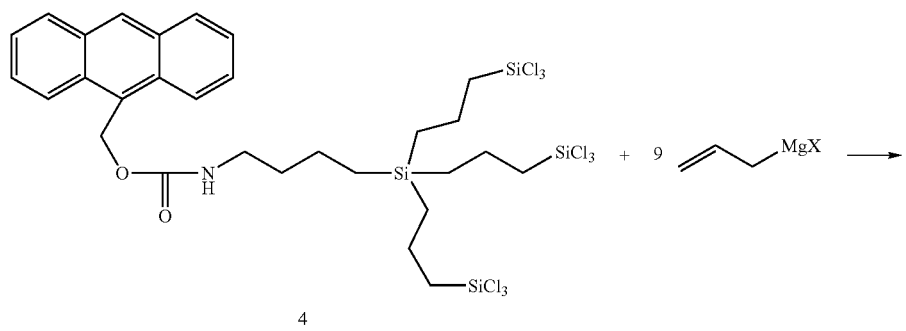
4 + 9 ⟶ ²⁄MgX ⟶
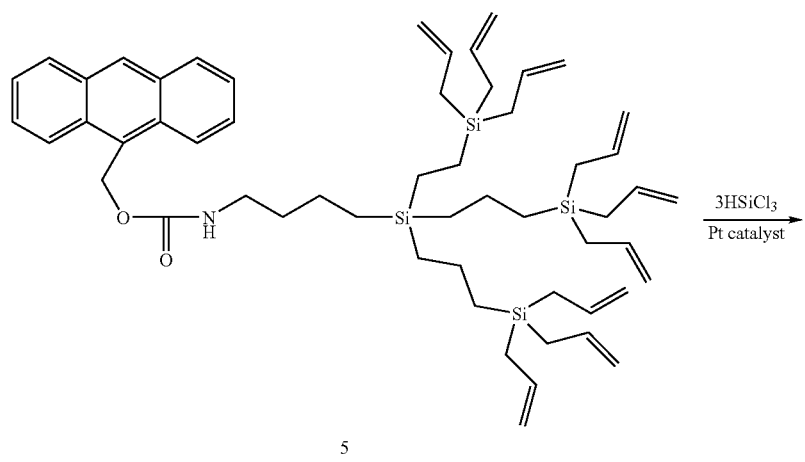
5
$\xrightarrow{\text{3HSiCl}_3}{\text{Pt catalyst}}$ -continued

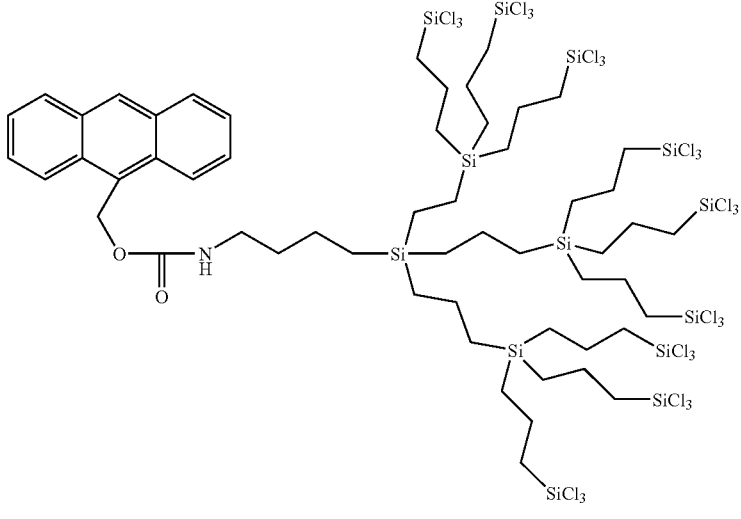

6

A mixture of Compound 1 and 10% excess of allylmagnesium bromide in diethyl ether was refluxed with for 4 h. The reaction mixture was cooled to 0° C. and hydrolyzed with 10% aqueous NH$_4$Cl. The organic layer was washed with water, dried over MgSO$_4$ and concentrated to yield Compound 3.

A mixture of A-[3]-Alkene 3, HSiCl$_3$, and a common platinum-based hydrosilylation catalyst, e.g. H2PtCl6 in propan-2-ol (Speier's catalyst) or platinum divinylsiloxane complex (Karstedt's catalyst), was stirred for 24 h at room temperature. Excess HSiCl$_3$ was removed under vacuum to yield Compound 4.

The above processes were repeated with Compound 4 to yield Compound 6 (A-[9]—SiCl$_3$).

Preparation of A-[3]-Alkyne-[9]-OBzl

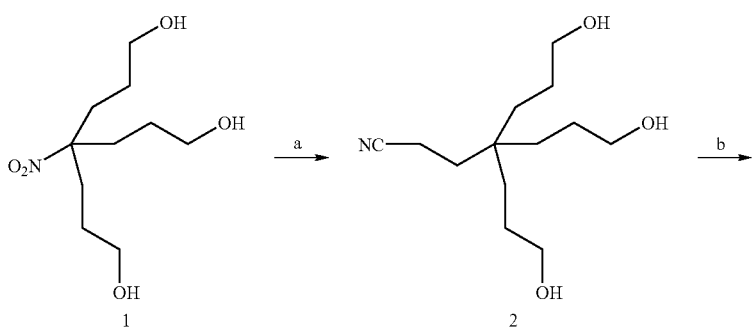

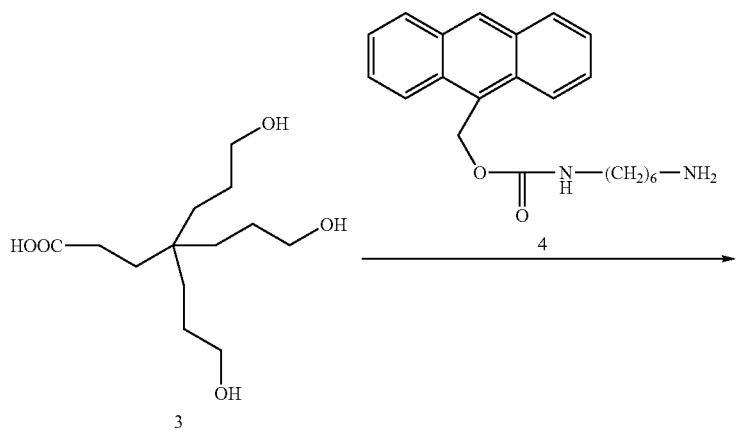

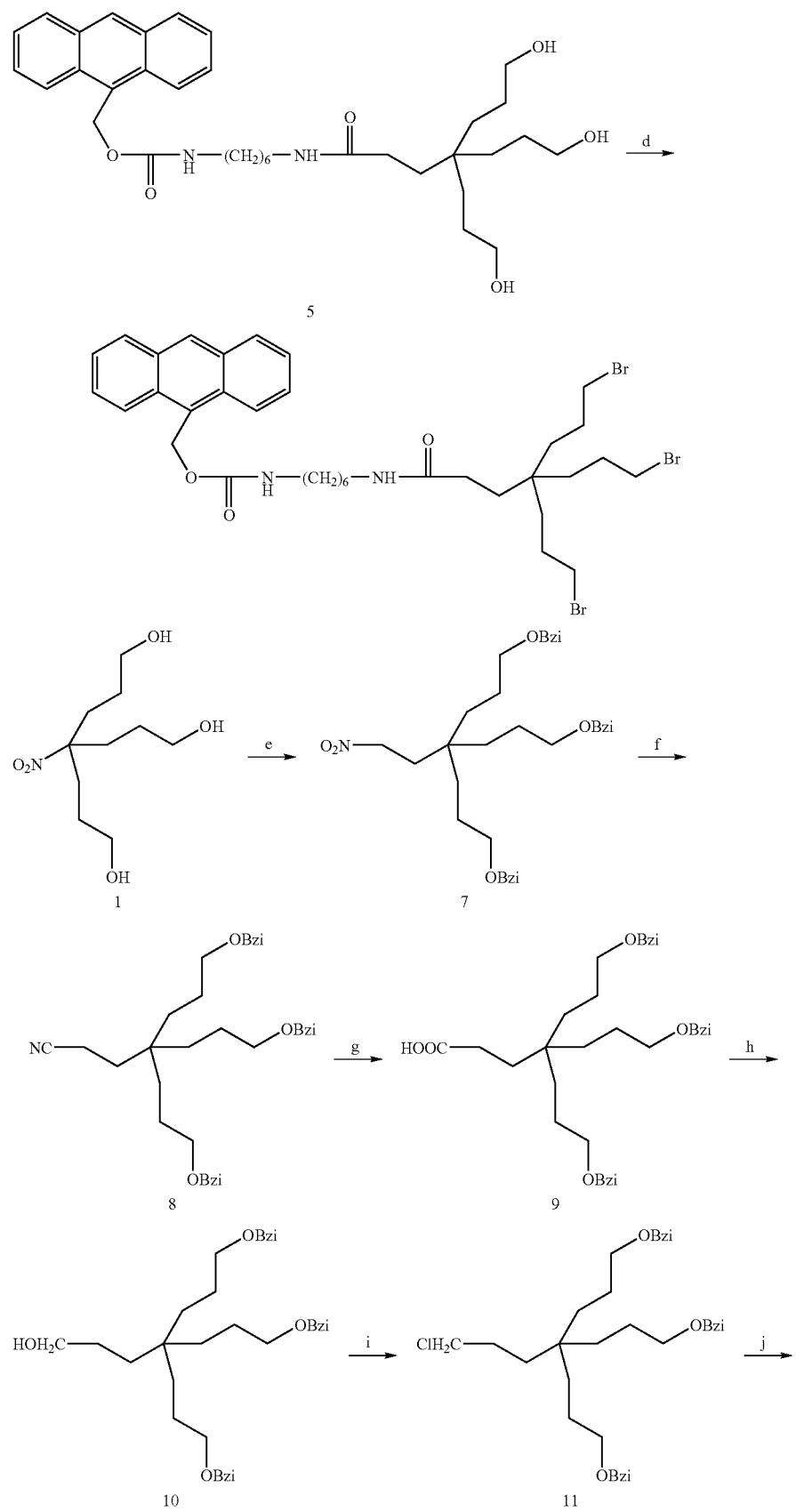

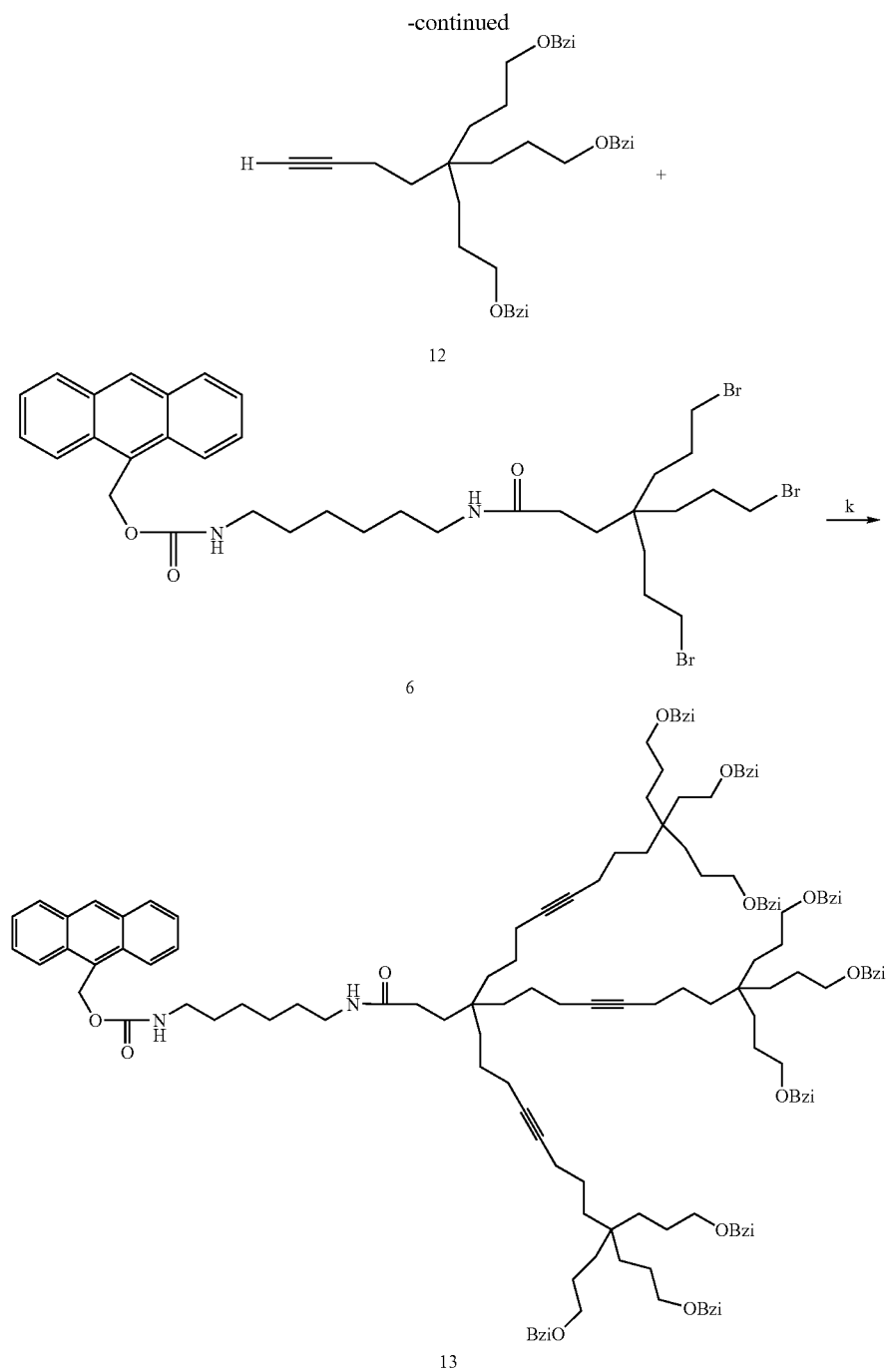

(a) The triol 1 was cyanoethylated affording the nitrile compound 2. Acrylonitrile, nBu$_3$SnH, and azobisisobutyronitrile was added in PhCH$_3$ including compound 1 at 110° C. (b) The nitrile compound 2 was hydrolyzed to give compound 3 with carboxylic acid in such condition as KOH, EtOH/H$_2$O, H$_2$O$_2$, Δ. (c) [1]-acid-[3]-triol was linked with compound 4 through an amide coupling reaction using 1-[3-(dimethylamino)propyl]-3-ethylcarbodiimide hydrochloride (EDC) and 1-hydroxybenzotriazole hydrate (HOBT). (d) The alcohol was used to synthesize tribromide by bromination with HBr/H$_2$SO$_4$ at 100° C. (e) The triol 1 was treated with benzyl chloride to give tris-ether 7 using Me$_2$SO and KOH. (f) The tris-ether 7 was cyanoethylated affording the nitrile compound 8. Acrylonitrile, nBu$_3$SnH, and azobisisobutyronitrile was added in PhCH$_3$ including compound 8 at 110° C. (g) The nitrile compound 8 was hydrolyzed to give compound 9 with carboxylic acid in such condition as KOH, EtOH/H$_2$O, H$_2$O$_2$, Δ. (h) The compound 9 with a carboxylic acid was treated with excess 1.0 M BH$_3$-THF solution to converse the acid into alcohol. (i) The alcohol was transformed into chloride (CH$_2$Cl$_2$) with excess SOCl$_2$ and a catalytic amount of pyridine. (j) The chloride was reacted with lithium acetylide ethylenediamine complex in dimethylsulphoxide at 40° C. (k) The A-[3]-OBzl 6 was alkylated with 4 equivalents of terminal alkyne building block 12, hexamethylphosphoric rtriamide (HMPA), lithium diisopropylamide (LDA), and tetramethylethylenediamine (TMED) at 0-40° C. for 1.5 h to yield Compound 13 (A-[3]-Alkyne-[9]-OBzl).
Preparation of A-[27]-COOH
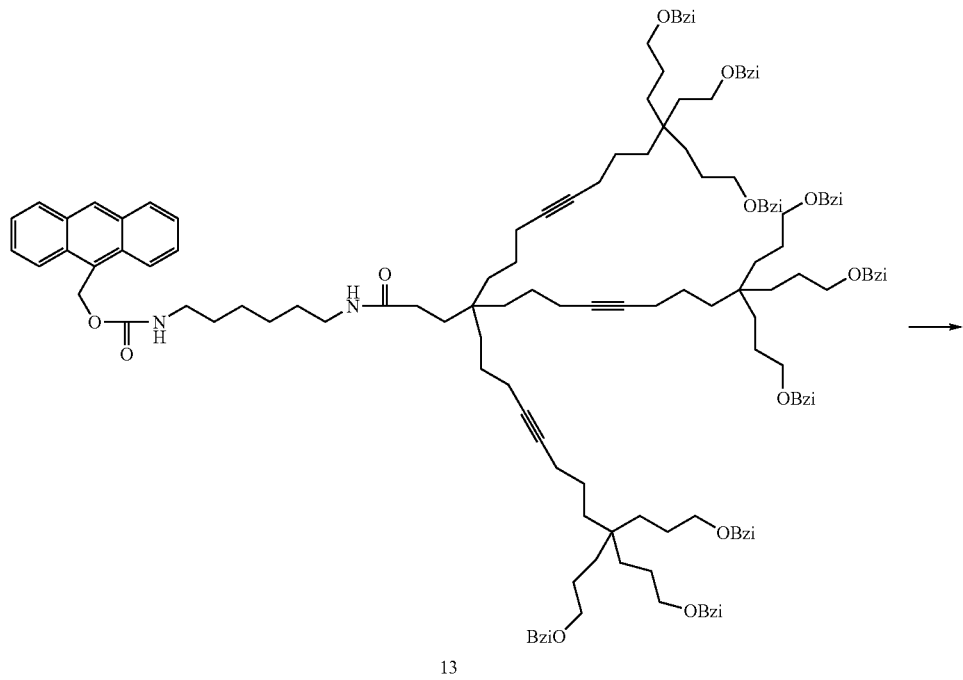
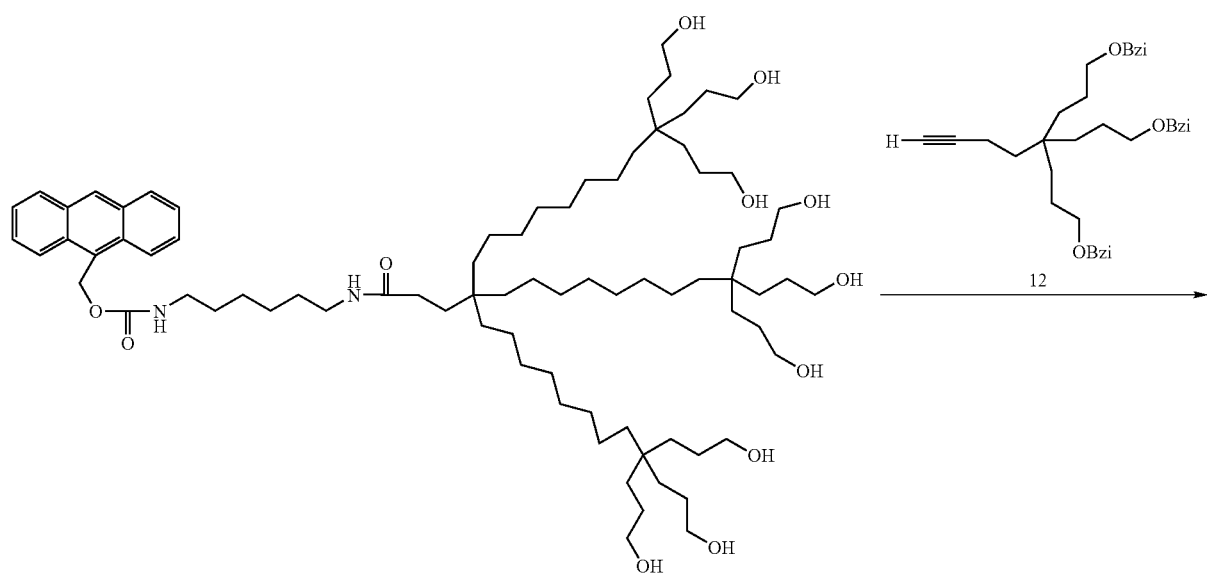

-continued
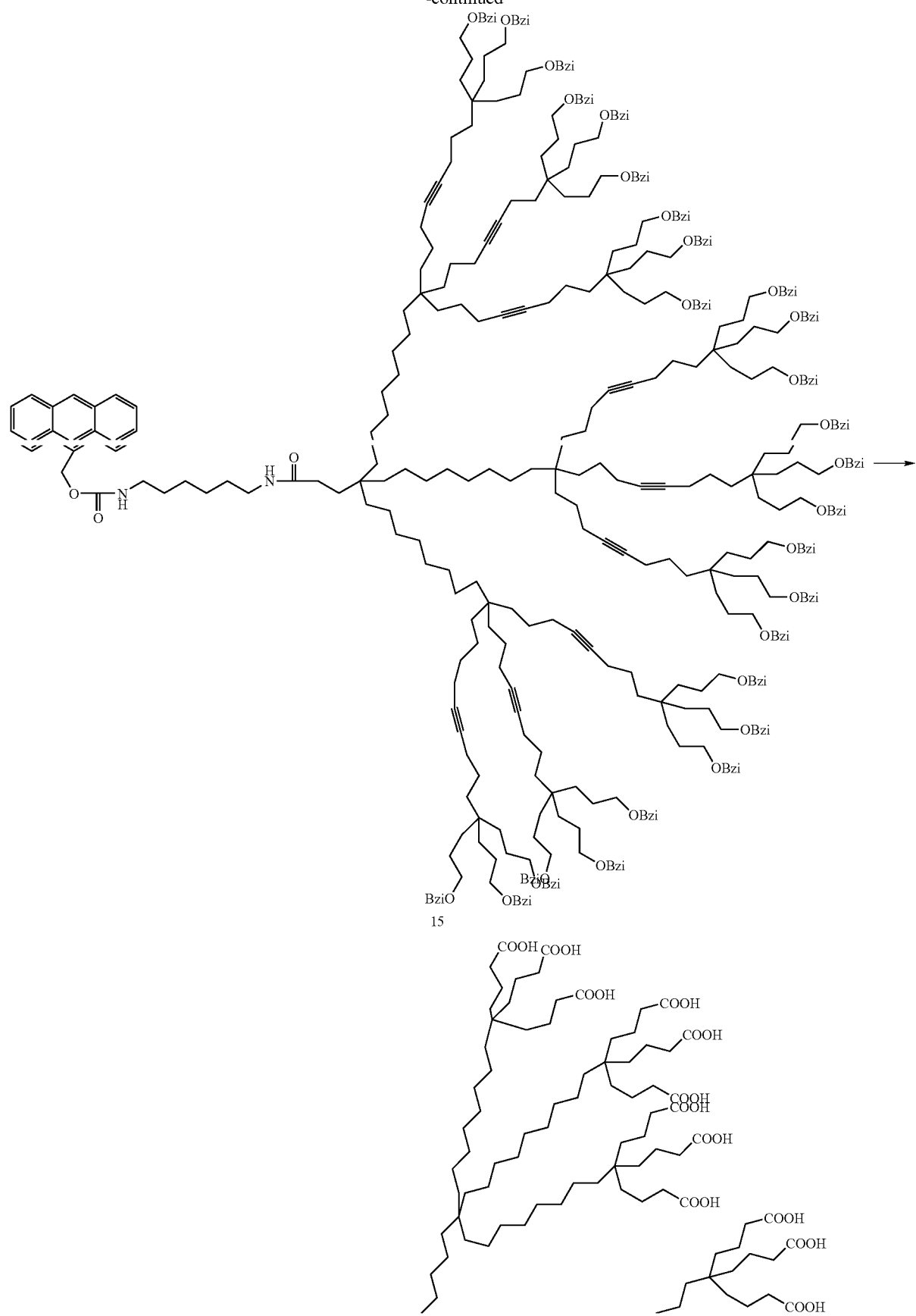
15

-continued

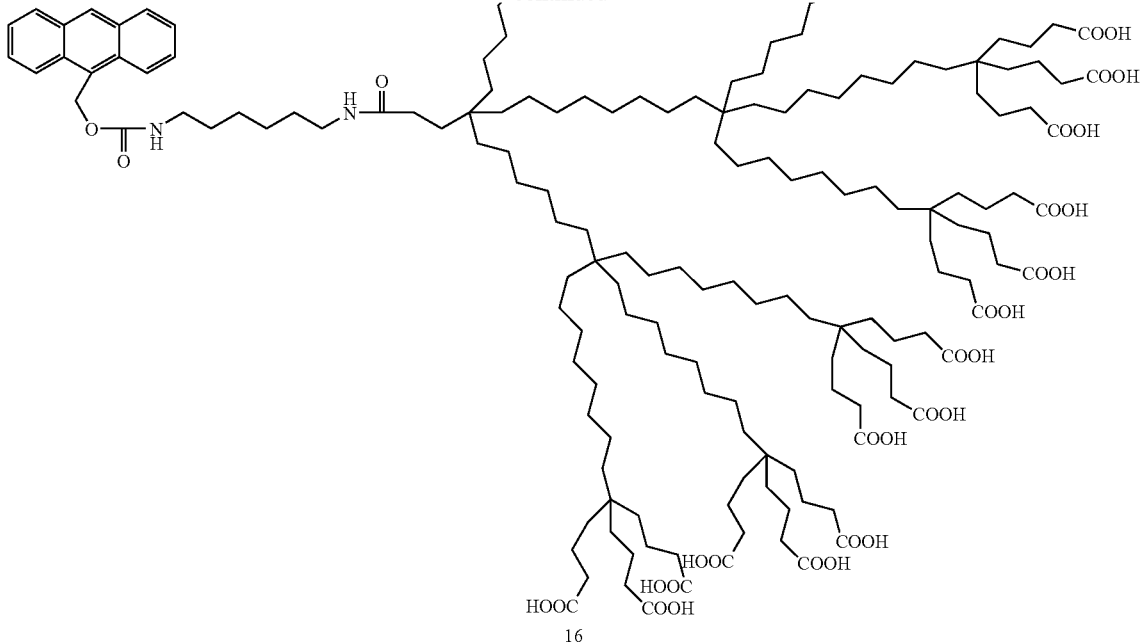

16

Hydrogenation of Compound 13 with 10% Pd—C under H$_2$ atmosphere in EtOH and THF at 60° C. for 4 d gave Compound 14. Compound 14 was converted to the corresponding bromide using SOBr$_2$ in CH$_2$Cl$_2$ at 40° C. for 12 h. The bromide compound was alkylated with 12 equivalents of Compound 12 to yield 49% of Compound 15. Compound 15 was reduced and deprotected in one step with 10% Pd—C under hydrogen atmosphere in EtOH and THF solution at 60° C. for 4 d to yield 89% of the corresponding alcohol, which was then oxidized with RuO$_4$ in the presence of NH$_4$OH or (CH$_3$)$_4$NOH to yield 85% of A-[27]-COOH (Compound 16).

Preparation of [G3]-(OH)$_8$

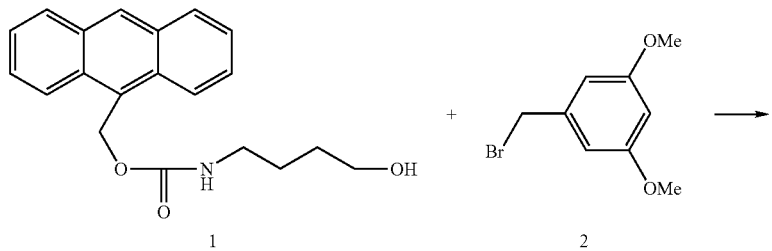

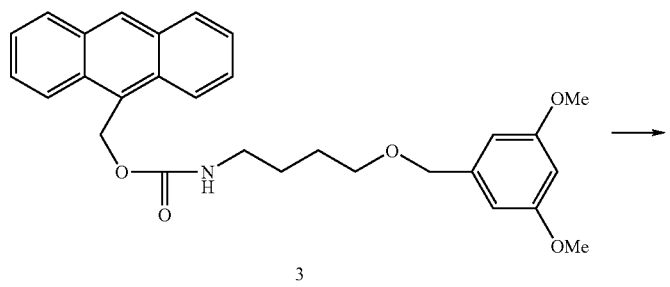

91 92
-continued
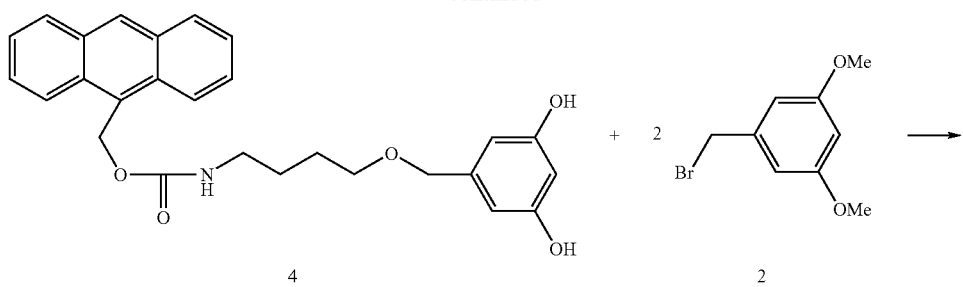
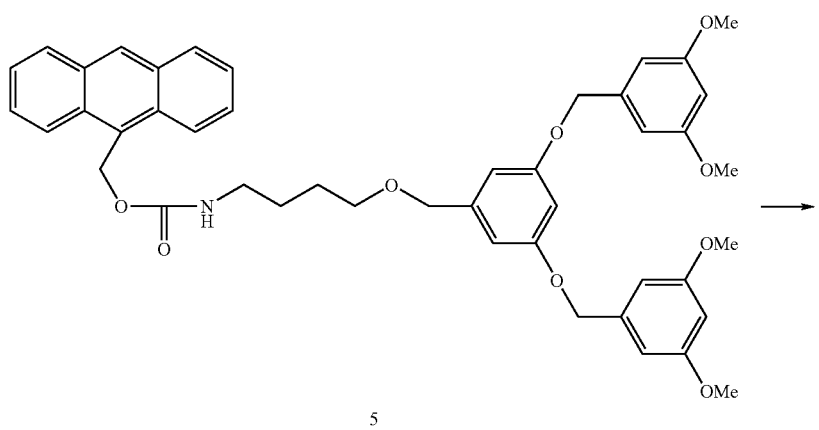
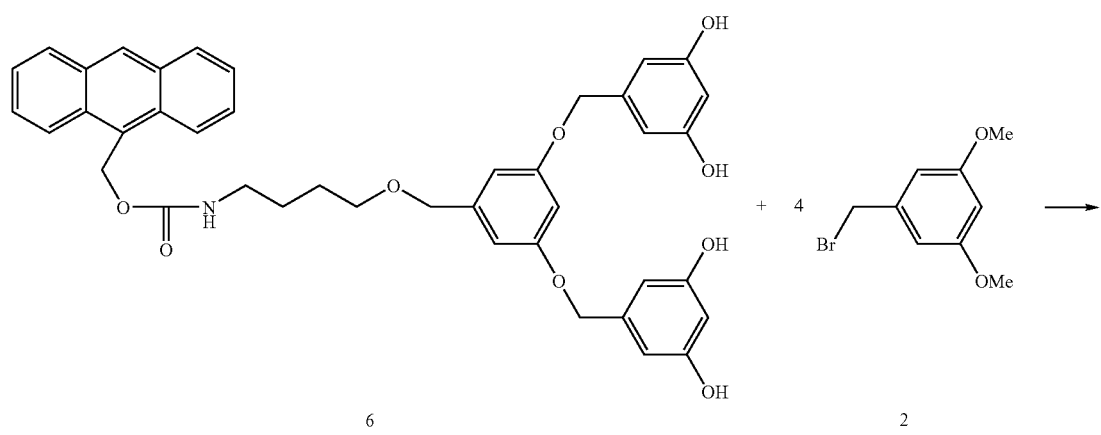

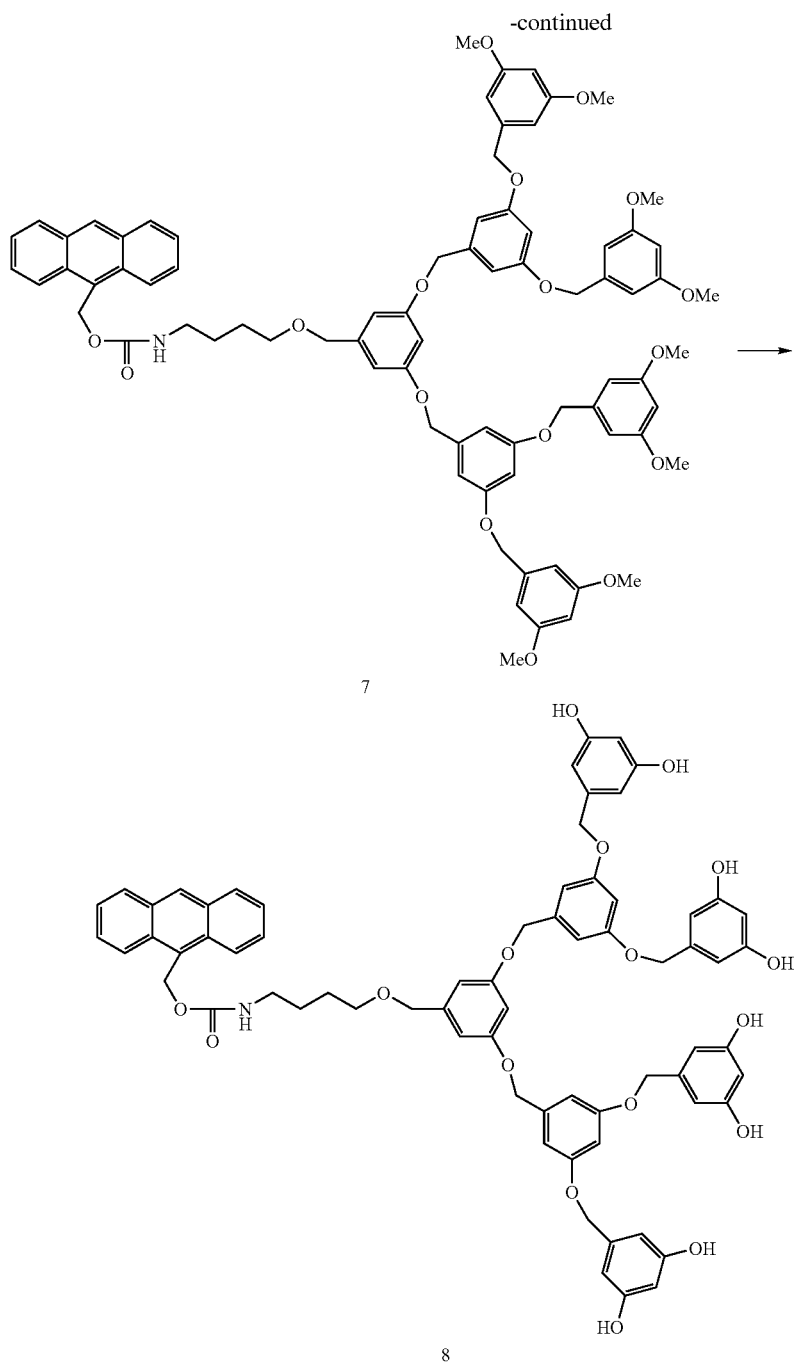

A mixture of compound 1 (1.05 mol equiv.), 3,5-dimethoxybenzyl bromide (1.00 mol equiv. 2), potassium carbonate (1.1 mol equiv.) and 18-c-6 (0.2 mol equiv.) in dry acetone was heated at reflux under nitrogen for 48 h. The mixture was cooled and evaporated to dryness, and the residue was partitioned between $CH_2Cl_2$ and water. The aqueous layer was extracted with $CH_2Cl_2$ (3×), and the combined organic layers were dried and evaporated to dryness. The crude product was purified by flash chromatography with EtOAc—$CH_2Cl_2$ as eluent to give compound 3. Methyl ether group of compound 3 was deprotected by $BBr_3$ in EtOAc solution for 1 h, and the crude product was purified by flash chromatography with MeOH-EtOAc as eluent to give compound 4.

A mixture of Compound 4 (1.00 mol equiv), 3,5-dimethoxybenzyl bromide (2.00 mol equiv), potassium carbonate (2.1 mol equiv) and 18-c-6 (0.2 mol equiv) in dry acetone was heated at reflux under nitrogen for 48 h. The mixture was cooled and evaporated to dryness, and the residue was partitioned between $CH_2Cl_2$ and water. The aqueous layer was extracted with $CH_2Cl_2$ (3×), and the combined organic layers were dried and evaporated to dryness. The crude product was purified by flash chromatography with EtOAc—$CH_2Cl_2$ as eluent to give compound 5. Methyl ether group of compound 5 was deprotected by $BBr_3$ in EtOAc solution for 1 h, and the crude product was purified by flash chromatography with MeOH-EtOAc as eluent to give compound 6.

A mixture of Compound 6 (1.00 mol equiv), 3,5-dimethoxybenzyl bromide (4.00 mol equiv), potassium carbonate (4.1 mol equiv.) and 18-c-6 (0.2 mol equiv.) in dry acetone was heated at reflux under nitrogen for 48 h. The mixture was cooled and evaporated to dryness, and the residue was partitioned between $CH_2Cl_2$ and water. The aqueous layer was extracted with $CH_2Cl_2$ (3×), and the combined organic layers were dried and evaporated to dryness. The crude product was purified by flash chromatography with EtOAc—$CH_2Cl_2$ as eluent to give compound 7. Methyl ether group of compound 7 was deprotected by $BBr_3$ in EtOAc solution for 1 h, and the crude product was purified by flash chromatography with MeOH-EtOAc as eluent to give [G3]-$(OH)_8$ (compound 8).

Assembly of the Dendrons on Solid Supports
General Materials and Instruments

The silane coupling reagents, (3-glycidoxypropyl)methyldiethoxysilane (GPDES) and (3-aminopropyl)diethoxymethylsilane (APDES), were purchased from Gelest, Inc. and all other reagents were reagent grade chemicals purchased from Sigma-Aldrich. Reaction solvents in Sure Seal bottles were purchased from Aldrich. All washing solvents for the substrates are of HPLC grade purchased from Mallinckrodt Laboratory Chemicals. The UV grade fused silica plates (30 mm×10 mm×1.5 mm) were purchased from CVI Laser Corporation. The polished prime Si(100) wafers (dopant, phosphorus; resistivity, 1.5-2.1 Ω·cm) were purchased from MEMC Electronic Materials, Inc. Glass slides (2.5×7.5 cm) were purchased from Corning Co. Oligonucleotides were purchased from Metabion. Ultrapure water (18 M Ω/cm) was obtained from a Milli-Q purification system (Millipore).

The film thickness was measured with a spectroscopic ellipsometer (J. A. Woollam Co. Model M-44). UV-vis spectra were recorded on a Hewlett-Packard diodearray 8453 spectrophotometer. Tapping mode AFM experiments were performed with a Nanoscope IIIa AFM (Digital Instruments) equipped with an "E" type scanner.

Cleaning the Solid Support

Solid supports such as oxidized silicon wafer, fused silica, and glass slide, were immersed into Piranha solution (conc. $H_2SO_4$:30% $H_2O_2$=7:3 (v/v)) and sonicated for an hour. The solid supports were then washed and rinsed with deionized water, and dried in a vacuum chamber.

Preparing the Hydroxylated Substrates

The cleaned solid supports were soaked in toluene solution of 10 mM of (3-glycidoxypropyl)methyldiethoxysilane (GPDES) for 2 hrs. After the self-assembly, the solid supports were washed with toluene and dried at 110° C. for 30 min. The solid supports were then sonicated and washed in dimethylformamide (DMF). GPDES-modified solid supports were soaked in a neat ethylene glycol (EG) solution at 120° C. for 2 hrs. After cooling, the solid supports were sonicated in water, washed with ethanol, and dried in a vacuum chamber.

Preparing the Dendron-Modified Solid Support

The hydroxylated solid supports were immersed into a methylene chloride solution containing the dendron (0.5 mM), 1-[-3-(dimethylamino)propyl]-3-ethylcarbodiimide hydrochloride (EDC) or 1,3-dicyclohexylcarbodiimide (DCC) (4.7 mM), and 4-dimethylaminopyridine (DMAP) (0.45 mM). After 2 hrs at room temperature, the plates were sonicated in ethanol and then washed with ethanol followed by xylene.

Preparing the Activated Solid Support

The dendron-modified solid supports were immersed into a solution of 0.1 M trifluoroacetic acid (TFA) in xylene. After 1 hr, they were washed with ethanol, and then soaked in a solution of 1% (v/v) triethylamine (TEA) in ethanol for 10 min. The solid supports were sonicated in ethanol, washed with water followed by ethanol, and dried in a vacuum chamber. The deprotected solid supports were incubated in 200 ml of acetonitrile solution including di(N-succinimidyl)carbonate (DSC) (900 mg) and DIPEA (200 ul). After 2 hrs, the solid supports were sonicated in ethanol for 2 min, washed briefly with ethanol, and dried in a vacuum chamber.

Aminosilylation with TMAC

A clean solid support (slide glass) was placed into a solution of TMAC (N-trimethoxysilylpropyl-N,N,N,-trimethylammonium chloride) (2 mL) and acetone (100 mL) for 5 h, after which it was removed from the solution, washed with acetone, and dried at 110° C. for 40 min. After immersion in acetone, the solid support was sonicated, washed, and dried under vacuum in a Teflon vessel.

Self-assembly of the Fmoc-(9)acid was performed using the procedure for the case of CBz-[9]-acid with the exception of capping of the residual amines by acetic anhydride.

Self-Assembly of the Fmoc-(9)Acid (5)

The Fmoc-spacer-(9)acid (5) was dissolved in a mixed solvent (DMF:deionized water=1:1 (v/v)). The above prepared aminosilylated slide glass was placed in the solution. Each piece of the solid support was taken out of the solution after 1 day and washed with a copious amount of deionized water. Each solid support was sonicated successively in deionized water, a mixture of deionized water-methanol (1:1 (v/v)) and methanol, and then dried under vacuum.

Deprotection of Fmoc from the Self-Assembled Fmoc-(9) acid (5)

The self-assembled solid support was immersed in a solution of 5% piperidine in DMF for 20 min. Each solid support was sonicated successively in acetone and MeOH, and dried under vacuum.

Aminosilylated CPGs, Reagents, and Instruments

Aminopropyl group tethered controlled pore glass beads (AMPCPG; 80-120 mesh; mean pore diameter, 50 nm or 300 nm) and controlled pore glass beads modified with a long chain aminoalkyl group (LCAA-CPG; 80-120 mesh; mean pore diameter, 50 nm) were purchased from CPG, Inc. 1,4-Butanediol diglycidyl ether, 1,3-diaminopropane, reduced glutathione (GSH), N-(3-methylaminopropyl)-N'-ethylcarbodiimide (EDC), N-hydroxysuccinimide (NHS), N-(9-fluorenylmethoxycarbonyloxy)chloride (Fmoc-Cl), piperidine, 4-maleimidobutyric acid N-hydroxysuccinimide ester (GMBS), phosphate buffered saline tablets (PBS) were obtained from Sigma-Aldrich. All other chemicals were of analytical reagent grade and were used without further purification. Deionized water (18 MΩ·cm) was obtained by passing distilled water through a Barnstead E-pure 3-Module system. UV-vis spectra were recorded on a Hewlett-Packard diode-array 8453 spectrophotometer.

Self-Assembly of Fmoc-(3)Acid

AMPCPG (dry weight 0.70 g) was washed with acetone with a glass filter. After drying in vacuum, a mixture of 1,4-butanediyl diglycidyl ether (1.0 mL) and carbonate buffer solution (2.0 mL, pH=11) was added to AMPCPG (surface capacity: 91.8 μmol/g, surface area: 47.9 m2/g). After shaking for 24 h at room temperature, the resulting beads were separated from the solution by filtration and washed with deionized water and subsequently with acetone. Then a vial containing this sample was shaken with a mixture of 1,3-diaminopropane (1.0 mL) and carbonate buffer solution (pH=11) for 24 h at room temperature. After washing, a mixture of 2-mercaptoethanol (1.0 mL) and aqueous sodium bicarbonate solution (2.0 mL, pH=8.5) was used for blocking the residual epoxy group on the surface. Subsequently, an aqueous solution of dimethylformamide (30% DMF (v/v)) dissolving Fmoc-(3)acid (14 mg, 21.3 µmol), N-(3-methylaminopropyl)-N'-ethylcarbodiimide (15 mg, 77 µmol) and N-hydroxysuccinimide (9.0 mg, 77 µmol) was introduced into a vial containing the beads. After shaking for 11 h at room temperature, the beads were washed with deionized water and subsequently with acetone.

Blocking Step:

Acetic anhydride (1.0 mL) in anhydrous methylene chloride (2.0 mL) was allowed to react with the residual amine overnight at room temperature.

Deprotection Step:

After washing the beads with methylene chloride and subsequently with acetone, 20% piperidine in DMF (3.0 mL) was added in a vial holding the beads, and the vial was shaken for 30 min.

DNA Microarray Assay with Model System: Experimental Protocols

Instruments

Oligonucleotides were spotted using QArrayMini (Genetix) or Piezorray (PerkinElmer LAS). Hybridization was performed with HS400 or HS4800 (TECAN). The fluorescence signal of the microarrays was measured with both ScanArray Lite (GSI Lumonics) and GenePix Personal 4100A (Molecular Devices), and the images were analyzed with an Imagene 4.0 software (Biodiscovery).

Probe Oligonucleotides

Amine-tethered probe oligonucleotides (probes 1 and 2 in FIG. 2c) were used to examine single nucleotide polymorphism (SNP) discrimination efficiency of DNA microarrays. Probe and target oligonucleotides utilized in this work were shown in FIG. 2c.

Fabrication of Oligonucleotide Arrays on the Dendron-Modified Slides

Probe oligonucleotides (20 µM) in a spotting buffer solution [25 mM NaHCO$_3$, 5.0 mM MgCl$_2$ and 10% DMSO (pH 8.5)] were printed on the activated dendron-modified slides using a microarrayer, and the spots were arranged to make a 4×4 format. The microarrays were incubated in a humidity chamber (80% humidity) for half a day to give the amine-tethered oligonucleotides sufficient reaction time. The slides were then placed in a stirred hybridization buffer solution [2×SSPE buffer (pH 7.4) dissolving 7.0 mM SDS] at 37° C. for 10 min to remove non-specifically bound oligonucleotides. Finally, the DNA-immobilized slides were dried under a stream of nitrogen and stored at 4° C. for the next step.

Fabrication of Oligonucleotide Arrays on the Conventional Slides

Purchased silanated slides were incubated in a mixed solvent [DMF/pyridine 90:10 (v/v)] dissolving 1,4-phenylenediisothiocyanate (PDITC) linker (12.5 mM). After reaction for 2 h, the plates were sonicated three times each in methanol and acetone in a sequential manner. The washed plates were dried in a vacuum chamber. Probe oligonucleotides dissolved in sodium carbonate/bicarbonate buffer solution (100 mM, pH 9.0) were printed on the PDITC-modified slides with a microarrayer, and the spots were arranged to make a 4×4 format. The slides were incubated in a saturated humidity chamber at 37° C. for 1 h to immobilize the amine-tethered oligonucleotides. The slides were then soaked in 1% NH$_4$OH aqueous solution for 3 min. Finally, the DNA-functionalized slides were washed with deionized water several times and dried under a stream of nitrogen.

Hybridization

A hybridization solution including a target oligonucleotide (10 nM) tagged with a Cy$_3$ fluorescent dye was prepared by dissolving in the hybridization buffer solution [2×SSPE buffer (pH 7.4) dissolving 7.0 mM SDS]. The printed slide was placed in a hybridization chamber of an automatic hybridization machine (HS400), and then the prepared target DNA solution was injected into the chamber at 45-50° C. After 1 h incubation at 45-50° C., the slide was washed with the hybridization buffer solution at 45-50° C. for 3 min followed by with 0.2×SSC buffer solution or 1×PBS buffer solution at 25° C. for 10 sec. Finally, the slide was dried under a stream of nitrogen for further scanning and analysis. For each hybridization experiment, 100 µl volume of a target DNA solution was utilized.

DNA Microarray Assay with Model System: Results

The DNA microarrays were fabricated to evaluate the discrimination efficiency between a complementary pair (A:T) and three internal single-base mismatched pairs (T:T, G:T, C:T), and for comparison, different kinds of probes were spotted in a single plate.

For hybridization, a 15-base oligonucleotide (Target 1) or 45-base oligonucleotide (Target 2) was used (FIG. 2c). Hybridization was performed in the above washing buffer solution containing a target oligonucleotide (10 nM) tagged with a Cy3 fluorescent dye at 45-50° C. for 1 h using a HS400 (TECAN). The fluoresecnce signal on each spot was measured with a ScanArray Lite (GSI Lumonics) and analyzed by Imagene 4.0 (Biodiscovery).

In the case of the 15-base target oligonucleotide, there was a dramatic difference in the intensity between the matched and the internal mismatched pairs. The normalized fluorescence signal ratios (or intensity ratios for one base internal-mismatched pair versus the perfectly matched pair, i.e., MM/PM) were 0.005, 0.008, and 0.006 (T:T, G:T, and C:T internal mismatches) (Table 2). The observed selectivity was significantly improved over conventional methods, and a large increase of the selectivity (20~82 times) was recorded in comparison with DNA microarrays on the generic surface (Table 2).

TABLE 2

| | Normalized fluorescence signal ratio | | | |
|---|---|---|---|---|
| | Matched (A:T) | Mismatched (T:T) | Mismatched (G:T) | Mismatched (C:T) |
| Dendron-modified surface, 15-mer (Target 1 & Probe 1) | 1 | 0.005 | 0.008 | 0.006 |
| Dendron-modified surface, 45-mer (Target 2 & Probe 1) | 1 | 0.006 | 0.009 | 0.009 |
| APDES-modified surface, $C_6$ spacer (Target 1 & Probe 1) | 1 | 0.41 | 0.38 | 0.26 |
| APDES-modified surface, $(T)_{30}$ spacer (Target 1 & Probe 2) | 1 | 0.17 | 0.18 | 0.12 |

When a 45-base target oligonucleotide was used the MM/PM ratios for T:T, G:T, and C:T internal mismatches were 0.006, 0.009, and 0.009 (Table 2). This result shows that outstanding selectivity holds for the longer target oligonucleotides. Without being bound by any theory, it is believed that the efficacy of this DNA microarray is due in part to spacing between immobilized DNA strands by dendrons.

A selectivity of DNA microarray fabricated on a solid support modified with (3-aminopropyl)diethoxymethylsilane (APDES) was tested using the same procedure and oligonucleotides as those for the dendrimer polymer-modified DNA microarray, except for the use of 1,4-phenylene-diisothiocyanate (PDITC) linker. The observed MM/PM ratios for T:T, G:T, and C:T for APDES-modified surface were 0.41, 0.38, and 0.26 (Table 2). Use of DSC linker on the APDES-modified substrate resulted in high coefficient variance (CV) value (>20%), which represents the degree of variation among the spots, and non-uniform fluorescence intensity within each spot.

For additional comparison, probe 2 oligonucleotides having an extra $(T)_{30}$ spacer at the 5' end of oligomer were utilized for SNP discrimination test. For this case, the probe with the extra spacer was immobilized on an APDES-modified glass surface. The observed MM/PM ratios for T:T, G:T, and C:T cases were 0.17, 0.18, and 0.12 (Table 2). The selectivity was significantly enhanced in comparison with the case of probe DNA with a $C_6$ spacer, but still was largely inferior to the dendron-modified DNA microarray.

Hybridization on the surface poses various complications, hurdles to control and predict the microarray's screening performance precisely. Non-specific binding, steric and electrostatic effects, and environmental changes during the washing process should be considered in addition to the melting temperature (Tm) of the duplex and the Gibbs free energy for the duplex formation. Difference between the Gibbs free energy of the internal-mismatched pairs (T:T, G:T, and C:T internal mismatches of the 15-mer) and that of the perfectly matched pair in solution is 2.67, 1.75, and 3.05 kcal/mol at 50° C. Gibbs free energy was calculated with $H_yT_{HER}$™ Software (http://ozone2.chem.wayne.edu). Therefore, the theoretical fluorescence ratios (MM/PM) are 0.016, 0.065, and 0.009 respectively. Also, study in solution phase with a molecular beacon showed that in some instances SNP discrimination ratio was as low as 1:0.01 (see, for example, Taton et al., Science 289, 1757-1760 (2000)). These data show that in some instances dendron-modified DNA microarray of the present invention reaches or even surpasses the thermodynamic limit. In particular, for the G:T case, the discrimination efficiency in the microarray format is better than the value calculated for the solution phase.

p53 DNA Microarray Assays: Experimental Protocols
Instruments

Oligonucleotides were spotted using QArrayMini (Genetix) or Piezorray (PerkinElmer LAS). Hybridization was performed with HS400 (TECAN) or G2534A microarray hybridization chamber (Agilent Technologies). The fluorescence signal of the microarrays was measured with both ScanArray Lite (GSI Lumonics) and GenePix Personal 4100A (Molecular Devices), and the images were analyzed with an Imagene 4.0 software (Biodiscovery).

Probe Oligonucleotides

Seven codons, 175, 215, 216, 239, 248, 273, and 282 in a p53 gene, which are known to be missense mutational hotspots with unusually high frequency were selected for this study. Codons 175, 248, 273, and 282 were taken from the international TP53 mutation database (IARC, http//:www-p53.iarc.fr/p53DataBase.htm) and the other three codons 215, 216, and 239 were taken from Korean p53 mutational hotspot database. The capture probe sequences (the DNA immobilized on dendron-modified solid support surface) for seven codons were designed by software and their lengths were 15-23 mer varied from codon to codon to set $T_m$ to around 55° C. (Table 3).

TABLE 3

| | | | Capture oligonucleotides used in this study | |
|---|---|---|---|---|
| No | Probe name | Exon | Sequence[a] (5'→3') | Nucleotide |
| 1 | 175 | 5 | GTTGTGAGG<u>CNC</u>TGCCCC N = G (wt), A, T, C (mt) | 18 |
| 2 | 215 | 6 | TTTCGACAT<u>ANT</u>GTGGTGGTG N = G (wt), A, T, C (mt) | 21 |
| 3 | 216 | 6 | TCGACATAGT<u>NTG</u>GTGGTGCC N = G (wt), A, T, C (mt) | 21 |
| 4 | 239 | 7 | CATGTGT<u>NAC</u>AGTTCCTGCA N = A (wt), G, T, C (mt) | 20 |
| 5 | 248 | 7 | CATGAAC<u>NGG</u>AGGCCCATC N = C (wt), A, T, G (mt) | 19 |

TABLE 3-continued

Capture oligonucleotides used in this study

| No | Probe name | Exon | Sequence$^a$ (5'→3') | Nucleotide |
|----|------------|------|----------------------|------------|
| 6 | 273 | 8 | TTGAGGTGCNTGTTTGTGC N = G (wt), A, T, C (mt) | 19 |
| 7 | 282 | 8 | GAGAGACNGGCGCACAG N = C (wt), A, T, G (mt) | 17 |
| 8 | 175-T30 | 5 | (T)$_{30}$-GTTGTGAGGCNCTGCCCC N = G (wt), A, T, C (mt) | 48 |
| 9 | 239-T30 | 7 | (T)$_{30}$-CATGTGTNACAGTTCCTGCA N = A (wt), G, T, C (mt) | 50 |

The sequences underlined represent the codons as numbered under 'Probe name'.
wt, wild type;
mt, mutant type.
$^a$The oligonucleotides have an amino group at the 5' end.

Fabrication of p53 DNA Microarrays

A p53 DNA microarray was fabricated by printing each probe solution including each 20 μM amine-tethered probe oligonucleotide, 25 mM sodium bicarbonate, 5 mM MgCl$_2$ and 10% (v/v) dimethyl sulfoxide at pH 8.5 on the activated dendrimeric polymer-modified slide using a microarrayer. After printing the probe oligonucleotides side by side in a 10×1 format, the microarray was incubated in a chamber maintained at ~80% humidity for overnight to give the amine-tethered DNA sufficient reaction time. Slides were then stirred in a buffer solution containing 2×SSPE (0.30 M sodium chloride, 0.020 M sodium hydrogen phosphate and 2.0 mM EDTA), pH 7.4 and 7.0 mM SDS at 37° C. for 10 min, and then briefly washed with water to remove non-specifically bound oligonucleotides. Finally, the DNA-functionalized microarray was dried under a stream of nitrogen for the subsequent hybridization. Different kinds of probes were spotted in a single plate.

Genomic DNA Samples

Genomic DNAs of SNU-cell lines (SNU-61, 216, 475, 563, 601, 668, 761, and 1040) were obtained from Jae-Gab Park, College of Medicine in Seoul National University. The provided SNU-cell lines were human carcinoma cell lines from individual Korean patients.

Subcloning and Sequencing p53 genes, especially between exon 5 and exon 8, for each cell lines were amplified by PCR with 2 pairs of synthetic oligonucleotide primers: Exon 5 Fwd I, 5'-CTG ACT TTC AAC TCT GTC TCC T-3'; Exon 5 Fwd II, 5'-TAC TCC CCT GCC CTC AAC AA-3'; Exon 8 Rev I, 5'-TGC ACC CTT GGT CTC CTC CAC-3'; Exon 8 Rev II, 5'-CTC GCT TAG TGC TCC CGG G-3'. Each genomic DNA was amplified with 10 pmoles of first primer pair (exon 5 Fwd I and Exon 8 Rev I, corresponding to intron 4 and intron 8), 250 μM dNTP mix, 2.5 U Taq polymerase (NEB) in 1× ThermoPol buffer (supplemented with Taq polymerase) for 20 μL of total reaction volume in Multiblock System (Hybaid, UK) using the following settings: initiation activation of the polymerase at 95° C. for 1 minute, then 20 cycles of 95° C. for 30 sec, 58° C. for 30 sec, 72° C. for 90 sec, followed by final elongation step at 72° C. for 5 min. First PCR products were diluted and used as template for second PCR. The amplified genomic DNA PCR products were diluted 20 fold and used for the second nested PCR under the same conditions as the previous step except PCR was performed with 10 pmoles of the second primer pair (exon 5 Fwd II and exon 8 Rev II, corresponding to exon 5 and exon 8) and the cycle for amplification was increased to 25 cycles. The final nested PCR products were purified by gel extraction method. PCR products from genomic DNA were ligated into pGEM T-easy vector (Promega) and transformed to DH5a cells. Subcloned plasmid was purified by QIAGEN Plasmid Min kit (QIAGEN Inc., Valencia, Calif.) for sequencing analysis. Bidirectional sequencing was performed using pUC/M13 Forward and Reverse Sequencing Primer as follows: M13 FWD 5'-GTT TTC CCA GTC ACG ACG TTG-3' and M13 REV 5'-TGA GCG GAT AAC AAT TTC ACA CAG-3'.

Preparation of Target DNAs

DNA targets spanning SNP sites were randomly primed and labeled in a Multiblock System (Hybaid, UK) using 32 ng of template DNA with 5 U Klenow enzyme (NEB), 1× reaction buffer supplemented with Klenow enzyme, 6 μg of random octamer (synthesized by Bionics), low dT dNTP mix (100 μM dA,G,CTP/50 μM dTTP) and 50 μM Cyanine-3-dUTP (NEN) in 20 μl of total reaction volume at 37° C. for 2 hours. Optionally, randomly primed target DNAs can be purified by QIAGEN MinElute PCR purification kit (QIAGEN Inc., Valencia, Calif.). After quantitative and qualitative (specific activity, number of nucleotide per an incorporated fluorescent dye) analysis using UV/Vis spectrophotometer, qualified products were used for hybridization.

Manual Hybridization

A target DNA solution, 200 μl was prepared by mixing 20 μl of the above prepared target DNAs and 180 μl of the hybridization buffer solution [2×SSPE buffer (pH 7.4) dissolving 7.0 mM SDS], and the solution was denaturized at 95° C. for 3 min using a heat block machine. After heating, the solution was immediately loaded on a gasket slide (cat. no. G2534-60002, Agilent Technologies), and then the microarray hybridization chamber (cat no. G2534A, Agilent Technologies) was assembled by following a user guide provided by the manufacturer. Next, the chamber was placed and rotated in a hybridization oven at 50° C. After 4 hrs hybridization, the slide was washed with the hybridization buffer solution at 50° C. for 3 min followed by with 0.2×SSC buffer solution at room temperature for 10 sec, and finally was dried by using a nitrogen gas dispenser or a slide centrifuge for further scanning and analysis.

Automatic Hybridization

A target DNA solution, 100 μl was prepared by mixing 20 μl of the above prepared target DNAs and 80 μl of the hybridization buffer solution [2×SSPE buffer (pH 7.4) dissolving 7.0 mM SDS]. The printed slide was placed in a hybridization chamber of an automatic hybridization machine (HS400), and then the above prepared target DNA solution was injected into the chamber. After the chamber was heated at 90° C. for 1 minute, it was incubated at 50° C. for 4 hrs. A built-in denaturation function of the machine works for better hybridization performance. After the hybridization, the slide was washed with the hybridization buffer solution at 50° C. for 3 min followed by with 0.2×SSC buffer solution at 25° C. for 10 sec. Finally, the slide was dried under a stream of nitrogen for further scanning and analysis.

p53 DNA Microarray Assays: Results
Detection of 7 Hot Spot Mutations of P53 Gene Using Single Dendron-Modified Surface In biological systems, the p53 tumor-suppressor gene plays key roles in cell regulation, gene transcription, genomic stability, DNA repair, and apoptosis. Loss of wild-type function of p53 can lead to cancer, and it is believed that p53 mutations are the most frequent genetic changes in human cancer such as colon, and lung cancer.

DNA microarrays on [9]-acid dendron-modified solid supports were applied to the detection of single mutation of p53 tumor suppressor gene in cancer cell line. Target DNA samples (~200-400 bases) which contain 175 codon were prepared by random priming the genomic DNA templates and allowed to hybridize with dendron-modified solid slides on which 18mer probe oligonucleotides had been immobilized in a 10 by 1 format. The MM/PM ratio for A:C, T:C, and C:C internal mismatches were 0.028, 0.031, and 0.007. This result shows that the outstanding selectivity holds for real target DNAs.

The DNA microarrays on [27]-acid dendron-modified solid supports were prepared using the same method as in the case of [9]-acid dendron as described above and applied to the detection of single mutation of 175 codon of p53 tumor suppressor gene. The MM/PM ratio for A:C, T:C, and C:C internal mismatches were 0.066, 0.01, and 0.005. This result indicates that the DNA microarrays on [27]-acid dendron-modified solid supports also show outstanding selectivity for the detection of single mutation of target DNAs.

The dendron-modified solid supports were applied to the detection of single mutation of p53 tumor suppressor gene in cancer cell line. Target DNA samples (200-400 mer) which span 7 hot spot codons (175, 215, 216, 239, 248, 273, and 282) were prepared by random priming the DNA templates which cloned from cancer cell line and allowed to hybridize with the probe oligonucleotides corresponding to the 7 hot spot codons that had been immobilized on the dendron-modified slide. The fluorescence intensity of each hybridized spot was determined with a scanner and the SNP discrimination efficiency was calculated. In conclusion, excellent SNP discrimination efficiency was obtained.

Effect of Length of Probe Oligonucleotide with T30 on Hybridization Efficiency and SNP Discrimination The effect of the length of capture probe for the SNP discrimination efficiency was tested by varying the length of capture probes with T30. After immobilizing capture oligonucleotides corresponding to codons 175 and 239 containing T30 by linking the 5' end of the specific sequence and the terminal primary amino group on dendron-modified surface, p53 target DNA was hybridized and fluorescence intensity was measured. This study shows dependence of the SNP discrimination efficiency and signal intensity on the length of the capture probe.

Concentration of Capture Probe Vs. Intensity; and Concentration of Capture Probe Vs. SNP Discrimination Dependence of signal intensity and SNP discrimination efficiency on the concentration of capture probes was investigated. Capture probes on dendron-modified solid support surface, at various concentrations, were allowed to hybridize with target DNA and the fluorescence intensity and SNP discrimination efficiency were determined. Optimal concentration of capture probe for p53 was determined.

Concentration of Target Probe Vs. Intensity; and Concentration of Target Probe Vs. SNP Discrimination Dependence of signal intensity and SNP discrimination efficiency on the concentration of target probes was investigated. Target DNAs of various concentrations were applied to hybridization and the fluorescence intensity and SNP discrimination efficiency were determined.

Detection of Mutation in Mixed Target Samples

Point mutations with target samples in which the mutated target sequences exist in a small portion compared with normal sequence (5 or 10%) can be detected. Samples containing two kinds of target DNAs were prepared with different molar ratio and used for hybridization to detect single point mutation in certain codon in mixtures of normal as well as mutated target DNA. Such test can be used for various clinical diagnostic assays, for example, for detecting cancer.

Effect of Length of Target Probe on Hybridization Efficiency and SNP Discrimination By preparing different lengths of target DNAs by several different methods such as random priming, PCR, and DNase degradation the effect of length of target probe on hybridization and SNP discrimination efficiency was investigated.

Detection of 7 Hot Spots Mutation in Ten Unknown Colon Cancer Cell Lines

Methods and compositions of the invention were used to detect mutations in unknown cancer cell lines.

The colon cancer cell lines SNU-C1, SNU-C5, COLO 201, COLO 205, DLD-1, LS 513, HCT-15, LS 174T, HCT 116, and SW480 were purchased from KCLB (Korea Cell Line Bank, Seoul, Korea). Cells were cultured in RPMI 1640 supplemented with 10% fetal bovine serum (FBS), 100 µg/mL streptomycin and 100 U penicillin (GibcoBRL, Carlsbad, Calif.) and incubated in 5% $CO_2$ at 37° C. The colon cancer cells ($2\times10^6$ cells) were harvested for genomic DNA extraction by Invisorb® spin cell mini kit (Invitek, Berlin, Germany) following the manufacturer's instructions. From these genomic DNAs, p53 target DNAs were prepared and DNA microarray experiment were performed using the same procedure described above.

Fixing Protein Probe on Dendron-Modified Surface
Arraying NHS-Biotin to Dendron-Modified Slide Glass Spotting solution of succinimidyl D-biotin (1.0 mg) in 1 mL sodium bicarbonate buffer 50 mM and DMSO (40% v/v) was prepared. The solution including NHS-biotins was printed onto the dendron-modified slide glass using a Microsys 5100 microarrayer (Cartesian Technologies, Inc, USA) in a class 10,000 clean room. After 1 h incubation in a humidified chamber (~75% humidity), the biotin-immobilized microarrays were sequentially washed with DMF, THF, and MBST (50 mM MES, 100 mM NaCl, 0.1% Tween-20, pH 6.0). Finally, the arrays were rinsed with water, dried, and either used immediately or stored at room temperature for several days.

Detection of Protein/Ligand Interactions

The method according to Hergenrother, P. J.; Depew, K. M.; Schreiber, S. L. J. Am. Chem. Soc. 2000, 122, 7849 was followed. Before adding Cy3-labeled streptavidin solution, the slides were blocked for 1 h with MBST supplemented with 3% bovine serum albumin (BSA). After a brief rinse, the slides were exposed to Cy3-labeled streptavidin solution for 30 min at room temperature. This solution was prepared by diluting stock solutions of the appropriate protein(s) with MBST supplemented with 1% BSA at a concentration of 1 µg/mL. After incubation, the slides were rinsed once with MBST and then gently agitated with four changes of MBST over the course of 12 min. The slides was dried and scanned using a commercial confocal laser scanner, ScanArray® Lite (GSI Lumonics). Quantitative microarray analysis software, ImaGene (BioDiscovery, Inc.) was used for image acquisition and fluorescence intensity analysis.

Dendron-Modified CPG (Sample E1 and E3): Experimental Protocols

Ligand-Immobilization Step

A mixture of 1,4-butanediyl diglycidyl ether (1.0 mL) and carbonate buffer solution (2.0 mL, pH=11) was added into the vial, and the mixture was shaken for another 24 h at room temperature. After washing the beads with deionized water and subsequently with acetone, the reduced glutathione (GSH, 5.4 mg, 17.6 µmol) in sodium bicarbonate solution (3.0 mL, pH 8.5) was added into a vial containing the beads, and the vial was shaken for 12 h at room temperature. After washing the beads, a mixture of 2-mercaptoethanol (1.0 mL) and aqueous sodium bicarbonate solution (2.0 mL, pH=8.5) was added into the vial containing the beads. Finally, the beads were separated, washed, dried in vacuum, and stored at 4° C. under dry nitrogen atmosphere. The same steps were followed exactly to prepare the sample E3 as described above, except that Fmoc-(9) acid was used instead of Fmoc-(3) acid.

Preparation of Conventional GSH Tethered Matrices for Control Experiment (Sample CS, CL, and A)

Sample CS and CL:

GSH was immobilized directly on both AMPCPG and LCAA-CPG through GMBS linker. The beads (0.10 g) were washed with acetone with a glass filter. After drying in vacuum, a mixture of sodium bicarbonate buffer (1.0 mL, 3:7 (v/v), pH=8.5) and 4-maleimidobutyric acid N-hydroxysuccinimide ester (GMBS, 3.0 mg, 11 µmol) in DMF was added into a vial containing the beads. After four hours of shaking at room temperature, the resulting beads were separated from the solution by filtration and washed with deionized water and subsequently with acetone. Finally, acetic anhydride (1.0 mL) in anhydrous methylene chloride (2.0 mL) was allowed to react with residual amine group on the matrix. After washing, glutathione (GSH, 3.4 mg, 11 µmol) in PBS buffer (1.0 mL) was added into a vial containing the beads, and the vial was shaken for 12 h at room temperature. After 2-mercaptoethanol (1.0 mL) was used to block the residual maleimido group, the beads were separated, washed, dried in vacuum.

Sample A:

The same modification steps for E1 and E3 were followed to modify AMPCPG with 1,4-butanediyl diglycidyl ether and 1,3-diaminopropane. After the capping with 2-mercaptoethanol, 1,4-butanediyl diglycidyl ether was used to generate an epoxy group. Finally, glutathione was immobilized, and 2-mercaptoethanol was used to open the remaining epoxy group on the beads.

Determination of Amine Density on the Modified Beads

Either modified beads on the way to E1 or E3 or beads for control experiments (10 mg) were taken into an e-tube. In parallel, 9-fluorenylmethyl chloroformate (Fmoc-Cl, 1.75 mg) and $Na_2CO_3$ (1.45 mg) were placed into a separate glass vial, and a mixed solvent (2:1 (v/v) 1,4-dioxane and water, 2.5 mL) was added. One fifth of the solution was taken and transferred into the e-tube containing the beads. The tube was placed into a vial, and the vial was shaken for 12 h at room temperature. The beads were separated with a glass filter, and the porous materials were washed with deionized water and subsequently with acetone. After drying in vacuum, 20% piperidine in DMF (0.50 mL) was added into an e-tube containing the beads. The beads were allowed to react with piperidine for 30 min. Then the resulting solution from the tube was transferred carefully into a new e-tube, and the beads were washed with 20% piperidine in DMF (0.25 mL) twice. The solution was then added to the previous e-tube. The resulting solution was mixed with methanol to adjust the absorbance. The absorbance at 301 nm was measured using a U/V/Vis spectrometer, and a relevant solvent was used for the background correction. To increase reliability, the measurements were carried out with five different samples.

For calibration, a series of N-Fmoc-ethanolamine (or 9-fluorenylmethyl N-(2-hydroxyethyl)carbamate) (30 µM-70 µM), 20% piperidine in DMF solutions were prepared. After allowing 30 min for the reaction, a solution containing dibenzofulvene was utilized for measuring absorbance, and calculating the absorption coefficient.

Preparation of GST Fusion Protein Lysate

GST-fusion proteins were prepared as described in *Biochemistry*, 2002, 41, 3414-3421. For large scale cultures, the single colony containing a recombinant pGEX plasmid was incubated into 200 ml of 2×YTA medium. After growing to log phase, gene expression was induced with IPTG for another 6 h. Subsequently, cells were pelleted by centrifugation and washed with 1×PBS. Then *E. coli* was lysed in 10 mL hypotonic buffer (20 mM Tris, 150 mM NaCl, 1.0 mM $MgCl_2$, 1.0 mM EGTA, pH 7.4) containing 0.50 mM PMSF by the sonicator. The proteins were obtained by the removal of insoluble material.

Binding Assays

The Effect of Chain Length:

The prepared beads CL (5.72 mg), CS (6.97 mg), E1 (10.0 mg), and E3 (14.8 mg) were incubated separately with the mixed solution including GST lysates in 0.8 mL of the incubation buffer (20 mM Tris, 150 mM NaCl, 1.0 mM MgCl2, 1.0 mM EGTA, 1% TX-100, 0.10 mM PMSF, pH 7.4, 0.50 mM PMSF) for 1 h at 4° C., washed with the 10 bed volume of incubation buffer for three times and then 100 µL of the SDS-sample buffer was added. After the tubes were cooked for 5 min at 95° C., 20 µL samples were utilized for SDS-PAGE and the gel was stained by CBB G-250 staining solution.

Selectivity of the Dendron-Treated Matrices:

10 mg of samples A, E1, and E3, as well as 100 µg of purified GST or GST-fused protein lysate were used in this experiment. The other steps were same as described above.

Elution of GST Fusion Proteins from Glutathione Sepharose-4B, E1 and E3

Glutathione Sepharose-4B, E1, and E3 were processed as described above. The amount of the protein bound to beads was determined using Image gauge V3.12 (FUJI PHOTO FILM CO., LTD.). The same steps were followed for PX domain of $p47^{phox}$ and Munc-18 fragment lysates.

Dendron-Modified CPG (Sample E1 and E3): Results

Ligand Density Measurement

Due to the difficulties in measuring the amount of immobilized glutathione directly, an indirect method that the ligand density was determined by measuring amount of dibenzofulvene released during the deprotection step was employed. 9-Fluorenylmethoxycarbonyl (Fmoc) protecting group at the apex of the dendron is stable against acids but is readily cleaved by a variety of bases. In this study 20% piperidine in DMF was used to deprotect the Fmoc functional group. Piperidine forms an adduct with the dibenzofulvene, and the adduct absorbs at 301 nm. On the other hand, when the absorbance of the collected solution appeared at 301 nm during the deprotection step with 20% piperidine, it indicated that the deprotection proceeded as intended.

Ligand density obtained with this method is 8.3 μmol/g for E1 and 5.6 μmol/g for E3. The density was reduced by a factor of 11.1 upon modification with Fmoc-(3)-acid and the value was further reduced by a factor of 1.5 upon use of a larger dendron. Thus, in a specific embodiment of the invention, smaller dendrons were more effective at obtaining higher density than using larger dendrons.

GST Binding Assay

Figure 4:
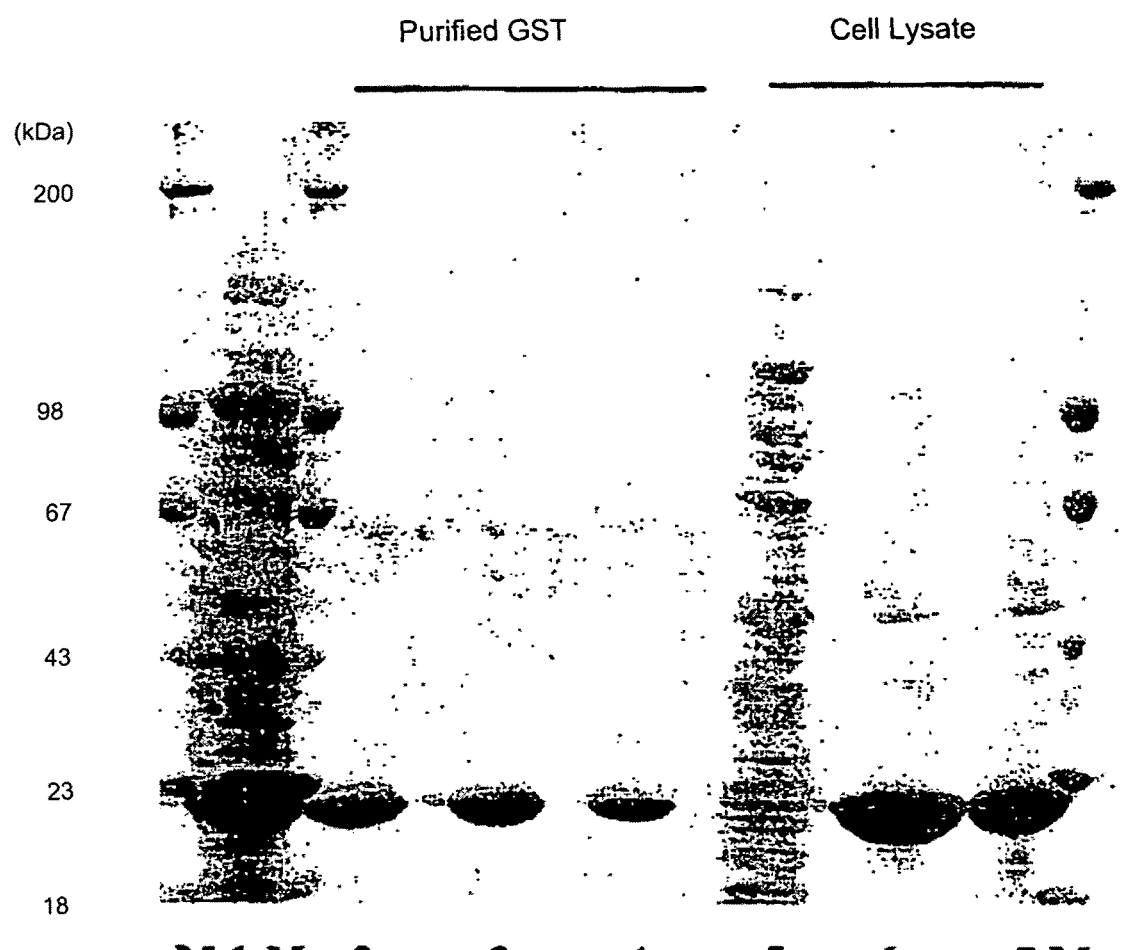
FIG. 4 shows binding of purified GST and GST lysate using three types of beads along with controls.

Binding characteristics of sample A, E1, and E3 were examined using purified GST and cell lysate (lane 2, 3, and 4 in FIG. 4). Lane 1 shows successful preparation of lysate. It is evident that the three matrices bind purified GST effectively. When cell lysate was introduced into the beads (lane 5, 6, and 7), a significant difference was observed between A and E1 or E3. For sample A, in spite of incorporation of BUDGE linkers, serious nonspecific binding was observed. Interestingly, when the dendrons were introduced on the matrix, nonspecific protein binding was effectively suppressed. It is noteworthy that self-assembly of either the dendron of the first generation or the one of the second generation effectively suppresses nonspecific binding of the solid support, while an extended spacer between the dendron and GSH retains the activity of the tethered tripeptide.

Figure 5:
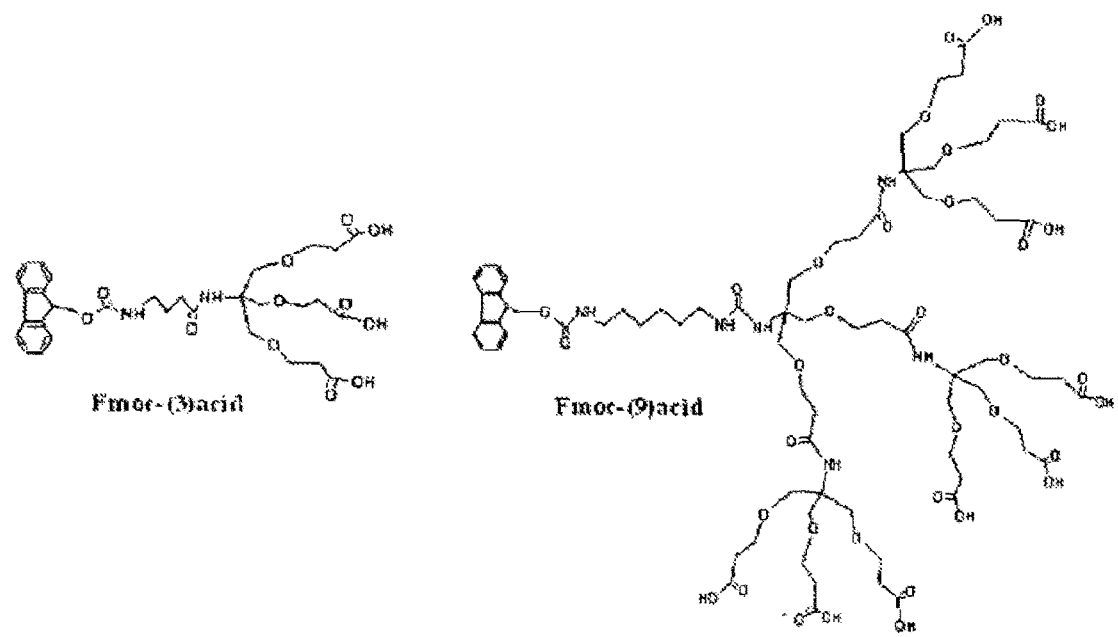
FIG. 5 shows a protected first generation functionalized dendron (E1, Fmoc-(3)acid), and a protected second generation functionalized dendron (E3, Fmoc-(9)acid).

In FIG. 5, in one aspect of the invention, etheral and amide groups constitute the main backbone of the structure, and immobilization of the dendron generates again amide bonds.

The ligand density for E1 is 1.48 times higher than that for E3 (Table 4). In order to examine the binding efficiency of both beads, the weight of the samples was adjusted to have the same number of GSH in each sample. Densitometer showed that the ligand utilization for both cases was quite close (29%, 31%). The larger spacing of E3 did not significantly enhance the binding efficiency of GST. Without being bound by any theory, it is believed that this was because the examined protein is larger than the spacing of both E1 and E3.

TABLE 4

Ligand concentration and ligand utilization of sample E1 and E3.

| Sample | Ligand density (μmol/g) | Ratio of the ligand concentration (%) | % ligand utilization |
|---|---|---|---|
| E1 | 8.3 | 148 | 29 |
| E3 | 5.6 | 100 | 31 |

Control Experiment

Density of GSH was 14.5 μmol/g for CS, 11.9 μmol/g for CL. To compare efficacy of the beads in terms of specific binding of GST, captured proteins with CS (5.7 mg) and CL (7.0 mg) beads were analyzed along with samples from E1 (10.0 mg) and E3 (14.8 mg) beads. The utilized quantity was adjusted to have the same number of the GSH roughly. The chromatogram of CS and CL beads displayed a relatively poor selectivity as well as low binding capacity. The result indicates that the dendron improved accessibility of GST towards immobilized GSH and was effective in suppressing nonspecific binding.

Molecular Weight Dependence

Figure 6:
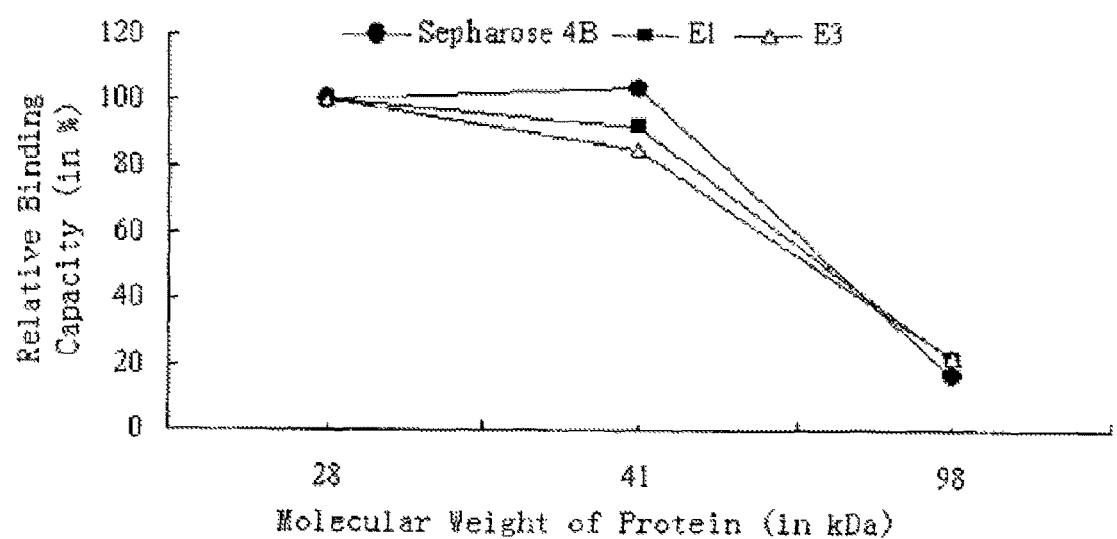
FIG. 6 shows a graph of relative binding capacity vs. molecular weight of proteins attached to the dendron.

As shown in FIG. 6, binding capacity of the beads (E1, E3, and Sepharose 4B) generally decreases as molecular weight of proteins increases. When binding capacity of E1 is set at 100% for GST, GST-PX$^{p47}$ has a relative biding capacity of 92% and 22% for GST-munc18. For E3 bead, 85% for former protein and 23% for the latter protein are recorded. This dependence on protein molecular weight was also observed with glutathione Sepharose-4B. For glutathione Sepharose-4B, the binding efficiencies are 104% and 17% for GST-PX$^{p47}$ and GST-munc18, respectively.

The dendron-modified solid support demonstrates selectivity as high as that of the commercial matrix (for example, Sepharose 4B), and almost same molecular weight dependence as the commercial one. The incorporation of the dendrons on AMPCPG not only reduced the nonspecific binding effectively but retained binding activity of GSH. Constant decrease of the binding capacity as increase of protein molecular weight was observed. In addition to the well-controlled spacing, methods of the invention provide mechanical stability, wide compatibility with various chemical environment, and easiness of handling.

A Dendron-Modified Polystyrene Microtiter Plate

This example examines surface characterization with picoforce AFM and influence of the spacing between the immobilized β-amyloid Proteins.

Polystyrene microtiter plates were purchased from Corning (96 well EIA/RIA plate: #3591, USA) and maleic anhydride activated (Reacti-Bind™ Amine-Binding #15100) plates from Pierce. Polystyrene slides were obtained from Nalge Nunc International (Microscope Slides #160004, USA). The amyloid beta protein (β-amyloid or Aβ$_{1-42}$) purchased from American Peptide Company (USA) was dissolved in sterilized deionized water at a concentration of 1.0 mg/mL, and its stock solution was stored at −70° C. The solution was diluted to desired concentration immediately before the use. Other Aβ fragments (Aβ$_{1-10}$, Aβ$_{1-16}$, and Aβ$_{1-28}$) were purchased from A&Pep (Korea). Antibody 6E10 was from Abcam (UK). Horseradish peroxidase (or HRP)-conjugated Goat anti-Mouse secondary antibody IgG was purchased from Zymed Laboratories (USA). TMB (3,3',5,5'-tetramethylbenzidine) substrate was purchased from Sigma. All chemicals and solvents for the surface modification were of reagent grade from Sigma-Aldrich and the reaction solvent, dimethyl sulfoxide (DMSO), is anhydrous one in a Sure/Seal bottle from Aldrich. All washing solvents for the substrates are of HPLC grade from Mallinckrodt Laboratory Chemicals. The oligonucleotides used for picoforce AFM were purchased from Bionics (Korea). Ultrapure water (18 MΩ/cm) was obtained from a Milli-Q purification system (Millipore, USA).

Figure 7:
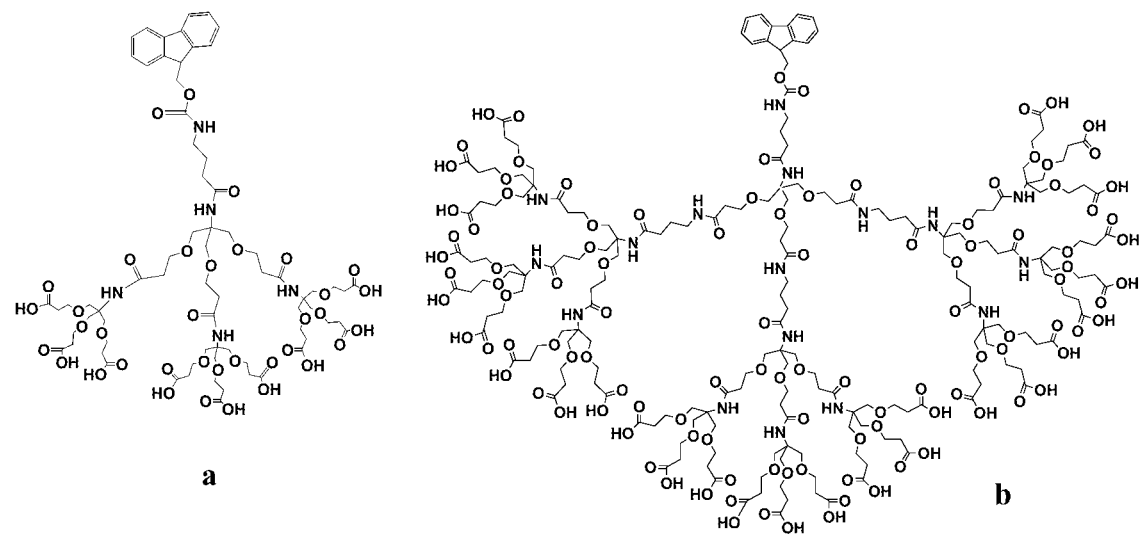
FIG. 7 shows structure of dendron molecules (9-acid and 27-acid in structure a and b, respectively) used in ELISA assay.

The dendron, 9-acid, having an F-moc (or fluorenylmethoxycarbonyl) protection group was prepared as described herein. Briefly, N-[tris(carboxyethoxymethyl) methyl]-4-(9-fluorenylmethoxycarbonyl amino)butyramide was coupled with 3 equivalents of tris[(2-(tert-butoxycarbonyl)ethoxy)methyl]methylamine in the presence of 1-[3-(dimethylamino)propyl]-3-ethylcarbodiimide hydrochloride (or EDC) and 1-hydroxybenzotriazole (or HOBT), and the product was hydrolyzed in 96% formic acid for 18 h to produce the 9-acid (FIG. 7a). The 27-acid (FIG. 7b) was prepared in the similar way.

Preparation of Hydroxylated Surface on Microtiter Plates

The grafting of the monomer was performed inside a plasma reactor. The monomer, di-(ethylene glycol) vinyl ether (or EO2V) [CH$_2$=CH$_2$(OCH$_2$CH$_2$)$_2$OH] was purchased from Aldrich. At first microtiter plate was placed in the center of the chamber (i.e., within the glow region). The reaction chamber was initially evacuated by a rotary pump to the base pressure of 5×10$^{-3}$ Torr. The canister containing the monomer was tape-wrapped and heated to 90° C. using a heating mantle to provide adequate EO2V vapor pressure.

A standard procedure was followed for the monomer deposition. We used argon (Ar) as the purging gas, and the flow was controlled by a mass flow controller (MFC) connected to the main chamber. Initially microtiter plates were subjected to 20 watt peak power (13.56 MHz) argon for 10 min using the continuous wave mode at a pressure of 0.2 Torr, and a constant flow rate of argon 100 sccm was maintained. Subsequently, the reaction chamber was evacuated until the chamber down to a base pressure of $5 \times 10^{-3}$ Torr, and then the EO2V monomer was added for 5 min with constant pressure of 0.1 Torr at RF 5 watt to obtain the polymer and high density of the hydroxyl group. After the plasma treatment the chamber was vented with air, and the plate was taken out from the chamber for the next step.

Preparation of Dendron-Immobilized Microtiter Plates

For the immobilization of the dendron molecule each well of the hydroxylated microtiter plates was filled with the DMSO solution dissolving the dendron (1.0 mM), a coupling reagent, 1-[3-(dimethylamino)propyl]-3-ethylcarbodiimide hydrochloride (or EDC) (9.3 mM), and the catalytic amount of 4-dimethylaminopyridine (DMAP) (0.9 mM), and the plates were placed under dry nitrogen atmosphere for 24 h at room temperature. After the coupling those plates have been washed with DMSO and ethanol in a sequential manner each for 3 min with gentle shaking using a bio-shaker (Mylab). Then the washed plates were dried with a stream of nitrogen and kept in a vacuum chamber (30-40 mTorr) for the next step.

Modification with a DSC Linker

Each well of the dendron-modified plates was filled with anhydrous DMSO solution dissolving 5% (v/v) piperidine, and 3 h at room temperature was allowed for the deprotection. The plates were washed with DMSO and ethanol in a sequential manner for 3 min with gentle shaking, and dried with a stream of nitrogen and kept in a vacuum chamber (30-40 mTorr) for the next step. The wells of the deprotected dendron-immobilized plates were treated with an anhydrous DMSO solution dissolving di(N-succinimidyl)carbonate (DSC, 25 mM) and N,N-diisopropylethylamine (DIPEA, 1.0 mM). The plates of which each cell is filled with the DMSO solution were placed under nitrogen atmosphere for 4 h at room temperature. After discarding the reaction solution, the plates were filled with fresh DMSO, gently shaken for 30 min, and then finally rinsed with ethanol. After being dried with a stream of nitrogen, plates were stored under vacuum (30-40 mTorr) until the subsequent use.

Contact Angle Measurements

Variations of hydrophobicity/hydrophilicity were determined with contact angle (CA) measurement. For the measuring of CA we used polystyrene slides instead of the microtiter plates because of the incompatibility faced due to their well shape. Polystyrene slides were treated side by side while the microtiter plates were modified. The water CA was measured by using a DSA10 Mk2 (KRÜSS, Germany) measurement system. The static CA was measured by placing a water drop from a syringe needle onto the sample surface. Typically, at least five drops have been examined on different parts of an identical sample substrate and averaged. The photographs of the droplets have been captured, and fitted with a built-in program. Each datum represents the average of the values from fifteen positions of three slides, five positions for each.

Dendron-Modified Surface Characterization Through Picoforce AFM Analysis

Picoforce AFM was employed for analyzing the dendron-immobilized surface (Scheme 2). For this experiment we also used polystyrene slides, which were treated simultaneously along with the microtiter plates.

The substrates and the cantilevers treated with the DSC linker were soaked in a solution dissolving a relevant oligonucleotide (20 μM, 25 mM NaHCO3 buffer (pH 8.5), 5.0 mM MgCl2) for 12 h at room temperature. Then the substrates and the cantilevers were placed in a stirred buffer solution (2×SSPE buffer (pH 7.4) containing 7.0 mM sodium dodecylsulfate (or SDS)) at 37° C. for 1 h and then in boiling water for 5 min to remove nonspecifically bound oligonucleotides. Finally, the substrates and the cantilevers were dried under vacuum (30-40 mTorr). The picoforce AFM measurements were performed with a Nano Wizard AFM (JPK Instruments). All measurements were carried out in a fresh PBS buffer (pH 7.4) at room temperature. The thermal fluctuation method has been applied for the calibration of spring constant of each AFM tip in solution before the measurement. The calculated spring constants of the cantilevers employed in the experiment varied between 12 and 15 pN/nm. The binding force and the unbinding force were recorded at 0.20 μm s$^{-1}$. The force-distance curves were recorded more than seventy times at one position, and at least more than 5 spots were examined in each separate experiment. The experiment was repeated more than three times using a new tip and a new substrate to check the reproducibility.

Antigen Capture and Detection

The amyloid beta protein (beta-amyloid) $A\beta_{1-42}$ (MW=4.7 KD), the primary component of Alzheimer's disease plaques, was used as an antigen to display on microtiter plates. Commercially available microtiter plates, unmodified polystyrene plate (Corning) and maleic anhydride activated plate (Pierce), were used in parallel as a comparison. The PBS solutions of $A\beta_{1-42}$ in various concentrations were prepared through a serial dilution, and 50 μl of each solution was loaded into a well of the dendron-modified plate, maleic anhydride plate, and normal plate. After the load the plates were sealed with Mylar tapes to prevent drying, and the loaded plates were incubated for 2 h at room temperature (dendron-modified, maleic anhydride) or for overnight at 4° C. (unmodified polystyrene plate). After the solution was discarded, 150 μl of a blocking solution (3% skim milk in PBS) was added into each well, and the filled plates were incubated for 2 h at room temperature with gentle shaking. After the blocking solution was discarded, the wells were washed with PBST (PBS with 0.05% Tween20) for three times. A mouse monoclonal antibody 6E10 (1 mg/ml), which is specific to N-terminal region (3-8 aa) of Aβ protein, was diluted by a factor of 2000 in PBST, 50 μl of the resulting solution was added in each well, and the incubation of 2 h was allowed at room temperature. After decanting the antibody solution, the plates were thereafter washed three times with PBST. A horseradish peroxidase (or HRP)-conjugated Goat anti-Mouse secondary antibody IgG (1 mg/ml) was diluted by a factor of 2000 in PBST, 50 μl of the resulting solution was added in each well, and 2 h was allowed at room temperature. The wells were washed thoroughly three times with PBST. After adding TMB (3,3',5,5'-tetramethylbenzidine) substrate solution (50 μl/well), 15 min was allowed at room temperature. Absorbance was measured at 450 nm by using a microtiter plate reader (VesaMax™, Molecular Devices) after adding 50 μl of 1.0 N HCl in each well. Different fragments of beta-amyloid, $A\beta_{1-28}$ (3.5 KD), $A\beta_{1-16}$ (2.0 KD), and $A\beta_{1-10}$ (1.2 KD) along with $A\beta_{1-42}$ were used for comparing the detection efficiency. All measurement was carried out in triplicate on each day, and was repeated on three different days. The background value was subtracted from the measured one for the data analysis.

Results and Discussion for a Dendron-Modified Polystyrene Microtiter Plate Example Di-(ethylene glycol) vinyl ether (or EO2V) was attached to the surface of polystyrene microtiter plates as it suppressed the nonspecific binding of proteins. The resulting hydroxyl functional group on the polystyrene surface was used to anchor dendron molecules (FIG. 14). This grafted PEO surface has interesting properties; particularly with respect to the minimization of nonspecific adsorption of biomolecules. Initially, during the pretreatment of polystyrene at RF 20 watt bluish-lavender color was observed inside the chamber, but the "visible plasma" was not observed at RF 5 watt, at which the monomer was allowed. The low power of RF has been used to promote the grafting, while avoiding degradation of the monomers. Pretreatment of polystyrene at 20 watt RF power generated free radicals that initiated the polymerization of the vinylic monomer on surface. Reproducible CAs have been observed for the resulting substrates.

Any of the treatment processes did not affect adversely the transparency of the microtiter plate, which is useful in the colorimetric assay. The absorbance was recorded to follow change of the optical clarity of the microtiter plate. The plate was examined before and after each reaction step with the help of microtiter plate reader (VesaMax™, Molecular Devices) recording at 450 nm. There was no significantly noticeable change in the absorbance at 450 nm during each treatment. The absorbance of each well was measured at least three times just prior to the plasma treatment, and the average value was 0.048±0.004. The absorbance remained unchanged after the plasma treatment and the final immobilization of the DSC linker. The data revealed that the reaction conditions did not deteriorate the transparency of the microtiter plate. For checking impact of solvents on polystyrene surface, the absorbance was recorded before and after the addition of a solvent in the microtiter wells. For this study, wells were filled with DMSO (200 µl for each well), ethanol, and an 1:1 mixture of DMSO and ethanol. Five wells were filled with each solvent and left standing for 5 h. Subsequently the solvents were discarded, and the plate was dried under vacuum (30-40 mTorr) for 1 h before measuring the absorbance at 450 nm. The average value was consistently 0.048±0.005 for each case. The data showed that solvents did not damage the plate transparency.

Water Contact Angle Measurements

A static water contact angle of the substrate was measured to follow surface energy change upon each modification step. The contact angle ("CA") data revealed changes in the hydrophobicity/hydrophilicity of the substrate. The water contact angle observed on bare polystyrene plates was 69.2±2.5° on average. After the argon plasma treatment for 5 min at RF 20 watt, the CA decreased to (42.2±3.8°). In the subsequent treatment, grafting of EO2V resulted in CA value of (23.4±2.3°) confirming that the grafting actually took place. The grafted substrate was stable in atmosphere and even after its exposure to DMSO for several hours. After the immobilization of the second generation dendron ("9-acid") the contact angle increased to (56.3±2.5°). Without being bound by any theory, it is believed that this change in CA reflects conversion of at least some of the hydroxyl groups to an ester and/or the medium polarity of the dendron backbone. Various spots on each slide were examined to check the uniformity, and the average variation was 1.5°, while the slide-to-slide variation was 2.5°. CA was also measured after immobilization of the third generation dendron ("27-acid"). The observed value (54.3±1.5°) was very similar to the value obtained for the 9-acid modified surface. The average variation of 1.0° and 1.5° were observed for spot-to-spot and slide-to-slide comparison, respectively.

Figure 8:
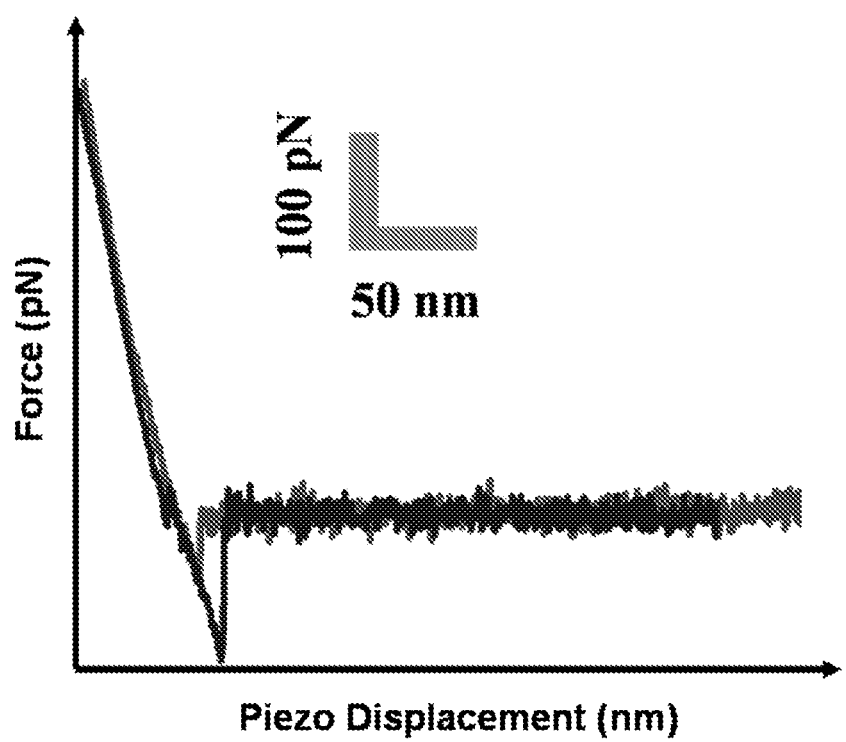
FIG. 8 is a plot of a typical force-displacement curve obtained upon approaching (grey) and retracting (black) an AFM tip. The AFM tip was modified with the 27-acid of FIG. 7 and the substrate was modified with the 9-acid of FIG. 7. DNA was conjugated at an apex of the dendrons.

Characterization of the Dendron-Immobilized Surface Through Picoforce AFM Analysis A bio-AFM analysis represents a new approach for examining the dendron functionalized surface. Such analysis is schematically shown in FIG. 15. An oligonucleotide of 50-mer (5'-$H_2N$-GTCTGACCTGTTCCAACGACCCG-TATCACTCCGCTCCTGCCTGCT CTCCA-3', GC content=60%) was coupled with the 9-acid-modified polystyrene slides, and the complementary DNA (5' $H_2N$-TGGAGAGCAGGCAGGAGCGGAGTGATACGGGTCGTT GGAACAGGTCAGAC-3', GC content=60%) was conjugated to dendron-modified AFM tips via their 5' termini. For all the measurements, silicon nitride AFM tips were modified with the third generation dendron (27-acid) according to the dendron-based tip functionalization method and the force-distance curves were recorded as the functionalized AFM tip and the surface were brought in and out of contact (FIG. 8). In this measurement, both binding forces (attractive forces) and unbinding forces (adhesive forces) were observed.

Figure 9:
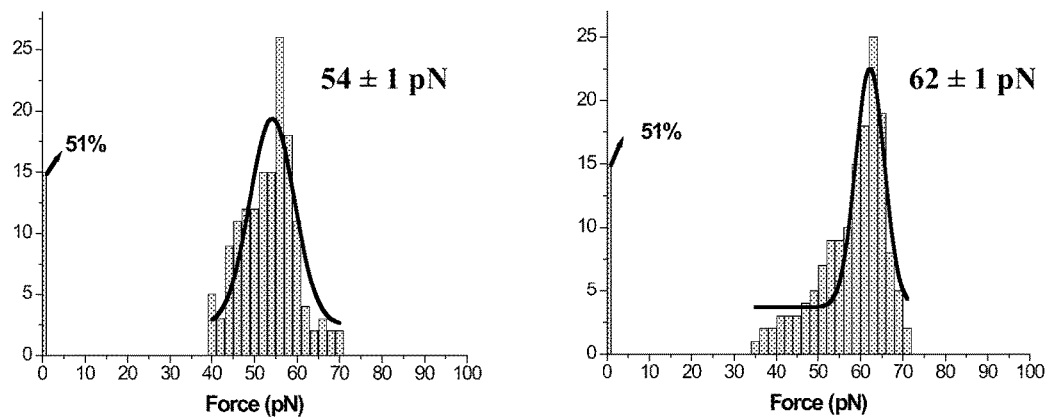
FIG. 9 shows the force histograms of (a) the binding and (b) the unbinding forces recorded at 0.2 µm s$^{-1}$ for the oligonucleotides of 50-mer in FIG. 8. The y-axis shows the probability of observing the force of a particular magnitude within each distribution. Gaussians fitting gave the mean value of 54±1 pN for the binding event, and 62±1 pN for the unbinding event, respectively.

The binding and unbinding forces recorded at 0.20 µm $s^{-1}$ are shown in FIG. 9. The distribution was fitted with a Gaussian curve, and the most probable force was 54±1 pN (FIG. 9a) for the binding and 62±1 pN (FIG. 9b) for the unbinding. The values are close to those reported for a DNA duplex of the same length and GC content. Because the binding force is relatively insensitive to the measurement speed, the value is almost identical. In contrast, the unbinding force depends on the retraction speed. Thus, the increase of force value by 4 pN can be explained by the increase of the speed from 0.10 µm $s^{-1}$ to 0.20 µm $s^{-1}$. It was observed that 49% of the measurements exhibited force-distance curves with a single clean peak, for both cases. For further confirmation of the specificity of the tip-substrate interactions recorded for the fully complementary cases, control experiments were carried out. For this end, substrates such as pristine polystyrene and EO2V grafted substrate were treated in the same way as the dendron-modified surface, and the forces between the DNA-tethered AFM tip were measured. The measurement showed that no interaction was observed by chance of >98%. It is believed that the polystyrene surface adsorbed the free DNA in solution nonspecifically, and the DNA-adsorbed surface does not allow the specific interaction with the 50-mer on the AFM tip. Nonspecific interaction was not observed between the grafted surface and the DNA on the tip. These data confirm the interactions observed for DNA-tethered AFM tip and the DNA-modified substrate are specific.

Figure 10:
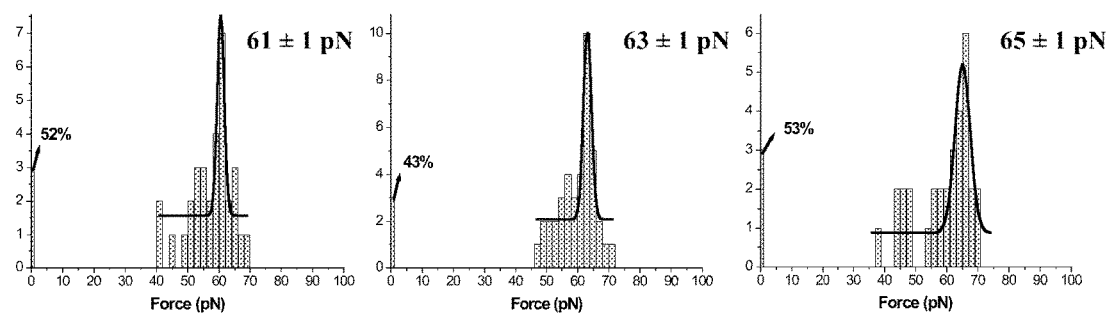
FIG. 10 is force histograms of the spots examined for the force measurement related to FIG. 8. The unbinding forces were used for the analysis. For the force measurement five spots were selected within a chosen area (1.0 µm×1.0 µm) of a substrate.
Figure 10:
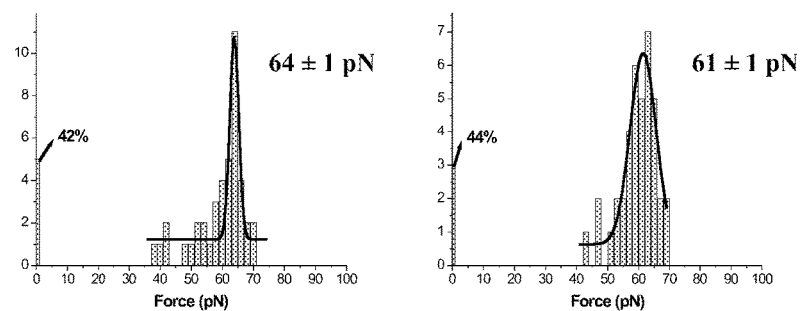

To determine the surface homogeneity, five spots within a chosen area (1.0 µm×1.0 µm) on each substrate were analyzed and recorded seventy force-distance curves on each spot. A consistent mean force value was observed for different spots (FIG. 10) indicating a uniform distribution of the immobilized DNAs and the dendrons on the surface. Although the shape of the histograms varied somewhat, the most probable forces from the Gaussian fitting are within 61-65 pN. AFM was used to confirm the chemical status on the modified polystyrene surface. It was found that the modified surface with 9-acid was substantially homogeneous.

Figure 11:
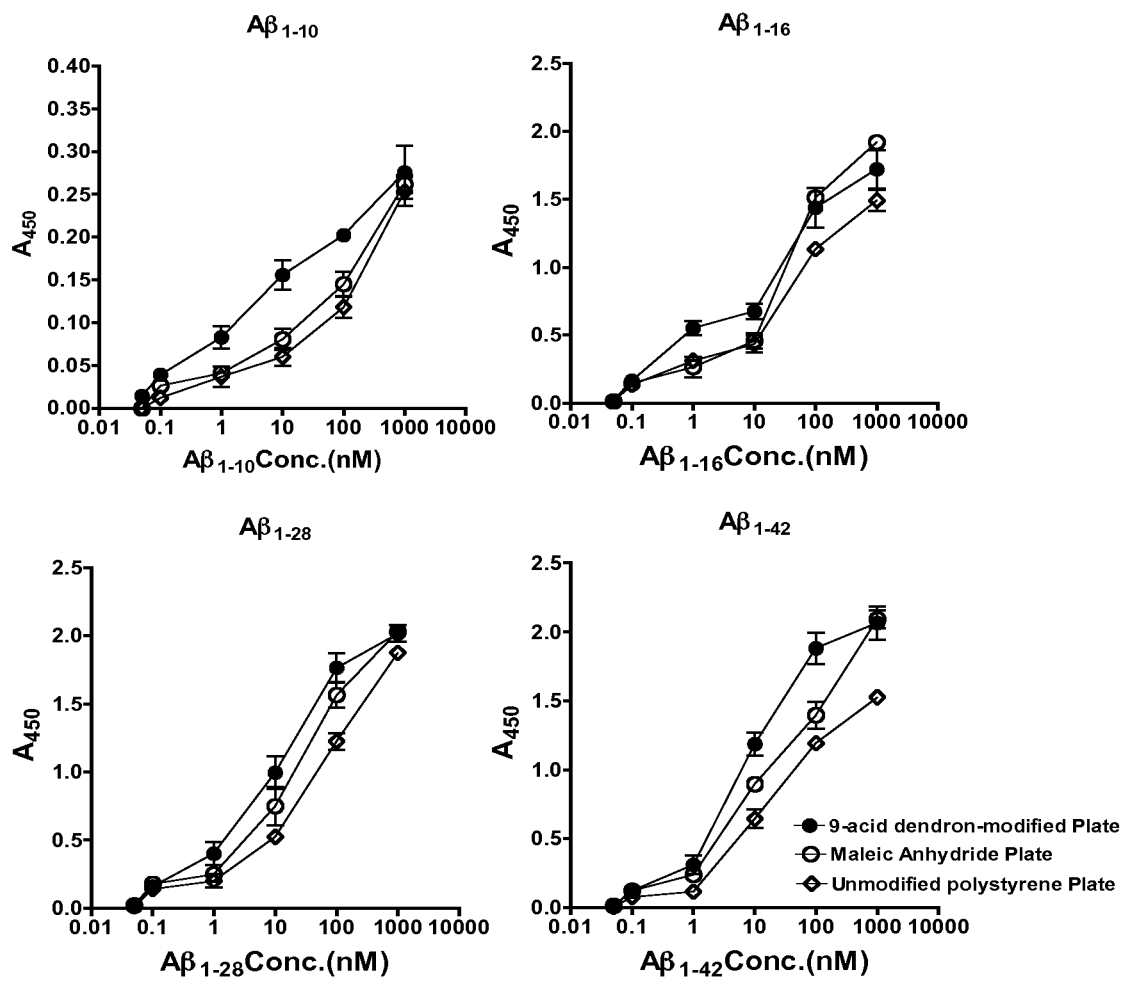
FIG. 11 is ELISA of different Aβ fragments on 9-acid-immobilized plate compared with other conventional plates.

Efficiency of a 9-Acid Dendron-Immobilized Plate Compared with Other Conventional Plates In order to detect Aβ antigens in samples, typically the corresponding antibodies are immobilized on ELISA plates. In this study, to examine the effectiveness of the spacing generated by the dendrons on surface, various fragments of Aβ were immobilized on the dendron-modified surface instead, and the primary antibody and the secondary antibody conjugated with a catalytic enzyme were applied sequentially. The deprotected (or activated) dendron surface was utilized for the covalent immobilization of Aβ protein (and its fragments). For comparison purpose, commercially available maleic anhydride activated plates were used, which offers the covalent immobilization of the biomolecules. Along with these, unmodified microtiter plates were chosen, where the biomolecules were immobilized through the passive adsorption. At first, these plates were compared by immobilizing the Aβ protein (and its fragments) as a target antigen on these surfaces and using them in an ELISA process. Mouse monoclonal antibody 6E10 specific to N-terminal region (3-8 aa) of Aβ was used for the assay. The results of Aβ assay are shown in FIG. 11. The signal of ELISA was obtained in a dose-dependent manner in all the concentration range of 50 pM~1.0 μM, and enhanced signals were observed for the dendron-modified plate in all cases of the Aβ size up to 100 nM concentration of the antigen. The low absorbance observed in case of $A\beta_{1-10}$ seems be attributable to the poor affinity of 6E10 to $A\beta_{1-10}$. At the concentrations higher than 100 nM, the dendron plate showed earlier saturation of the response curve compared to other plates, and showed similar or, in a case of $A\beta_{1-16}$ a weaker signal. Without being bound by any theory, this early saturation of the dendron surface could be interpreted as a result of relatively low molecular density of the dendron on the surface and, hence, relatively small number of antigen available for the Aβ antibody at the high concentration. Much higher signals were obtained with the dendron-modified plate at the low concentration ranges, which is of interest for most of biomarker assays in clinical laboratories. The enhancement was, in case of $A\beta_{1-10}$ detection, at least 10-fold compared to the maleic anhydride plate and about 15-fold compared to the unmodified polystyrene plate (cf. the concentrations needed for a certain absorbance value of 0.10 or 0.15). But the increments were generally reduced as the size of the antigen increased to $A\beta_{1-28}$ and $A\beta_{1-42}$. Subsequently, a 27-acid dendron-modified plate that gave more spacing between the immobilized antigens on surface was studied for the Aβ detection.

Efficiency of a 27-Acid Dendron-Immobilized Plate Compared with Other Conventional Plates In order to provide more spacing between the antigens on surface, a third generation of dendron, i.e., 27-acid with an average spacing of 6.5 nm instead of the previous 9-acid (with ca. 3 nm spacing) was chemically immobilized on polystyrene microtiter plates using the procedures described herein. The globular aggregates of $A\beta_{1-42}$ having convoluted diameter of 4.4±0.4 nm have been reported, which suggests that the spacing provided by 9-acid may not be sufficient for the larger fragments of Aβ. The results of ELISA with 27-acid are shown in FIG. 12. In contrast with the results of 9-acid modified plates, the signal increments of 27-acid modified plates compared to two other conventional plates were getting bigger with increasing sizes of the Aβ antigen used. But in case of the small size of $A\beta_{1-10}$, there was no significant difference between the signals obtained between 9-acid and 27-acid modified plates. It is believed that the enhanced detection efficiency of larger size of Aβ fragments on 27-acid dendron-modified surface compared to 9-acid dendron-modified surface is due to the difference in the spacing on surface. Generally better performance of the dendron-modified plates were observed compared with conventional unmodified polystyrene plate or maleic anhydride activated plate in a wide range of the antigen concentrations, 50 pM~1.0 μM. The lateral spacing increase had a significant beneficial influence on the detection of large size proteins.

Effect of Mesospacing of Dendron Molecules for Detection of Biomolecules

For checking the effect of mesospacing of dendron molecules directly, the detection efficiency of 9-acid and 27-acid dendron-modified plate were compared by simultaneously performing the ELISA at the same time and in same conditions. The results are plotted in FIG. 13. Overall, similar results for each dendron plate as shown in previous figures (FIG. 11 and FIG. 12) were obtained. In the case of $A\beta_{1-10}$ fragment, there was not much significant difference in detection efficiency between two dendron surfaces. But as the size of the Aβ increased, the effectiveness of spacing was observed throughout all ranges of concentrations. The comparative curves plotted for $A\beta_{1-16}$, $A\beta_{1-28}$ and $A\beta_{1-42}$ showed that the 27-acid dendron-modified plate has better detection efficiency for larger size of the Aβ molecules. In case of $A\beta_{1-42}$, in order to reach absorbance of 0.50, 9-acid dendron-modified surface required the antigen concentration of 8-fold higher than 27-acid modified surface. The enhancement indicates that 27-acid dendron provides the appropriate spacing for $A\beta_{1-42}$ on surface.

As shown in the discriminative spacing effect of the third generation dendron (27-acid) with $A\beta_{1-42}$ of molecular weight of 4.7 KD, it is expected that application of fourth generation dendron (81-acid) should be suitable for the immobilization of proteins with high molecular weights on surface.

Antibody Array with Dendron-Modified Slides
Sera Treatment & Fluorescent Labeling of Serum Proteins Serum albumin was removed according to the protocol of PROT-IA Immunoaffinity Albumin & IgG Depletion Kit (Sigma), and the total protein concentration was measured by BCA assay. Each tube of dye stock was dissolved in 375 μl of DMSO. After adding 5 μl of 0.5M sodium bicarbonate pH 9.2 in 18 μl of Cy3 or Cy5 de stock tube, the mixture was transferred to 2 μl of serum sample (3.9 mg/ml). The mixture was incubated for 45 min in the dark at room temperature, and then the reaction was quenched with 1M Tris pH 8.0 (half volume of above mixture). After incubation for 15 min in the dark, 1×PBST was added and the total volume was adjusted to 463 μl. The sample was transferred to Microcon-10 column, and it was spun at 14,000×g for 15 min. After discarding the flow-through, 500 μl PBST was added to column and the previous spinning step was repeated. These two sequential spinning steps were repeated two more times. The final volume was reduced to less than 100 μl, and the column was placed upside down in a fresh tube and was spun at 14,000×g for 5 min.

Activation of Dendron-Coated Slides

About 900 mg of DSC was added in 200 ml of acetonitrile with 0.5 ml diisopropylethylamine (DIPEA), and the solution was stirred until DSC dissolved. Dendron-coated slides were soaked in the reaction solution. After 4 hours, the slides were washed with ethanol, dried with a nitrogen gas, and stored under vacuum or nitrogen atmosphere before microarray fabrication.

Fabrication and Printing of Array

Antibodies were diluted in printing buffer (PBS pH 8.5, 0.05 mg/ml BSA, 0.01% Tween 20) to a final concentration of 0.1, 0.2, 0.35 or 0.5 mg/ml. Eight replicates of each antibody sample are arrayed by spotting 10 drops at each position, using contact or non-contact printer. The printed slides were incubated in a 75% humidity chamber overnight.

Array Blocking

The array-printed slides were washed with PBST buffer solution (1×PBS, pH 7.4, with 0.05% Tween 20) and then with D.I. water twice. The slides were placed in a 50 ml tube filled with Blocking Solution (3% nonfat dry milk in PBS (pH 7.4)) and shaken at 105 rpm for 2 hours. Slides were removed, washed thoroughly with PBST and D.I. water, and dried.

Array Hybridization

About 100 μl of dye-labeled serum sample was loaded onto each array-printed slide. After assembling the Agilent hybridization chambers, slides were rotated and incubated for 2 hours at room temperature in a hybridization oven, removed from the oven, and were immediately washed twice with PBST by stirring at 10,000 rpm for 5 minutes, and then twice with PBS by stirring at 10,000 rpm for 5 minutes. After washing twice with D.I. water, the slides were dried and scanned with a fluorescence scanner for analysis.

Result of Antibody Array with Dendron-Modified Slides Experiment

Antibody microarrays were fabricated on both a dendron slide and a hydrogel slide with a monoclonal antibody to specifically bind an antigen, apolipoprotein A-I (apoA-I) at different concentrations. FIG. 16 shows the fluorescence images of an antibody microarray after hybridization with apoA-I. It is clear that the dendron slide provided much higher signal intensity over the whole range of antibody concentration than the hydrogel slide, still retaining low background noise. In addition, the dendron slide showed outstanding sensitivity in detecting antigen (FIG. 17).

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A composition comprising an array of conically-shaped dendrons that are bound to a surface of a planar, non-porous solid support, wherein said dendron is selected from a compound of the formula:

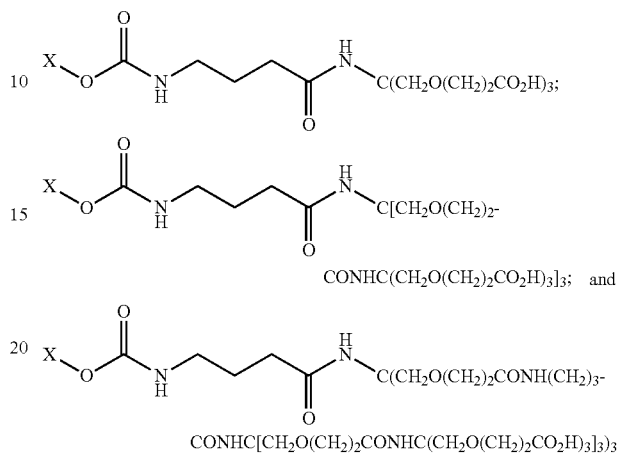

wherein
X is a probe;
a plurality of carboxylic acid terminal functional groups on said dendron are covalently attached to the surface of said solid support.

2. The composition of claim 1, wherein the probe comprises an oligonucleotide, an oligopeptide, an enzyme, a substrate, a drug, a drug-receptor, PNA, LNA, aptamer, antibody, antigen, oligonucleotide analog, or a combination thereof.

3. The composition of claim 1, wherein a discrimination efficiency of the probe is at least 80%.

4. The composition of claim 1, wherein a relative amount of non-specific binding to the amount of the specific binding of the probe is reduced by at least about 60% compared to the probe that is attached to a non-dendron molecule.

5. The composition of claim 1, wherein said solid support is glass.

6. The composition of claim 1, wherein the probe is an oligonucleotide, an oligopeptide, a receptor, or a substrate.

7. The composition of claim 6, wherein the receptor comprises a drug receptor.

8. The composition of claim 1, wherein the probe is an oligonucleotide.

9. The composition of claim 8, wherein a discrimination efficiency of the probe for a single nucleotide polymorphism is at least about 80%.

10. The composition of claim 8, wherein a relative amount of non-specific binding to the amount of the specific binding is reduced by at least about 60% compared to the oligonucleotide probe attached to a non-dendron molecule.

11. The composition of claim 1, wherein said dendron is of the formula:

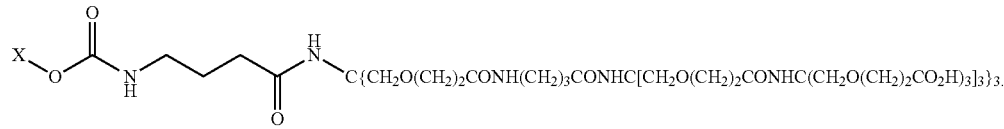

12. The composition of claim 11, wherein at least nine carboxylic acid termini of said dendron are attached to the surface of said solid support.

13. The composition of claim 11, wherein at least twelve carboxylic acid termini of said dendron are attached to the surface of said solid support.

14. The composition of claim 11, wherein at least twenty one carboxylic acid termini of said dendron are attached to the surface of said solid support.

* * * * *